United States Patent
Hyde et al.

(10) Patent No.: US 8,221,690 B2
(45) Date of Patent: Jul. 17, 2012

(54) SYSTEMS AND DEVICES THAT UTILIZE PHOTOLYZABLE NITRIC OXIDE DONORS

(75) Inventors: Roderick A. Hyde, Redmond, WA (US); Muriel Y. Ishikawa, Livermore, CA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1238 days.

(21) Appl. No.: 11/998,864

(22) Filed: Nov. 30, 2007

(65) Prior Publication Data

US 2009/0110958 A1 Apr. 30, 2009

Related U.S. Application Data

(63) Continuation-in-part of application No. 11/981,743, filed on Oct. 30, 2007.

(51) Int. Cl.
*B01J 19/08* (2006.01)
(52) U.S. Cl. ................................. 422/186.3
(58) Field of Classification Search ............... 422/186.3
See application file for complete search history.

(56) References Cited

U.S. PATENT DOCUMENTS

| | | |
|---|---|---|
| 4,162,536 A | 7/1979 | Morley |
| 4,210,697 A | 7/1980 | Adiletta |
| 4,248,214 A | 2/1981 | Hannah et al. |
| 4,561,429 A | 12/1985 | Sato et al. |
| 4,611,594 A | 9/1986 | Grayhack et al. |
| 4,919,149 A | 4/1990 | Stang |
| 5,109,871 A | 5/1992 | Thornton |
| 5,351,698 A | 10/1994 | Wheeler et al. |
| 5,366,997 A | 11/1994 | Keefer et al. |
| 5,374,710 A | 12/1994 | Tsien et al. |
| 5,405,919 A | 4/1995 | Keefer et al. |
| 5,530,263 A | 6/1996 | DiVincenzo |
| 5,571,152 A | 11/1996 | Chen et al. |
| 5,580,433 A | 12/1996 | Baker et al. |
| 5,665,077 A | 9/1997 | Rosen et al. |
| 5,676,963 A | 10/1997 | Keefer et al. |
| 5,683,668 A | 11/1997 | Hrabie et al. |
| 5,690,777 A | 11/1997 | Kuethe et al. |
| 5,736,152 A | 4/1998 | Dunn |
| 5,765,558 A | 6/1998 | Psaros et al. |
| 5,814,666 A | 9/1998 | Green et al. |
| 5,858,799 A | 1/1999 | Yee et al. |
| 5,900,433 A | 5/1999 | Igo et al. |
| 5,910,316 A | 6/1999 | Keefer et al. |
| 5,943,160 A | 8/1999 | Downing |
| 5,956,172 A | 9/1999 | Downing |
| 5,980,705 A | 11/1999 | Allen et al. |

(Continued)

FOREIGN PATENT DOCUMENTS

DE 20115123 U1 6/2001

(Continued)

OTHER PUBLICATIONS

Stubbington, Tommy; "New Condom Nears Approval"; The Wall Street Journal Online; bearing at date of Apr. 20, 2011; pp. 1-2; 13:18; Dow Jones & Company, Inc.

(Continued)

*Primary Examiner* — Kishor Mayekar

(57) ABSTRACT

The present disclosure relates to systems and devices that utilize photolyzable nitric oxide donors.

31 Claims, 36 Drawing Sheets

FIG. 20E

U.S. PATENT DOCUMENTS

| | | | |
|---|---|---|---|
| 5,994,444 A | 11/1999 | Trescony et al. | |
| 6,000,398 A | 12/1999 | Alla et al. | |
| 6,037,346 A | 3/2000 | Doherty, Jr. et al. | |
| 6,080,110 A | 6/2000 | Thorgersen | |
| 6,100,096 A | 8/2000 | Bollinger et al. | |
| 6,103,765 A | 8/2000 | Neal | |
| 6,127,363 A | 10/2000 | Doherty, Jr. et al. | |
| 6,143,314 A | 11/2000 | Chandrashekar et al. | |
| 6,149,606 A | 11/2000 | Alving et al. | |
| 6,156,753 A | 12/2000 | Doherty, Jr. et al. | |
| 6,182,661 B1 | 2/2001 | Solanki et al. | |
| 6,190,704 B1 | 2/2001 | Murrell | |
| 6,223,747 B1 | 5/2001 | Rudge et al. | |
| 6,280,604 B1 | 8/2001 | Allen et al. | |
| 6,287,601 B1 | 9/2001 | Russell | |
| 6,306,609 B1 | 10/2001 | Lai | |
| 6,308,708 B2 | 10/2001 | Strauss et al. | |
| 6,321,751 B1 | 11/2001 | Strauss et al. | |
| 6,327,074 B1 | 12/2001 | Bass et al. | |
| 6,341,607 B1 | 1/2002 | Couvreur | |
| 6,369,071 B1 | 4/2002 | Haj-Yehia | |
| 6,432,077 B1 | 8/2002 | Stenzler | |
| 6,436,470 B1 | 8/2002 | Iacocca et al. | |
| 6,440,498 B2 | 8/2002 | Schaller | |
| 6,451,337 B1 | 9/2002 | Smith et al. | |
| 6,469,051 B2 | 10/2002 | Nagano et al. | |
| 6,559,184 B2 | 5/2003 | Neal | |
| 6,621,687 B2 | 9/2003 | Lewis, Jr. et al. | |
| 6,635,273 B1 | 10/2003 | Loscalzo et al. | |
| 6,635,415 B1 | 10/2003 | Bollinger et al. | |
| 6,636,652 B1 | 10/2003 | Kopelman et al. | |
| 6,639,007 B2 | 10/2003 | Plamthottam | |
| 6,651,667 B2 | 11/2003 | Osterberg | |
| 6,673,338 B1 | 1/2004 | Arnold et al. | |
| 6,673,871 B2 | 1/2004 | Warneke et al. | |
| 6,696,072 B1 | 2/2004 | Podolski | |
| 6,706,274 B2 | 3/2004 | Herrmann et al. | |
| 6,743,249 B1 | 6/2004 | Alden | |
| 6,747,062 B2 | 6/2004 | Murrell | |
| 6,773,714 B2 | 8/2004 | Dunn et al. | |
| 6,812,500 B2 | 11/2004 | Reeh et al. | |
| 6,818,356 B1 | 11/2004 | Bates | |
| 6,840,244 B2 | 1/2005 | Kemp | |
| 6,841,166 B1 | 1/2005 | Zhang et al. | |
| 6,900,891 B2 | 5/2005 | Kopelman et al. | |
| 6,943,166 B1 | 9/2005 | Pullman et al. | |
| 6,969,507 B2 | 11/2005 | Weisskoff et al. | |
| 6,983,751 B2 | 1/2006 | Osterberg | |
| 6,994,934 B2 | 2/2006 | Stanish et al. | |
| 7,052,711 B2 | 5/2006 | West et al. | |
| 7,088,040 B1 | 8/2006 | Ducharme et al. | |
| 7,105,502 B2 | 9/2006 | Arnold et al. | |
| 7,105,607 B2 | 9/2006 | Chen | |
| 7,122,046 B2 | 10/2006 | Augustine et al. | |
| 7,122,529 B2 | 10/2006 | Ruane et al. | |
| 7,144,655 B2 | 12/2006 | Jenson et al. | |
| 7,181,174 B2 | 2/2007 | Fitzgibbon et al. | |
| 7,181,261 B2 | 2/2007 | Silver et al. | |
| 7,183,001 B1 | 2/2007 | Ederle et al. | |
| 7,189,471 B2 | 3/2007 | Jankowksi et al. | |
| 7,194,801 B2 | 3/2007 | Jenson et al. | |
| 7,206,605 B2 | 4/2007 | Hattori | |
| 7,210,817 B2 | 5/2007 | Lee et al. | |
| 7,215,687 B2 | 5/2007 | Kawai et al. | |
| 7,215,887 B2 | 5/2007 | Ternullo et al. | |
| 7,217,882 B2 | 5/2007 | Walukiewicz et al. | |
| 7,218,900 B2 | 5/2007 | Suzuki | |
| 7,220,258 B2 | 5/2007 | Myhr | |
| 7,227,956 B1 | 6/2007 | Onishi | |
| 7,235,189 B2 | 6/2007 | Höhn et al. | |
| 7,235,361 B2 | 6/2007 | Bawendi et al. | |
| 7,235,505 B2 | 6/2007 | Gromelski et al. | |
| 7,236,595 B1 | 6/2007 | Bean et al. | |
| 7,238,628 B2 | 7/2007 | Demaray et al. | |
| 7,245,894 B2 | 7/2007 | Sekiguchi et al. | |
| RE39,785 E | 8/2007 | Fuse | |
| 7,253,953 B2 | 8/2007 | Browning | |
| 7,254,160 B2 | 8/2007 | Kawamoto et al. | |
| 7,256,923 B2 | 8/2007 | Liu et al. | |
| 7,257,327 B2 | 8/2007 | Small | |
| 7,260,155 B2 | 8/2007 | Stonick et al. | |
| 7,260,402 B1 | 8/2007 | Ahmed | |
| 7,260,764 B2 | 8/2007 | Chen | |
| 7,260,768 B1 | 8/2007 | Matsumoto et al. | |
| 7,261,693 B2 | 8/2007 | Wilcox et al. | |
| 7,264,602 B1 | 9/2007 | Longsworth | |
| 7,273,567 B1 | 9/2007 | Wellinghoff et al. | |
| 7,280,811 B2 | 10/2007 | Sugiyama et al. | |
| 7,283,710 B2 | 10/2007 | Sano et al. | |
| 7,294,678 B2 | 11/2007 | McGlothlin et al. | |
| 7,294,779 B2 | 11/2007 | Watabe et al. | |
| 7,295,737 B2 | 11/2007 | Moorjani et al. | |
| 7,295,741 B2 | 11/2007 | Sako et al. | |
| 7,298,605 B2 | 11/2007 | Itoh et al. | |
| 7,298,977 B2 | 11/2007 | Ohsawa et al. | |
| 7,301,751 B2 | 11/2007 | Lee et al. | |
| 7,301,754 B1 | 11/2007 | Knowles | |
| 7,303,333 B2 | 12/2007 | Yu | |
| 7,582,623 B2 * | 9/2009 | Mascharak | 514/185 |
| 7,603,166 B2 * | 10/2009 | Casscells et al. | 600/473 |
| 7,899,539 B2 | 3/2011 | Whitehurst et al. | |
| 2002/0022046 A1 | 2/2002 | Tedeschi et al. | |
| 2002/0026937 A1 | 3/2002 | Mault | |
| 2002/0055702 A1 | 5/2002 | Atala et al. | |
| 2002/0068365 A1 | 6/2002 | Kuhrts | |
| 2002/0138051 A1 | 9/2002 | Hole et al. | |
| 2002/0165179 A1 | 11/2002 | Baker, Jr. | |
| 2003/0009127 A1 | 1/2003 | Trescony et al. | |
| 2003/0039697 A1 | 2/2003 | Zhao et al. | |
| 2003/0073133 A1 | 4/2003 | Leyland-Jones | |
| 2003/0077243 A1 | 4/2003 | Fitzhugh et al. | |
| 2003/0093143 A1 | 5/2003 | Zhao et al. | |
| 2003/0165578 A1 | 9/2003 | Murrell | |
| 2003/0203915 A1 | 10/2003 | Fang et al. | |
| 2004/0009238 A1 | 1/2004 | Miller et al. | |
| 2004/0013747 A1 | 1/2004 | Tucker et al. | |
| 2004/0072360 A1 | 4/2004 | Naaman et al. | |
| 2004/0081580 A1 | 4/2004 | Hole et al. | |
| 2004/0087831 A1 | 5/2004 | Michels et al. | |
| 2004/0193218 A1 | 9/2004 | Butler | |
| 2004/0247640 A1 | 12/2004 | Zhao et al. | |
| 2005/0079148 A1 | 4/2005 | Fitzhugh et al. | |
| 2005/0136483 A1 | 6/2005 | Carlson | |
| 2005/0181026 A1 | 8/2005 | Davis et al. | |
| 2005/0197682 A1 | 9/2005 | Fox et al. | |
| 2005/0203069 A1 | 9/2005 | Arnold et al. | |
| 2005/0220838 A1 | 10/2005 | Zhao et al. | |
| 2005/0267090 A1 | 12/2005 | Mascharak | |
| 2006/0074282 A1 | 4/2006 | Ward et al. | |
| 2006/0134728 A1 | 6/2006 | MacDonald et al. | |
| 2006/0206171 A1 | 9/2006 | Gertner et al. | |
| 2006/0206173 A1 | 9/2006 | Gertner et al. | |
| 2006/0275350 A1 | 12/2006 | Davis et al. | |
| 2006/0280307 A1 | 12/2006 | Ikushima et al. | |
| 2007/0021382 A1 | 1/2007 | Assaf et al. | |
| 2007/0021800 A1 | 1/2007 | Whitehurst et al. | |
| 2007/0065473 A1 | 3/2007 | Miller | |
| 2007/0088316 A1 | 4/2007 | Stenzler et al. | |
| 2007/0148117 A1 | 6/2007 | Davis et al. | |
| 2007/0166357 A1 | 7/2007 | Shaffer et al. | |
| 2007/0181444 A1 | 8/2007 | Bernstein et al. | |
| 2007/0190122 A1 | 8/2007 | Davis et al. | |
| 2007/0208395 A1 | 9/2007 | Leclerc et al. | |
| 2007/0274874 A1 | 11/2007 | Miller et al. | |
| 2007/0298354 A1 | 12/2007 | Ding et al. | |
| 2008/0069863 A1 | 3/2008 | Peters | |
| 2008/0097282 A1 | 4/2008 | Hole et al. | |
| 2008/0220048 A1 | 9/2008 | Chen et al. | |
| 2008/0281383 A1 | 11/2008 | Butler | |
| 2008/0286321 A1 | 11/2008 | Reneker et al. | |
| 2008/0311163 A1 | 12/2008 | Peters | |
| 2009/0081279 A1 | 3/2009 | Jezek et al. | |
| 2009/0202617 A1 | 8/2009 | Ward et al. | |
| 2009/0204057 A1 | 8/2009 | Woo et al. | |
| 2009/0214618 A1 | 8/2009 | Schoenfisch et al. | |

| | | | |
|---|---|---|---|
| 2009/0214624 | A1 | 8/2009 | Smith et al. |
| 2010/0152683 | A1 | 6/2010 | Lindgren et al. |
| 2010/0197802 | A1 | 8/2010 | Jezek et al. |

FOREIGN PATENT DOCUMENTS

| | | |
|---|---|---|
| EP | 1 704 877 A1 | 9/2006 |
| WO | WO 92/09962 | 6/1992 |
| WO | WO 96/08966 A1 | 3/1996 |
| WO | WO 00/53193 | 9/2000 |
| WO | WO 01/10344 A1 | 2/2001 |
| WO | WO 02/17898 A2 | 3/2002 |
| WO | WO 02/057738 A2 | 7/2002 |
| WO | WO 03/086282 A2 | 10/2003 |
| WO | WO 2005/070008 A2 | 8/2005 |
| WO | WO 2005/112954 A1 | 12/2005 |
| WO | WO 2006/084912 A1 | 8/2006 |
| WO | WO 2006/095193 A2 | 9/2006 |
| WO | WO 2006/100155 A1 | 9/2006 |
| WO | WO 2006/107122 A1 | 10/2006 |
| WO | WO 2006/108420 A1 | 10/2006 |
| WO | WO 2007/130702 A2 | 11/2007 |
| WO | WO 2008/046211 A1 | 4/2008 |
| WO | WO 2009/131931 A1 | 10/2009 |
| WO | WO 03/006427 * | 1/2011 |

OTHER PUBLICATIONS

U.S. Appl. No. 12/930,351, Hyde et al.

Jamal, Sophie A. et al.; "Effect of Nitroglycerin Ointment on Bone Density and Strength in Postmenopausal Women"; JAMA; bearing a date of Feb. 23, 2011; pp. 800-807; vol. 305, No. 8; American Medical Association.

Khosla, Sundeep; "Is Nitroglycerin a Novel and Inexpensive Treatment for Osteoporosis?"; JAMA; bearing a date of Feb. 23, 2011; pp. 826-827; vol. 305, No. 8; American Medical Association.

Mims, Christopher; "Erectile Dysfunction Treatment to Save Soldiers' Lives"; Technology Review; bearing a date of Feb. 22, 2011; 2 pages; MIT; located at http://www.technologyreview.com/blog/mimssbits/26427/?p1=A5.

"Nanotechnology—the new Viagra?"; Nanowerk News; bearing a date of Apr. 26, 2009; p. 1; located at http://www.nanowerk.com/news/newsid=10273.php.

"A Method of Nitric Oxide Delivery for Healing and Organ Preservation"; University of Texas at Dallas; bearing a date of May 18, 2009; p. 1; located at http://utdallas,technologypublisher.com/TechnologyProject.aspx?id=2302.

"Nanotechnology bandage speeds up healing"; Nanowerk News; Source: Akron Beacon Journal (Paula Schleis); bearing a date of Dec. 15, 2006; pp. 1-2; printed on Jul. 14, 2009; located at http://www.nanowerk.com/news/newsid=1156.php.

Andrews, Karen L. et al.; "A Photosensitive Vascular Smooth Muscle Store of Nitric Oxide in Mouse Aorta: No Dependence on Expression of Endothelial Nitric Oxide Synthase"; British Journal of Pharmacology; 2003; pp. 932-940; vol. 138; Nature Publishing Group.

Bonaventura, Daniella et al.; "A Macrocyclic Nitrosyl Ruthenium Complex is a NO Donor that Induces Rat Aorta Relaxation"; Nitric Oxide; Mar. 2004; pp. 83-91 (p. 1); vol. 10, Issue 2; located at: http://www.sciencedirect.com; printed on Oct. 26, 2007 (Abstract Only).

Burrell, María A. et al.; "Detection of Nitric Oxide Synthase (NOS) in Somatostatin-Producing Cells of Human and Murine Stomach and Pancreas"; The Journal of Histochemistry and Cytochemistry; 1996; pp. 339-346; vol. 44, No. 4; The Histochemical Society, Inc.

Chmura, Antonina et al.; "The Role of Photoinduced Electron Transfer Processes in Photodegradation of the $[Fe_4(\mu 3-S)_3(NO)_7]^-$ Cluster"; Nitric Oxide; Dec. 2006; pp. 370-379 (p. 1); vol. 15, Issue 4; located at: http://www.sciencedirect.com; printed on Oct. 26, 2007 (Abstract Only).

Chen, X; Gillis, CN; "Methylene Blue Enhanced Photorelaxation in Aorta, Pulmonary Artery and Corpus Cavernosum"; Biochem. Biophys. Res. Commun.; Jan. 29, 1993; pp. 559-563 (pp. 1-2); vol. 190, No. 2; located at: http://www.pubmed.gov; printed on Oct. 26, 2007 (Abstract Only).

Dujić, Željko et al; "Aerobic Exercise Before Diving Reduces Venous Gas Bubble Formation in Humans"; J. Physiol.; 2004; pp. 637-642; vol. 555.3; The Physiological Society.

"Easy Life II"; Photon Technology International; pp. 1-3; located at: http://www.pti-nj.com/EasyLife/easylife.html; printed on Oct. 6, 2007.

Ferezin, Camila Z. et al; "The Complex Trans-$[RuCl([15]aneN_4)NO]^{2+}$ Induces Rat Aorta Relaxation by Ultraviolet Light Irradiation"; Nitric Oxide; Nov. 2005; pp. 170-175 (p. 1); vol. 13, Issue 3; located at: http://www.sciencedirect.com; printed on Oct. 26, 2007 (Abstract Only).

Flitney, FW et al.; "Iron-Sulphur Cluster Nitrosyls, a Novel Class of Nitric Oxide Generator: Mechanism of Vasodilator Action on Rat Isolated Tail Artery"; Br. J. Pharmacol.; Nov. 1992; pp. 842-848 (pp. 1-2); vol. 107, No. 3; located at: http://www.pubmed.gov; printed on Oct. 26, 2007 (Abstract Only).

Flitney, Frederick Werner; Megson, Ian L.; "Nitric Oxide and the Mechanism of Rat Vascular Smooth Muscle Photorelaxation"; J. Physiol.; 2003; pp. 819-828; vol. 550.3; The Physiological Society.

Flitney, FW et al.; "Vasodilator Responses of Rat Isolated Tail Artery Enhanced by Oxygen-Dependent, Photochemical Release of Nitric Oxide from Iron-Sulphur-Nitrosyls"; Br. J. Pharmacol.; Apr. 1996; pp. 1549-1557 (pp. 1-2); vol. 117, No. 7; located at: http://www.pubmed.gov; printed on Oct. 26, 2007 (Abstract Only).

Fukuhara, Kiyoshi et al.; "Photochemical Generation of Nitric Oxide from 6-Nitrobenzo[α]pyrene"; J. Am. Chem. Soc.; 2001; pp. 8662-8666 (p. 1); vol. 123, No. 36; located at: http://pubs.acs.org/cgi-bin/abstract.cgi/jacsat/2001/123/i36/abs/ja0109038.html; printed on Oct. 26, 2007 (Abstract Only).

Gaston, Benjamin; "Summary: Systemic Effects of Inhaled Nitric Oxide"; Proceedings of the American Thoracic Society; 2006; pp. 170-172; vol. 3.

Gau, Jen-Jr et al.; "A MEMS Based Amperometric Detector for E. coli Bacteria Using Self-Assembled Monolayers"; Biosensors & Bioelectronics; 2001; pp. 745-755; vol. 16; Elsevier Science B.V.

Hardwick, J.B.J. et al.; "A Novel Method for the Delivery of Nitric Oxide Therapy to the Skin of Human Subjects Using a Semi-Permeable Membrane"; Clinical Science; 2001; pp. 395-400; vol. 100; The Biochemical Society and the Medical Research Society.

Hattenbach, Lars-Olof et al.; "Detection of Inducible Nitric Oxide Synthase and Vascular Endothelial Growth Factor in Choroidal Neovascular Membranes"; Ophthalmologica; 2002; pp. 209-214; vol. 216; S. Karger AG, Basel.

Hou, Yongchun et al.; "Nanomolar Scale Nitric Oxide Generation from Self-Assembled Monolayer Modified Gold Electrodes"; Chem. Commun.; 2000; pp. 1831-1832; The Royal Society of Chemistry.

Hrabie, Joseph A.; Keefer, Larry K.; "Chemistry of the Nitric Oxide-Releasing Diazeniumdiolate ("Nitrosohydroxylamine") Functional Group and Its Oxygen-Substituted Derivatives"; Chem. Rev.; 2002; pp. 1135-1154; vol. 102; American Chemical Society.

Ikeda, Osamu et al.; "Nitric Oxide Detection with Glassy Carbon Electrodes Coated with Charge-Different Polymer Films"; Sensors; Apr. 26, 2005; pp. 161-170; vol. 5; ISSN 1424-8220; MDPI.

"InNo-T Nitric Oxide Measurement System"; Warner Instruments; Bearing dates of 1998-2007; pp. 1-2; located at: http://www.warneronline.com/product_info.cfm?ID=220; printed on Oct. 24, 2007.

Keefer, Larry K.; "Nitric Oxide-Releasing Compounds: From Basic Research to Promising Drugs"; Chemtech; Aug. 1998; pp. 30-35 (pp. 1-8); vol. 28, No. 8; located at: http://pubs.acs.org/hotartcl/chemtech/98/aug/nitric.html; printed on Oct. 2, 2007; The American Chemical Society.

Khan, Ma et al.; "The Effect of Superoxide Dismutase on Nitric Oxide-Mediated and Electrical Field-Stimulated Diabetic Rabbit Cavernosal Smooth Muscle Relaxation"; BJU Int.; Jan. 2001; pp. 98-103 (p. 1); vol. 87, No. 1; located at: http://www.pubmed.gov; printed on Sep. 27, 2007 (Abstract Only).

Kim, SC et al.; "Effects of Ultraviolet Light on the Tension of Isolated Human Cavernosal Smooth Muscle from Non-Diabetic and Diabetic Impotent Men"; Urol. Res.; 1997; pp. 149-152 (p. 1); vol. 25, No. 2; located at http://www.pubmed.gov; printed on Sep. 27, 2007 (Abstract Only).

Kim, JH et al; "Mechanism of UV Light-Induced Photorelaxation in Isolated Rat Aorta"; J. Vet. Sci.; Dec. 2000; pp. 81-86 (p. 1); vol. 1, No. 2; located at: http://www.pubmed.gov; printed on Oct. 26, 2007 (Abstract Only).

Li, Chang Ming et al.; "Electrochemical Detection of Nitric Oxide on a SWCNT/RTIL Composite Gel Microelectrode"; Electroanalysis; 2006; pp. 713-718; vol. 18, No. 7; Wiley-VCH Verlag GmbH & Co. KGaA, Weinheim.

"Light-Emitting Diode (LED)"; Fiber Optics; Bearing a date of 2005; pp. 1-10; located at: http://www.fiber-optics.info/articles/LEDs.htm; printed on Oct. 6, 2007.

Lin, Hong-Yu et al.; "Side-Polished Multimode Fiber Biosensor Based on Surface Plasmon Resonance with Halogen Light"; Applied Optics; Feb. 10, 2007; pp. 800-806; vol. 46, No. 5; Optical Society of America.

Matthews, EK et al.; "Photon Pharmacology of an Iron-Sulphur Cluster Nitrosyl Compound Acting on Smooth Muscle"; Br. J. Pharmacol.; Sep. 1994; pp. 87-94 (p. 1); vol. 113, No. located at: http://www.pubmed.gov; printed on Oct. 26, 2007 (Abstract Only).

Mendioroz, A. et al.; "Infrared to Visible and Ultraviolet Upconversion Processes in $Nd_{3+}$-Doped Potassium Lead Chloride Crystal"; Optical Materials; Sep. 2004; pp. 351-357 (p. 1); vol. 26, Issue 4; located at: http://www.sciencedirect.com; printed on Oct. 29, 2007 (Abstract Only).

Nablo, Brian J. et al.; "Inhibition of Implant-Associated Infections Via Nitric Oxide Release"; Biomaterials; Dec. 2005; pp. 6984-6990 (p. 1); vol. 26, Issue 34; located at: http://www.sciencedirect.com; printed on Oct. 26, 2007 (Abstract Only).

"NO Electrodes"; WPI-Europe-Biosensing-NO Electrodes; Bearing a date of Nov. 29, 2007; pp. 1-5; World Precision Instruments; located at: http://www.wpi-europe.com/products/biosensing/noelectrodes.htm; printed on Nov. 29, 2007.

"OL 770-LED: High-Speed LED Measurement System"; Bearing a date of 2001; pp. 1-6; located at: http://www.optroniclabs.com; Optronic Laboratories, Inc.

"Particulate Effects on Immunologic Function"; OST 1997AR; Bearing a date of 1997; pp. 1-2; located at: http://www.fda.gov/cdrh/ost/rpt97/OST1997AR9.HTML; printed on Oct. 16, 2007.

Peng, H. et al.; "Ultraviolet Light-Emitting Diodes Operating in the 340 nm Wavelength Range and Application to Time-Resolved Fluorescence Spectroscopy"; Applied Physics Letters; Aug. 23, 2004; pp. 1436-1438 (p. 1); vol. 85, Issue 8; located at: http://scitation.aip.org; printed on Oct. 26, 2007 (Abstract Only).

Pou, SJ et al.; "Biological Studies of a Nitroso Compound that Releases Nitric Oxide Upon Illumination"; Molecular Pharmacology; Oct. 1, 1994; pp. 709-715 (p. 1); Vo. 46, Issue 4; located at: http://molpharm.aspetjournals.org/cgi/content/abstract/46/4/709; printed on Oct. 26, 2007 (Abstract Only).

"Probes for Nitric Oxide (NO) Research"; EMD-Calbiochem: Nitric Oxide Probes; Bearing a date of 2007; pp. 1-2; Calbiochem, Novabiochem, & Novagen; located at: http://www.emdbiosciences.com/html/cbc/nitric_oxide_probes.htm; printed on Nov. 29, 2007.

Räthel, Thomas R. et al.; "Application of 4,5-Diaminofluorescein to Reliably Measure Nitric Oxide Released from Endothelial Cells in Vitro"; Biological Procedures Online; Jun. 2, 2003; pp. 136-142; vol. 5, No. 1.

Rotta, J.C.G. et al.; "Nitric Oxide Release from the S-Nitrosothiol Zinc Phthalocyanine Complex by Flash Photolysis"; Brazilian Journal of Medical and Biological Research; 2003; pp. 587-594; vol. 36, No. 5; located at: http://www.scielo.br/pdf/bjmbr/v36n5/4604.pdf.

Seo, K.K. et al.; "Synergistic Effects of Sildenafil on Relaxation of Rabbit and Rat Cavernosal Smooth Muscles when Combined with Various Vasoactive Agents"; BJU International; 2001; pp. 596-601; vol. 88.

Singh, Ravinder Jit et al.; "Photosensitized Decomposition of S-Nitrosothiols and 2-Methyl-2-Nitrosopropane Possible Use for Site-Directed Nitric Oxide Production"; FEBS Letters; 1995; pp. 47-51; vol. 360; Federation of European Biochemical Societies.

Smith, DJ et al.; "Nitric Oxide-Releasing Polymers Containing the [N(O)NO]-Group"; J. Med. Chem.; Mar. 1, 1996; pp. 1148-1156 (p. 1); vol. 39, No. 5; located at: http://www.pubmed.gov; printed on Oct. 26, 2007 (Abstract Only).

Sonoki, T. et al.; "Detection of Inducible Nitric Oxide Synthase (iNOS) mRNA by RT-PCR in ATL Patients and HTLV-1 Infected Cell Lines: Clinical Features and Apoptosis by NOS Inhibitor"; Leukemia; 1999; pp. 713-718; vol. 13; Stockton Press.

Wadsworth, Roger et al.; "Physiologically Relevant Measurements of Nitric Oxide in Cardiovascular Research Using Electrochemical Microsensors"; Journal of Vascular Research; 2006; pp. 70-85; vol. 43; S. Karger AG, Basel.

Wang, Peng George et al.; "Nitric Oxide Donors: Chemical Activities and Biological Applications"; Chem. Rev.; 2002; pp. 1091-1134 (pp. 1-53); vol. 102, No. 4; American Chemical Society; located at: http://pubs.acs.org/cgi-bin/abstract.cgi/chraey/2002/102/i04/abs/cr0000401.html; printed on Oct. 26, 2007.

Wang, Tianlong et al.; "Inhaled Nitric Oxide in 2003: A Review of its Mechanisms of Action"; Canadian Journal of Anesthesia; 2003; pp. 839-846; vol. 50, No. 8.

Williamson, David; "Study: Nitric Oxide-Releasing Materials Might Reduce Medical Implant Infections"; UNC News Services; Sep. 7, 2001; pp. 1-2; No. 416; located at: http://www.unc.edu/news/archives/sep01/schoen090701.htm; printed on Oct. 4, 2007.

Xie, Rong-Jun; "Highly Efficient White-Light-Emitting Diodes Fabricated with Short-Wavelength Yellow Oxynitride Phosphors"; Applied Physics Letters; Mar. 6, 2006; pp. 101104.1-101104.3 (pp. 1-2); vol. 88; located at: http://scitation.aip.org/; printed on Oct. 26, 2007 (Abstract Only).

Birkeland et al.; "On the Oxidation of Atmospheric Nitrogen in Electric Arcs"; Nature; bearing a date of 1898; pp. 98-116; No. 1,506, vol. 58.

Levine et al.; "A New, Highly Efficient Red-Emitting Cathodoluminescent Phosphor ($YVO_4$:Eu) For Color Television"; Applied Physics Letters; bearing a date of Sep. 15, 1964; pp. 1-3; vol. 5, No. 6.

Mellor, J. W.; "Modern Inorganic Chemistry"; excerpt from Modern Inorganic Chemistry; bearing a date of 1912; pp. 1-19; Longmans, Greene, and Co.

"The Shadow Mask and Aperture Grill"; The PC Guide; bearing a date of Apr. 17, 2001; pp. 1-3; © Copyright 1997-2004 Charles M. Kozierok; printed Oct. 6, 2009; located at http://www.pcguide.com/ref/crt/crtMask-c.html.

U.S. Appl. No. 12/928,029, Hyde et al.
U.S. Appl. No. 12/928,028, Hyde et al.
U.S. Appl. No. 12/927,610, Hyde et al.
U.S. Appl. No. 12/008,708, Hyde et al.
U.S. Appl. No. 12/008,694, Hyde et al.
U.S. Appl. No. 12/006,090, Hyde et al.
U.S. Appl. No. 12/006,069, Hyde et al.
U.S. Appl. No. 12/006,049, Hyde et al.
U.S. Appl. No. 12/005,170, Hyde et al.
U.S. Appl. No. 12/005,136, Hyde et al.
U.S. Appl. No. 12/005,132, Hyde et al.
U.S. Appl. No. 12/005,065, Hyde et al.
U.S. Appl. No. 12/005,045, Hyde et al.

Graham-Rowe, Duncan; "Photonic Fabrics Take Shape"; Nature Photonics; Jan. 2007; pp. 6-7; vol. 1; Nature Publishing Group.

Liu et al.; "Novel Delivery System for the Bioregulatory Agent Nitric Oxide"; Chemistry of Materials; bearing a date of 2009; pp. 5032-5041; vol. 21, No. 21; ©2009 American Chemical Society.

"Nitric oxide-releasing wrap for donor organs and cloth for therapeutic socks"; e! Science News; bearing a date of Jan. 6, 2010; pp. 1-2; located at http://esciencenews.com/articles/2010/01/06/nitric.oxide.releasing.wrap.donor.organs.and.cloth.therapeutic.socks; printed on Jan. 19, 2010.

U.S. Appl. No. 12/148,284, Hyde et al.
U.S. Appl. No. 12/148,283, Hyde et al.

Butler, P. et al.; "Cell Transplantation from Limb Allografts"; Plastic and Reconstructive Surgery; Bearing a date of Jul. 1998; pp. 161-168 (11 total pages); vol. 102, No. 1; American Society of Plastic Surgeons; located at: http://www.plasreconsurg.com; printed on Apr. 25, 2008.

Butler, A.R.; Nicholson, R.; *Life, Death and Nitric Oxide*; Bearing a date of Oct. 17, 2003; 1$^{st}$ edition; Royal Society of Chemistry; ISBN 978-0854046867 (Not Provided).

De Lima, R.G. et al.; "Controlled Nitric Oxide Photo-Release From Nitro Ruthenium Complexes: The Vasodilator Response Produced by UV Light Irradiation"; Inorganica Chimica Acta; Bearing a date of 2005; pp. 2643-2650; vol. 358; Elsevier B.V.; located at: http://www.sciencedirect.com.

Frank, S. et al.; "Nitric Oxide Triggers Enhanced Induction of Vascular Endothelial Growth Factor Expression In Cultured Keratinocytes (HaCaT) and During Cutaneous Wound Repair"; The FASEB Journal; Bearing a date of 1999; pp. 2002-2014; vol. 13.

Ghaffari, A. et al.; "A Direct Nitric Oxide Gas Delivery System for Bacterial and Mammalian Cell Cultures"; Nitric Oxide; Bearing a date of 2005; pp. 129-140; vol. 12; Elsevier Inc.; located at: http://www.sciencedirect.com.

Ghaffari, A. et al.; "Efficacy of Gaseous Nitric Oxide in the Treatment of Skin and Soft Tissue Infections"; Wound Repair and Regeneration; Bearing a date of 2007; pp. 368-377; vol. 15; Wound Healing Society.

Ghaffari, A. et al.; "Potential Application of Gaseous Nitric Oxide as a Topical Antimicrobial Agent"; Nitric Oxide; Bearing a date of 2006; pp. 21-29; vol. 14; Elsevier Inc.; located at: http://www.sciencedirect.com.

Goldsmith, P.C. et al.; "Inhibitors of Nitric Oxide Synthase in Human Skin"; The Journal of Investigative Dermatology; Bearing a date of Jan. 1996; pp. 113-118; vol. 106, No. 1; The Society for Investigative Dermatology, Inc.

Govers, R.; Rabelink, T.J.; "Cellular Regulation of Endothelial Nitric Oxide Synthase"; Am. J. Physiol. Renal. Physiol.; Bearing a date of 2001; pp. F193-F206; vol. 280; The American Physiological Society; located at: http://www.ajprenal.org.

Guo, H.; "Two-and Three-Photon Upconversion of LaOBr:$Er^{3+}$"; Optical Materials; Bearing a date of 2007; pp. 1840-1843; vol. 29; Elsevier B.V.; located at: http://www.sciencedirect.com.

Hassett, D.J.; Imlay, J.A.; "Bactericidal Antibiotics and Oxidative Stress: A Radical Proposal"; ACS Chemical Biology; Bearing a date of 2007; pp. 708-710; vol. 2, No. 11; located at: http://www.acschemicalbiology.org.

Miller, C.C. et al.; "Treatment of Chronic Nonhealing Leg Ulceration with Gaseous Nitric Oxide: A Case Study"; Journal of Cutaneous Medicine and Surgery; Bearing a date of Aug. 2004; pp. 233-238; vol. 8, No. 4.

Pacher, P. et al.; "Nitric Oxide and Peroxynitrite in Health and Disease"; Physiol. Rev.; Bearing a date of Jan. 2007; pp. 315-424; vol. 87; The American Physiological Society; located at: http://www.prv.org.

Patel, D.N. et al.; "Spectroscopic and Two-Photon Upconversion Studies of $Ho^{3+}$-Doped $Lu_3Al_5O_{12}$"; Optical Materials; Bearing a date of Jul. 1998; pp. 225-234; vol. 10; Elsevier Science B.V.

Rapaport, A. et al.; "Review of the Properties of Up-Conversion Phosphors for New Emissive Displays"; Journal of Display Technology; Bearing a date of Mar. 2006; pp. 68-78; vol. 2, No. 1; IEEE.

Roméro-Graillet, C. et al.; "Nitric Oxide Produced by Ultraviolet-Irradiated Keratinocytes Stimulates Melanogenesis"; J. Clin. Invest.; Bearing a date of Feb. 1997; pp. 635-642; vol. 99, No. 4; The American Society of Clinical Investigation, Inc.

Seabra, A.B. et al.; "S-Nitrosoglutathione Incorporated in Poly(Ethylene Glycol) Matrix: Potential Use for Topical Nitric Oxide Delivery"; Nitric Oxide; Bearing a date of 2004; pp. 263-272; vol. 11; Elsevier Inc.; located at: http://www.sciencedirect.com.

Shabani, M. et al.; "Enhancement of Wound Repair with a Topically Applied Nitric Oxide-Releasing Polymer"; Wound Repair and Regeneration; Bearing dates of Jul.-Sep. 1996; pp. 353-362; vol. 4, No. 3; The Wound Healing Society.

Sussman, C.; Wound Care: A Collaborative Practice Manual; Bearing a date of Jan. 2007; ISBN 0781774446 (Not Provided).

Suzuki, H.; Hewitt, C.W.; "Cell Transplantation from Limb Allografts: Discussion"; Plastic and Reconstructive Surgery; Bearing a date of Jul. 1998; pp. 169-170 (2 total pages); vol. 102, No. 1; American Society of Plastic Surgeons; located at: http://www.plasreconsurg.com; printed on May 2, 2008.

Tamir, S.; Tannenbaum, S.R.; "The Role of Nitric Oxide (NO) in the Carcinogenic Process"; Biochimica et Biophysica Acta; Bearing a date of 1996; pp. F31-F36; vol. 1288; Elsevier Science B.V.

Tu, H. et al.; "A Novel Electrochemical Microsensor for Nitric Oxide Based on Electropolymerized Film of o-Aminobenzaldehyde-Ethylene-Diamine Nickel"; Electroanalysis; Bearing a date of 1999; pp. 70-74; vol. 11, No. 1; Wiley-VCH.

Van Faassen, E., Vanin, A. (Eds); Radicals for Life: The Various Forms of Nitric Oxide; Bearing a date of Mar. 2007; 442 pages; ISBN 978-0-444-52236-8; Elsevier (Not Provided).

Weller, R. et al.; "Antimicrobial Effect of Acidified Nitrite on Dermatophyte Fungi, Candida and Bacterial Skin Pathogens"; Journal of Applied Microbiology; Bearing a date of 2001; pp. 648-652; vol. 90; The Society for Applied Microbiology.

Weller, R. et al.; "Nitric Oxide Is Generated on the Skin Surface by Reduction of Sweat Nitrate"; The Journal of Investigative Dermatology; Bearing a date of Sep. 1996; pp. 327-331; vol. 107, No. 3; The Society of Investigative Dermatology, Inc.

Yamasaki, K. et al.; "Reversal of Impaired Wound Repair in iNOS-Deficient Mice by Topical Adenoviral-Mediated iNOS Gene Transfer"; J. Clin. Invest.; Bearing a date of Mar. 1998; pp. 967-971; vol. 101, No. 5; The American Society for Clinical Investigation, Inc.; located at: http://www.jci.org.

Zhelyaskov, V.R.; Godwin, D.W.; "Photolytic Generation of Nitric Oxide Through a Porous Glass Partitioning Membrane"; Nitric Oxide: Biology and Chemistry; Bearing a date of 1998; pp. 454-459; vol. 2, No. 6; Article No. NO980195; Academic Press.

\* cited by examiner

210 one or more photolyzable nitric oxide donors

- 302 one or more photolyzable nitric oxide donors that include one or more diazeniumdiolates
- 304 one or more photolyzable nitric oxide donors that are associated with one or more quantum dots
- 306 one or more photolyzable nitric oxide donors that are associated with one or more optical fibers
- 308 one or more photolyzable nitric oxide donors that are associated with one or more fluorescent materials
- 310 one or more photolyzable nitric oxide donors that are associated with one or more rare-earth materials
- 312 one or more photolyzable nitric oxide donors that are associated with one or more rare-earth materials that facilitate upconversion of energy
- 314 one or more photolyzable nitric oxide donors that are coupled to one or more polymeric materials

220 one or more light sources that are physically associated with the one or more photolyzable nitric oxide donors

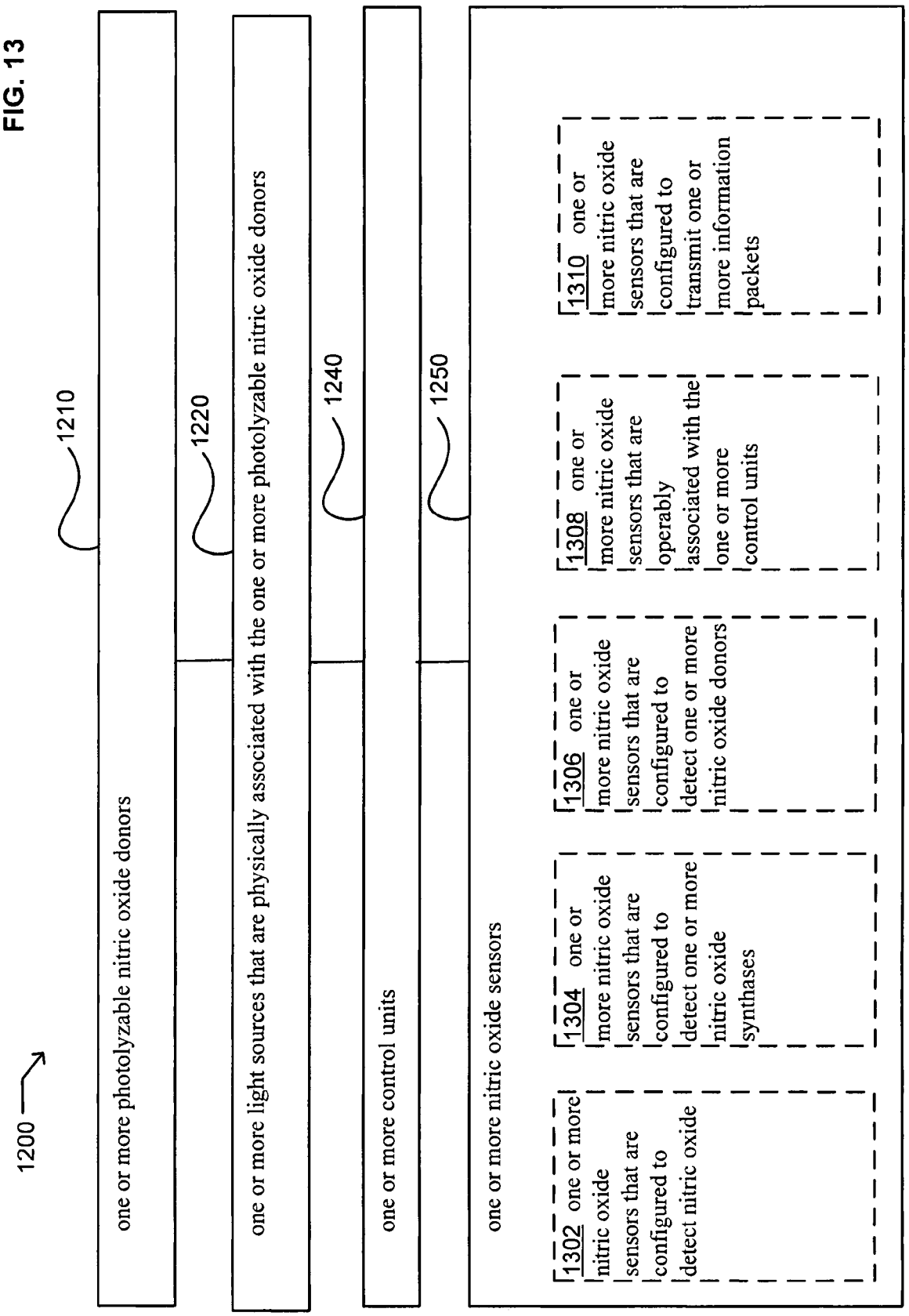

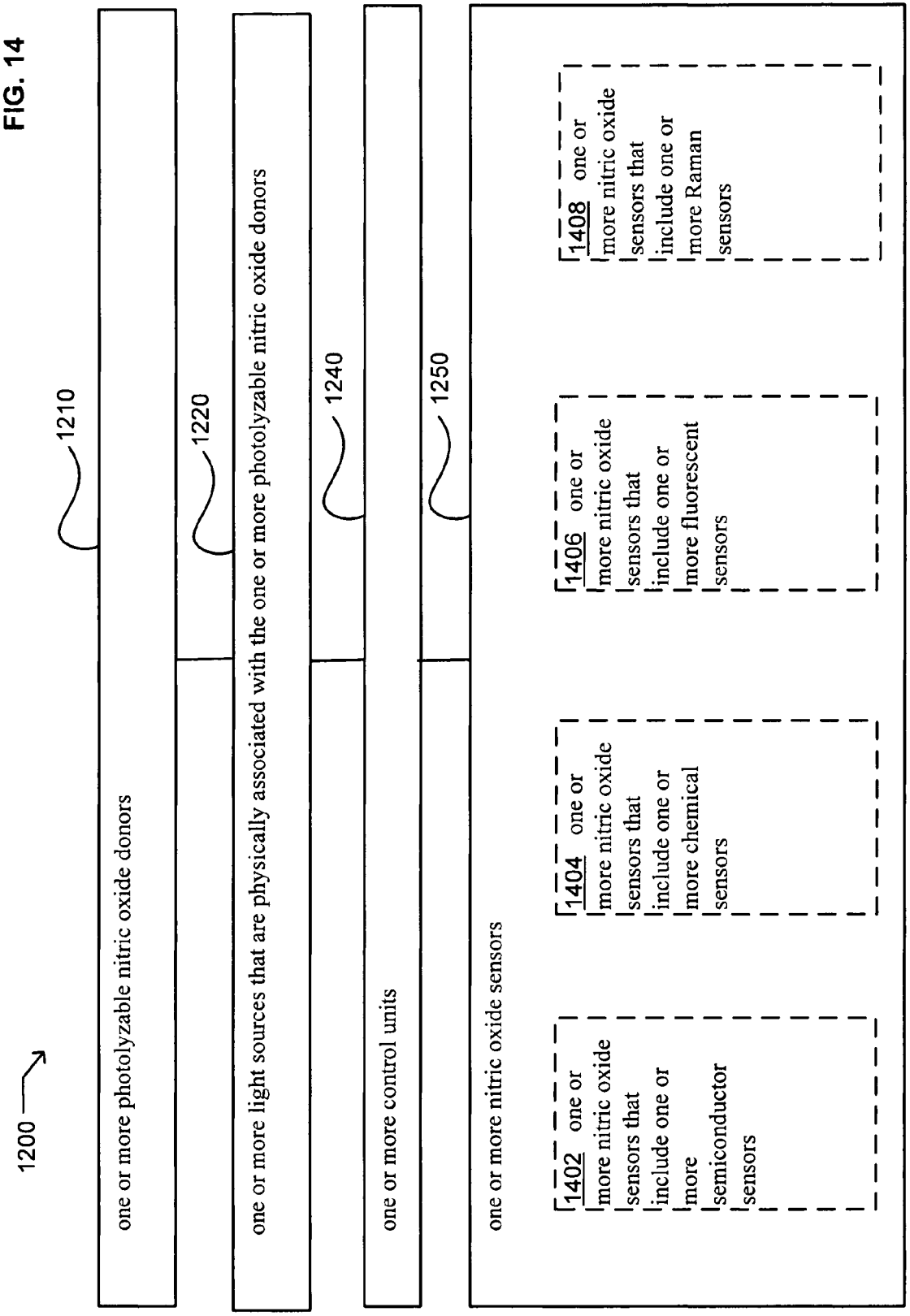

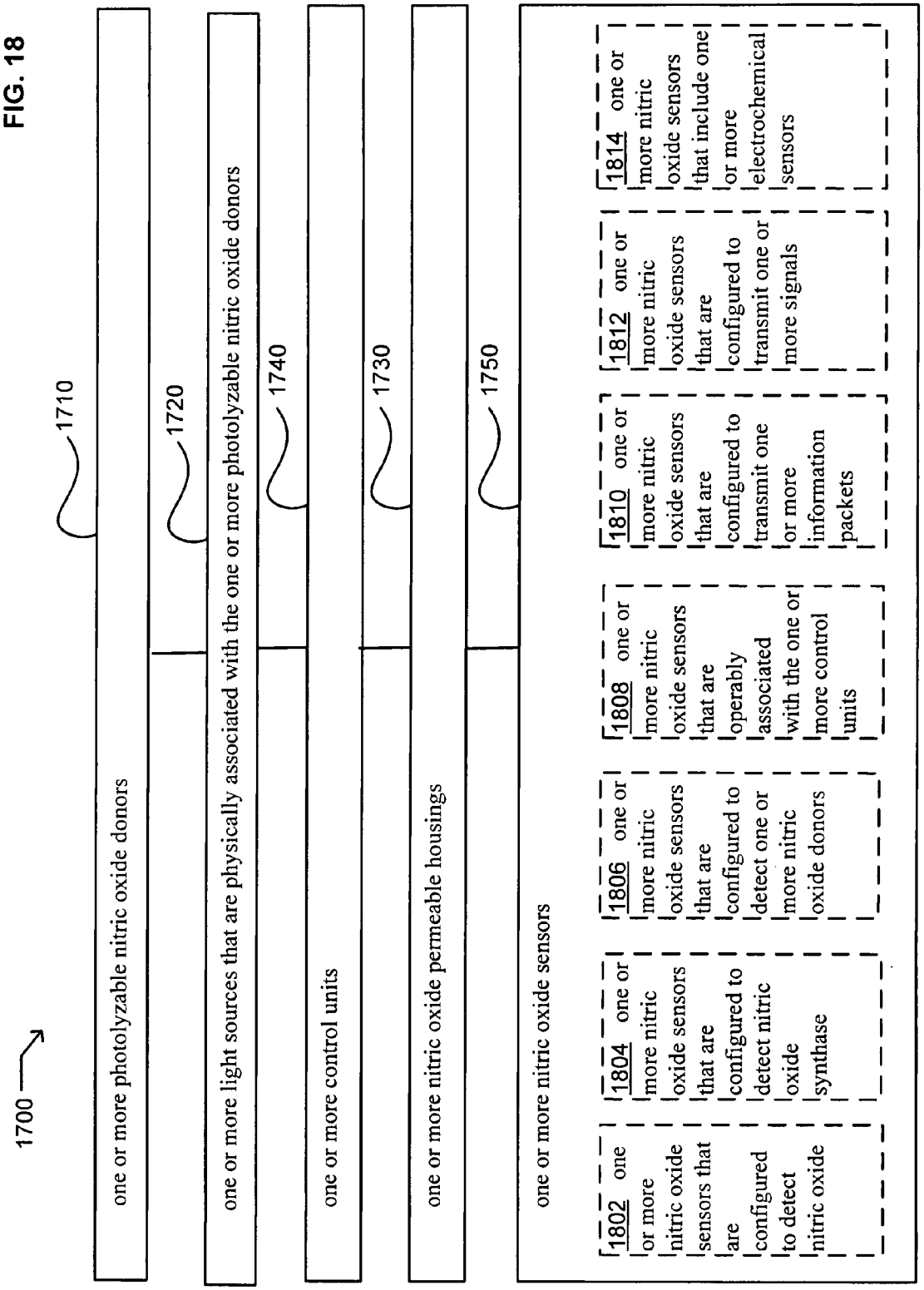

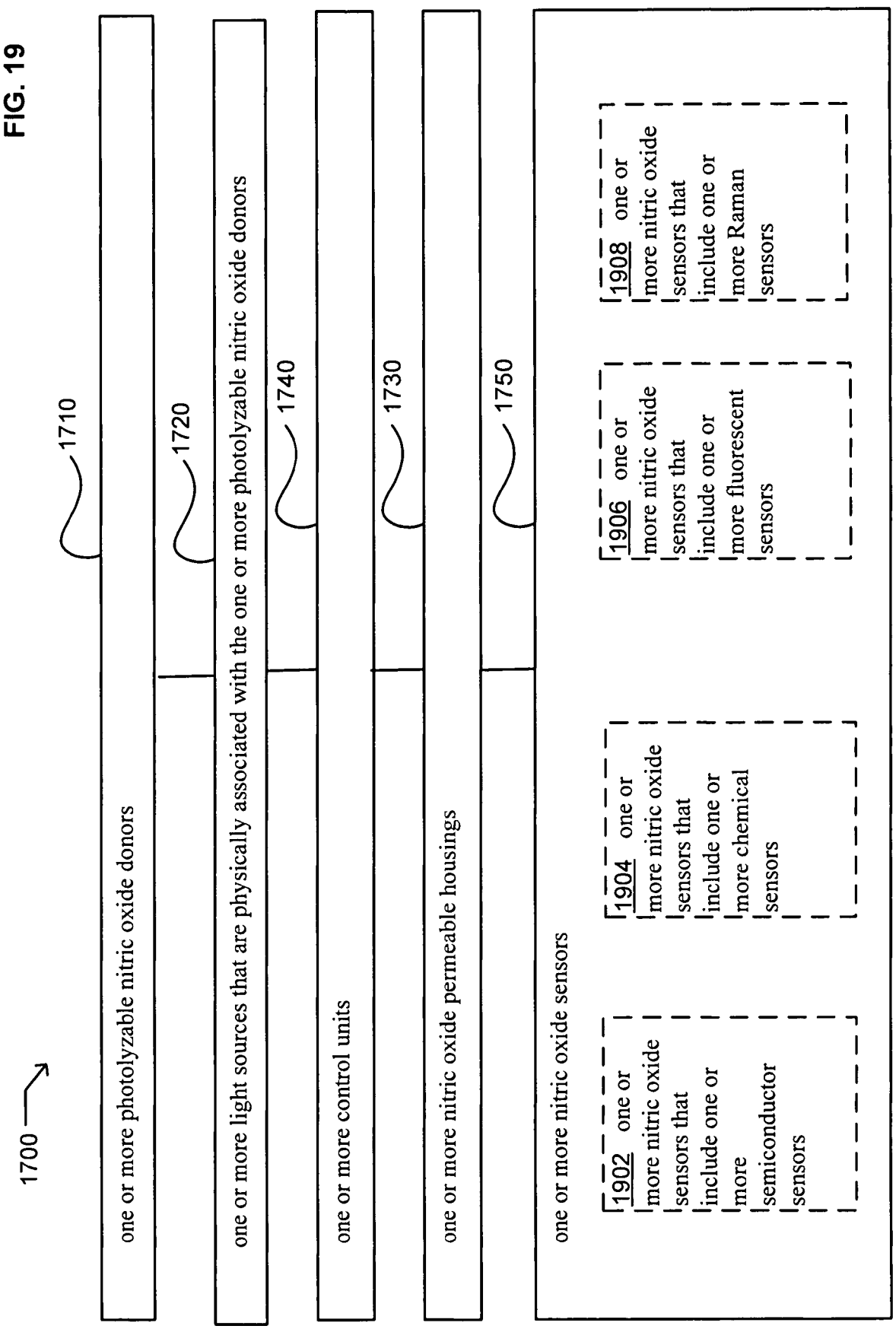

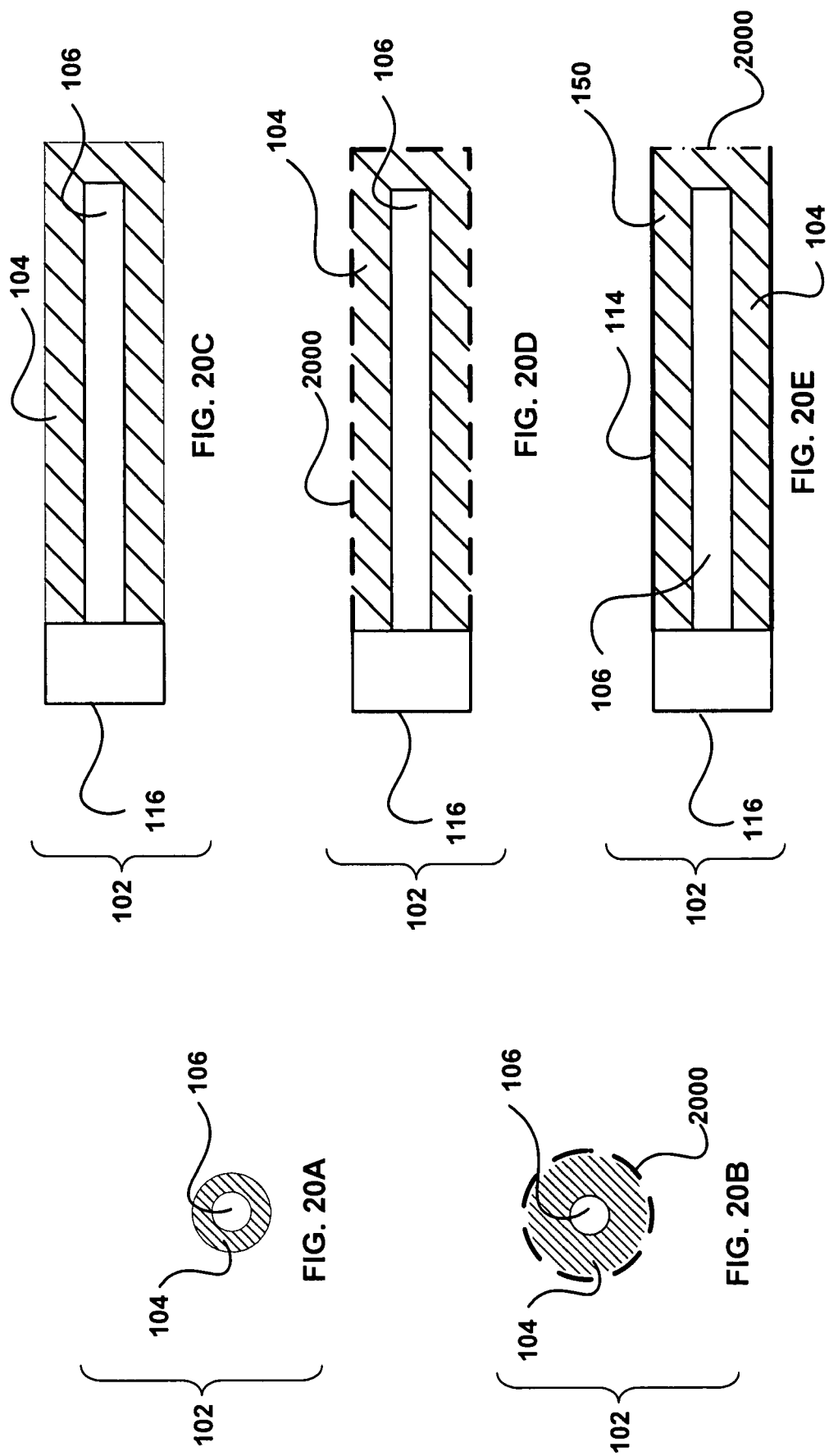

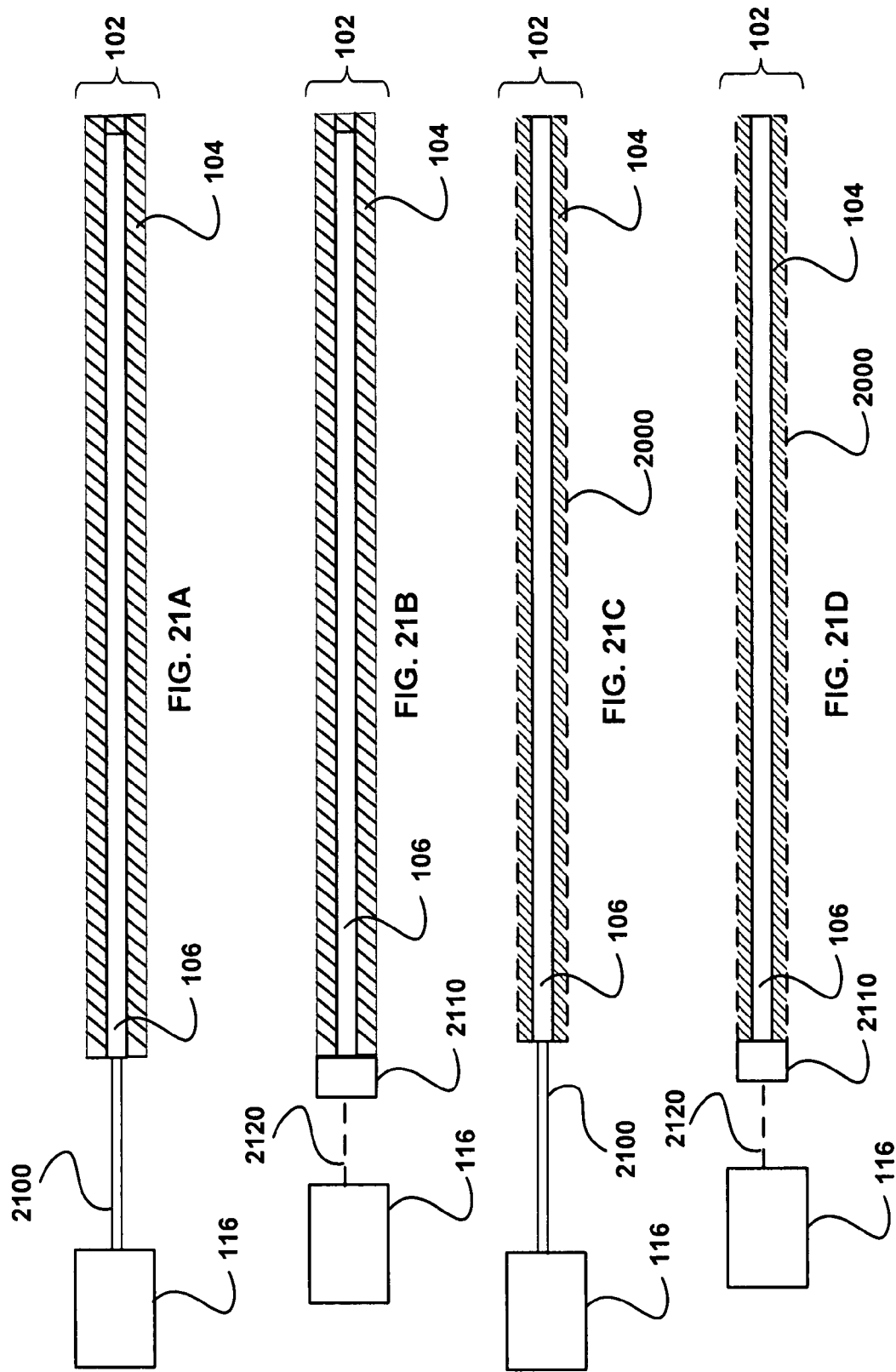

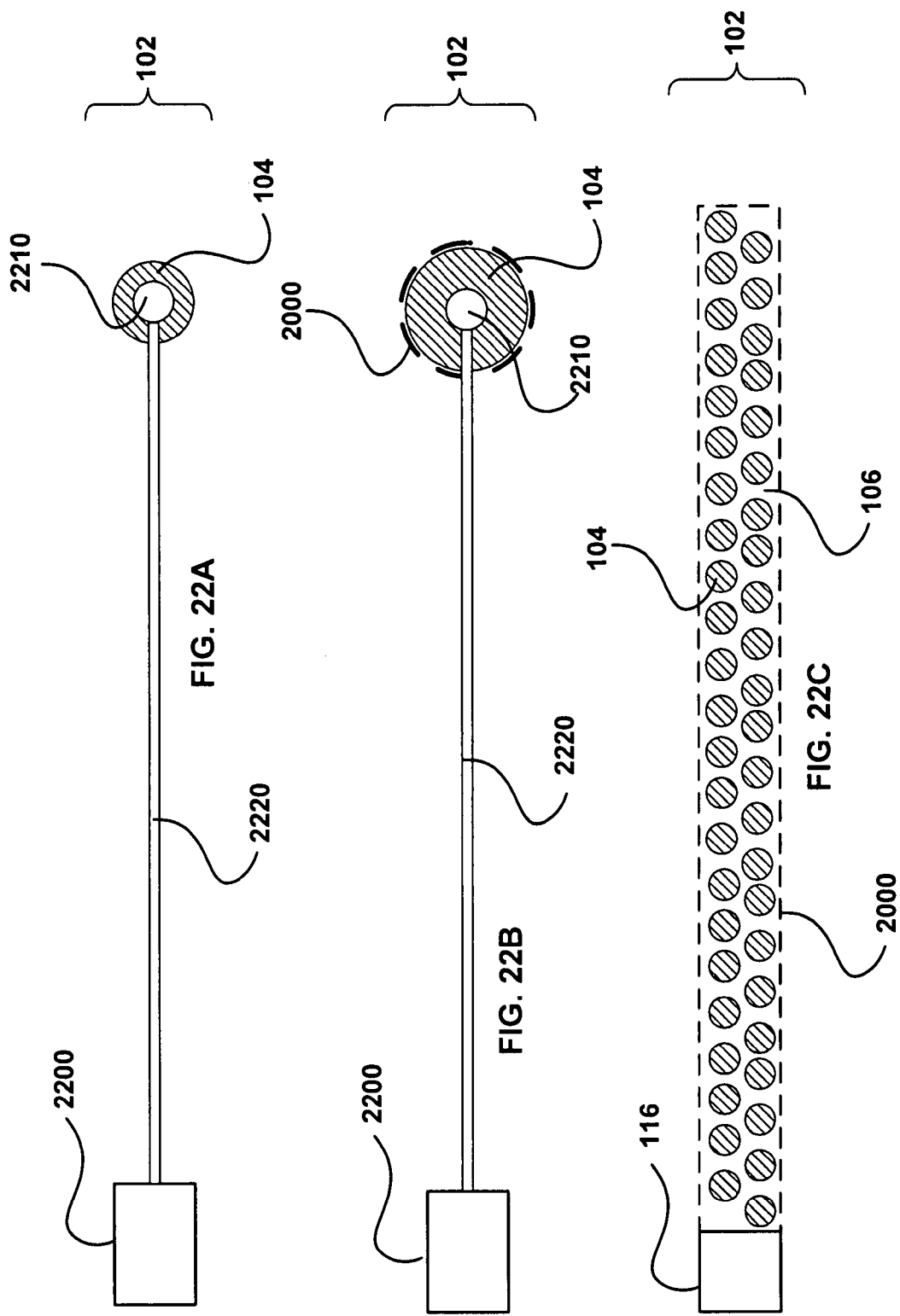

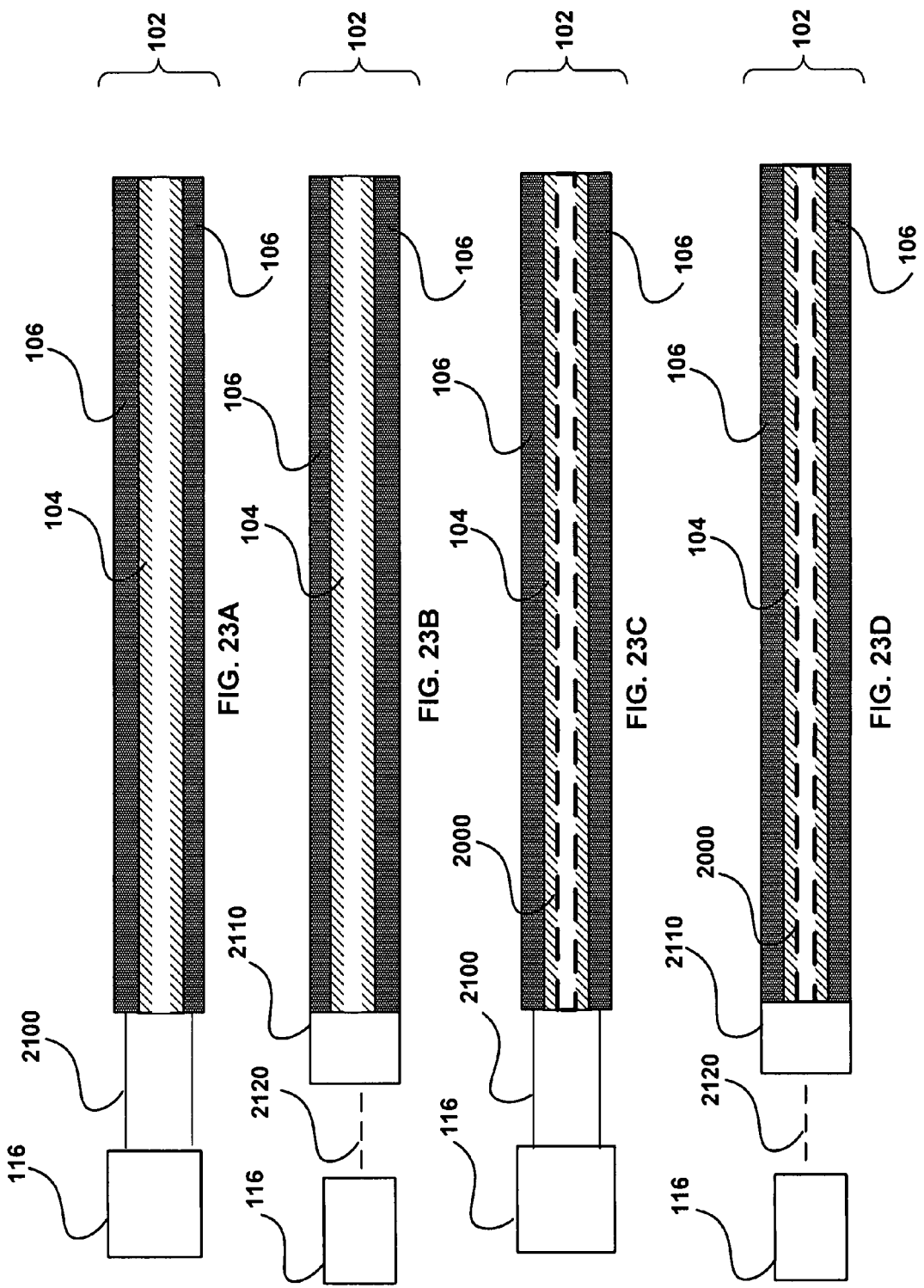

FIGS. 24A-24C
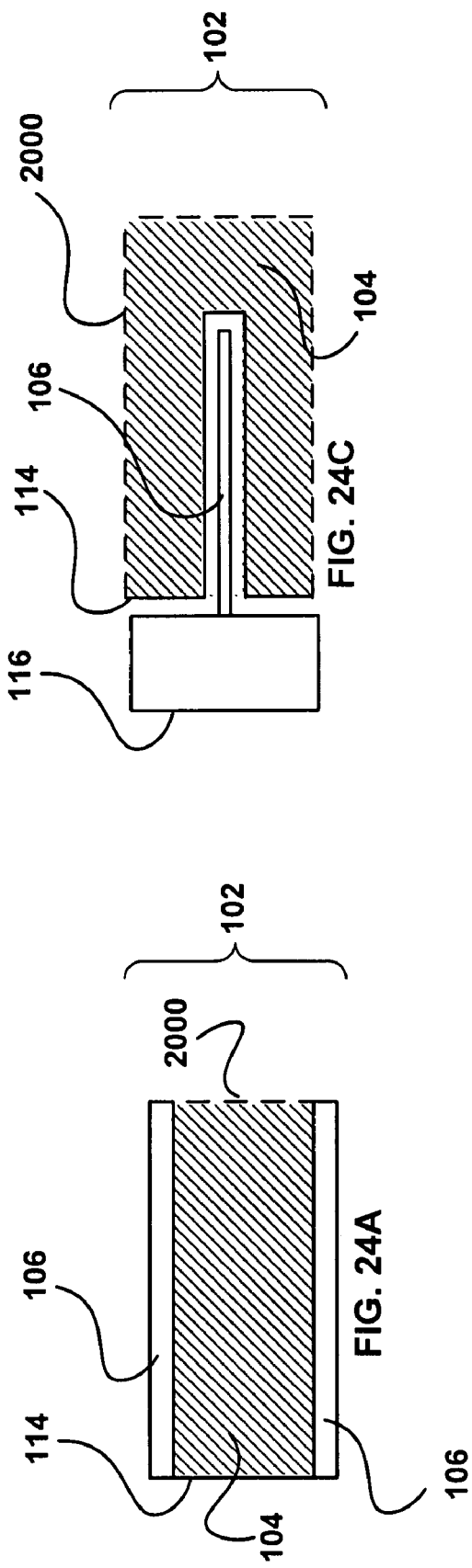
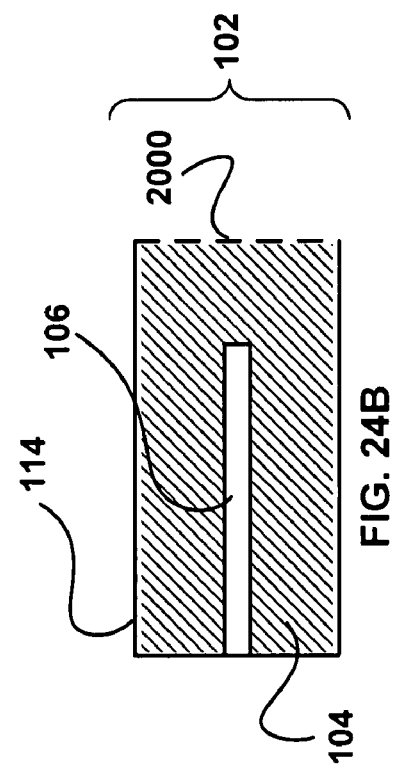

FIGS. 25A-25C
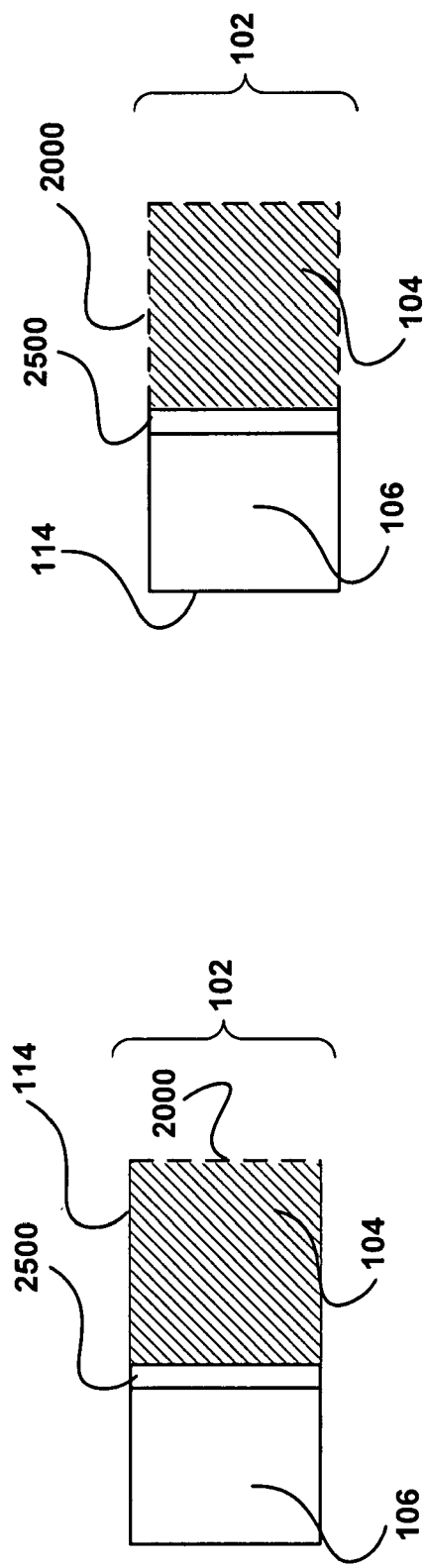
FIG. 25A
FIG. 25B
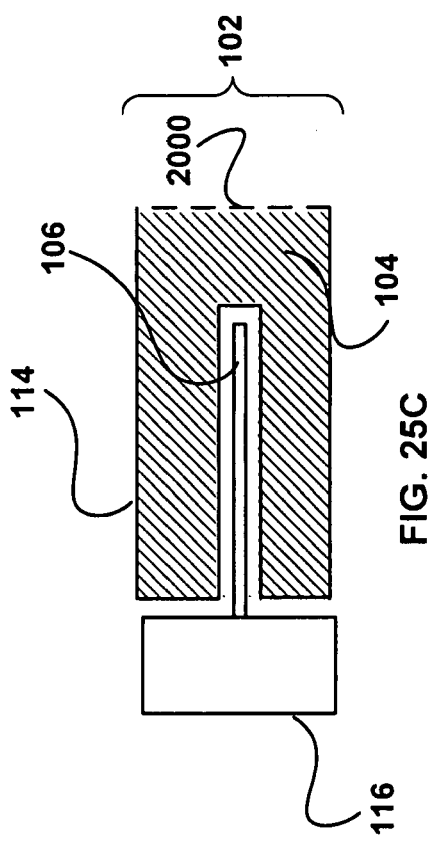
FIG. 25C

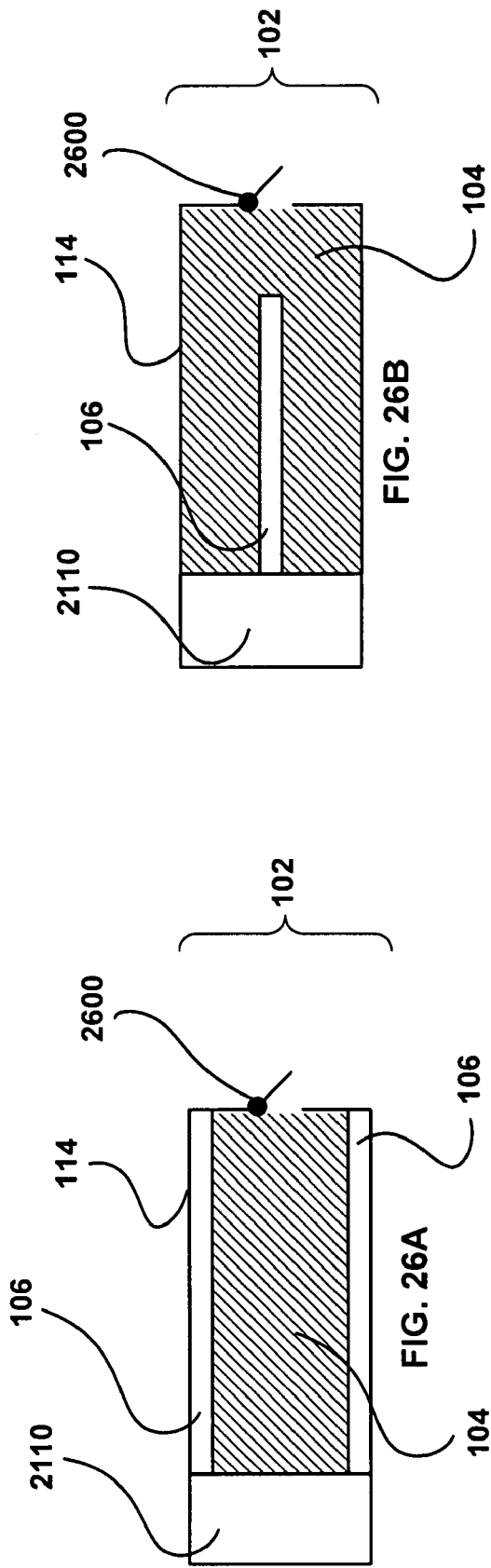

FIGS. 27A-27D
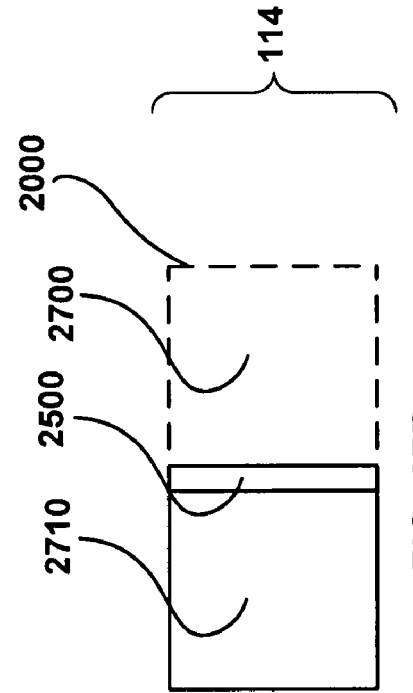
FIG. 27B
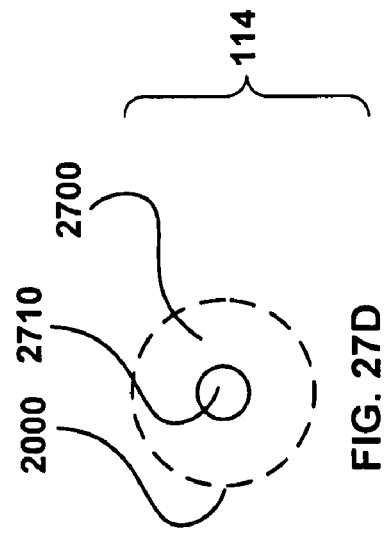
FIG. 27D
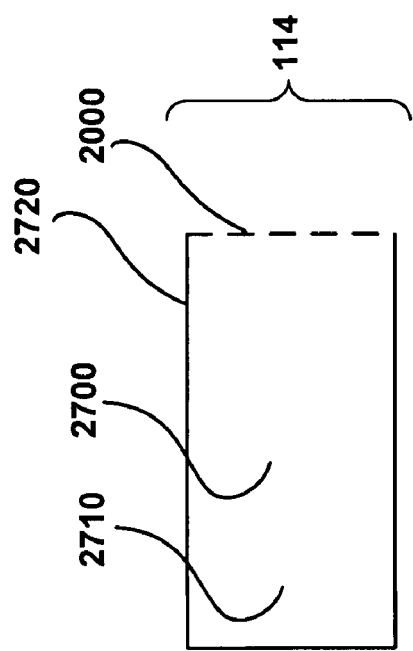
FIG. 27A
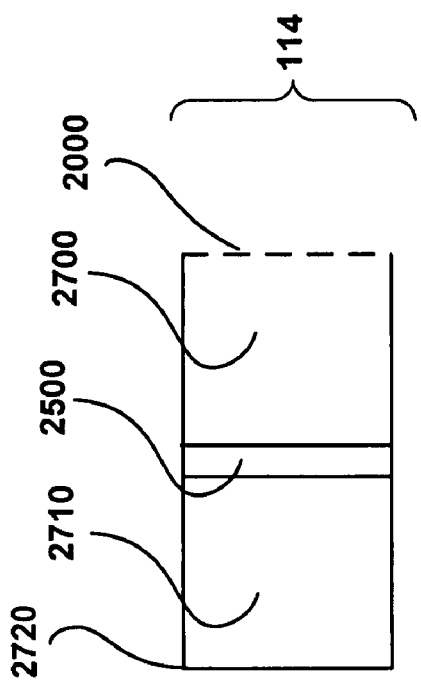
FIG. 27C FIGS. 28A-28C
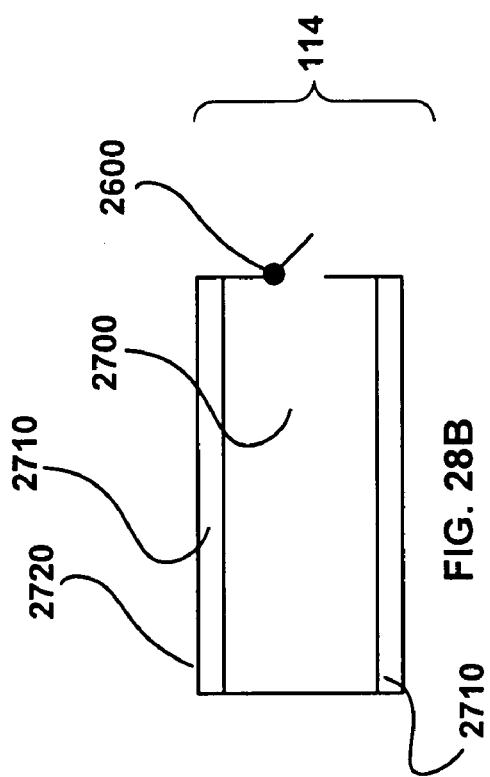
FIG. 28B
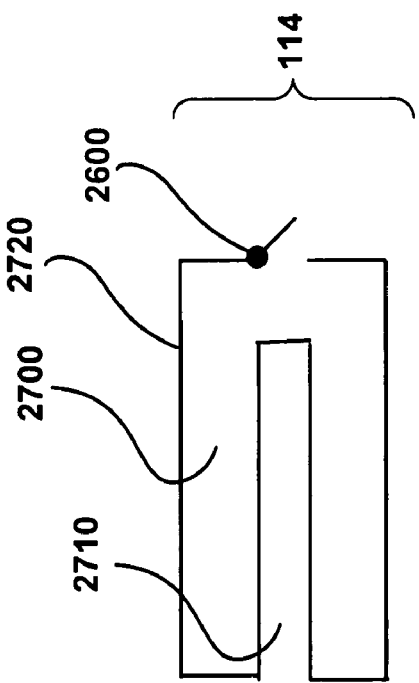
FIG. 28C
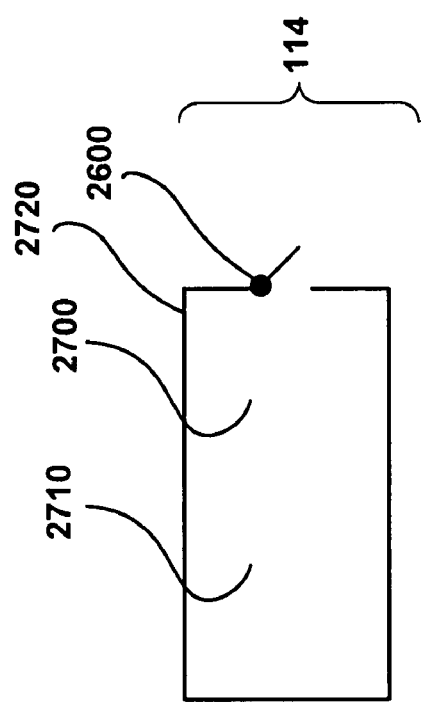
FIG. 28A

SYSTEMS AND DEVICES THAT UTILIZE PHOTOLYZABLE NITRIC OXIDE DONORS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/981,743, entitled Methods and Systems for Use of Photolyzable Nitric Oxide Donors, naming Roderick A. Hyde, Muriel Y. Ishikawa, and Lowell L. Wood, Jr. as inventors, filed Oct. 30, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to systems and devices that utilize photolyzable nitric oxide donors.

SUMMARY

In some embodiments one or more devices are provided that include one or more photolyzable nitric oxide donors and one or more light sources that are physically associated with the one or more photolyzable nitric oxide donors. The device may optionally include one or more nitric oxide permeable housings. The device may optionally include one or more control units. The device may optionally include one or more nitric oxide sensors. The device may optionally include one or more nitric oxide sensors. In addition to the foregoing, other aspects are described in the claims, drawings, and text forming a part of the present disclosure.

In some embodiments one or more systems are provided that include circuitry for operating one or more light sources that are physically associated with one or more photolyzable nitric oxide donors. The system may optionally include circuitry for operating one or more nitric oxide permeable housings. The system may optionally include circuitry for operating one or more control units. The system may optionally include circuitry for operating one or more nitric oxide sensors. The system may optionally include circuitry for operating one or more nitric oxide permeable housings.

In addition to the foregoing, other aspects are described in the claims, drawings, and text forming a part of the present disclosure.

In some embodiments one or more systems are provided that include means for operating one or more light sources that are physically associated with one or more photolyzable nitric oxide donors. The system may optionally include means for operating one or more nitric oxide permeable housings. The system may optionally include means for operating one or more control units. The system may optionally include means for operating one or more nitric oxide sensors. The system may optionally include means for operating one or more nitric oxide permeable housings. In addition to the foregoing, other aspects are described in the claims, drawings, and text forming a part of the present disclosure.

In some embodiments one or more systems are provided that include a signal-bearing medium bearing one or more instructions for operating one or more light sources that are physically associated with one or more photolyzable nitric oxide donors. The system may optionally include one or more instructions for operating one or more nitric oxide permeable housings. The system may optionally include one or more instructions for operating one or more control units. The system may optionally include one or more instructions for operating one or more nitric oxide sensors. The system may optionally include one or more instructions for operating one or more nitric oxide permeable housings. The system may optionally include one or more instructions for operating one or more nitric oxide sensors. In addition to the foregoing, other aspects are described in the claims, drawings, and text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustra-

BRIEF DESCRIPTION OF THE FIGURES

FIG. 3 illustrates alternate embodiments of embodiment 200 of device 102 within system 100.

FIG. 13 illustrates alternate embodiments of embodiment 1200 of device 102 within system 100.

FIG. 14 illustrates alternate embodiments of embodiment 1200 of device 102 within system 100.

FIG. 18 illustrates alternate embodiments of embodiment 1700 of device 102 within system 100.

FIG. 19 illustrates alternate embodiments of embodiment 1700 of device 102 within system 100.

FIGS. 20A-20E illustrate embodiments of device 102.

FIGS. 21A-21D illustrate embodiments of device 102.

FIGS. 22A-22C illustrate embodiments of device 102.

FIGS. 23A-23D illustrate embodiments of device 102.

FIGS. 24A-24C illustrate embodiments of device 102.

FIGS. 25A-25C illustrate embodiments of device 102.

FIGS. 26A-26C illustrate embodiments of device 102.

FIGS. 27A-27D illustrate embodiments of nitric oxide permeable housing 114.

FIGS. 28A-28C illustrate embodiments of nitric oxide permeable housing 114.

DETAILED DESCRIPTION

Figure 1:
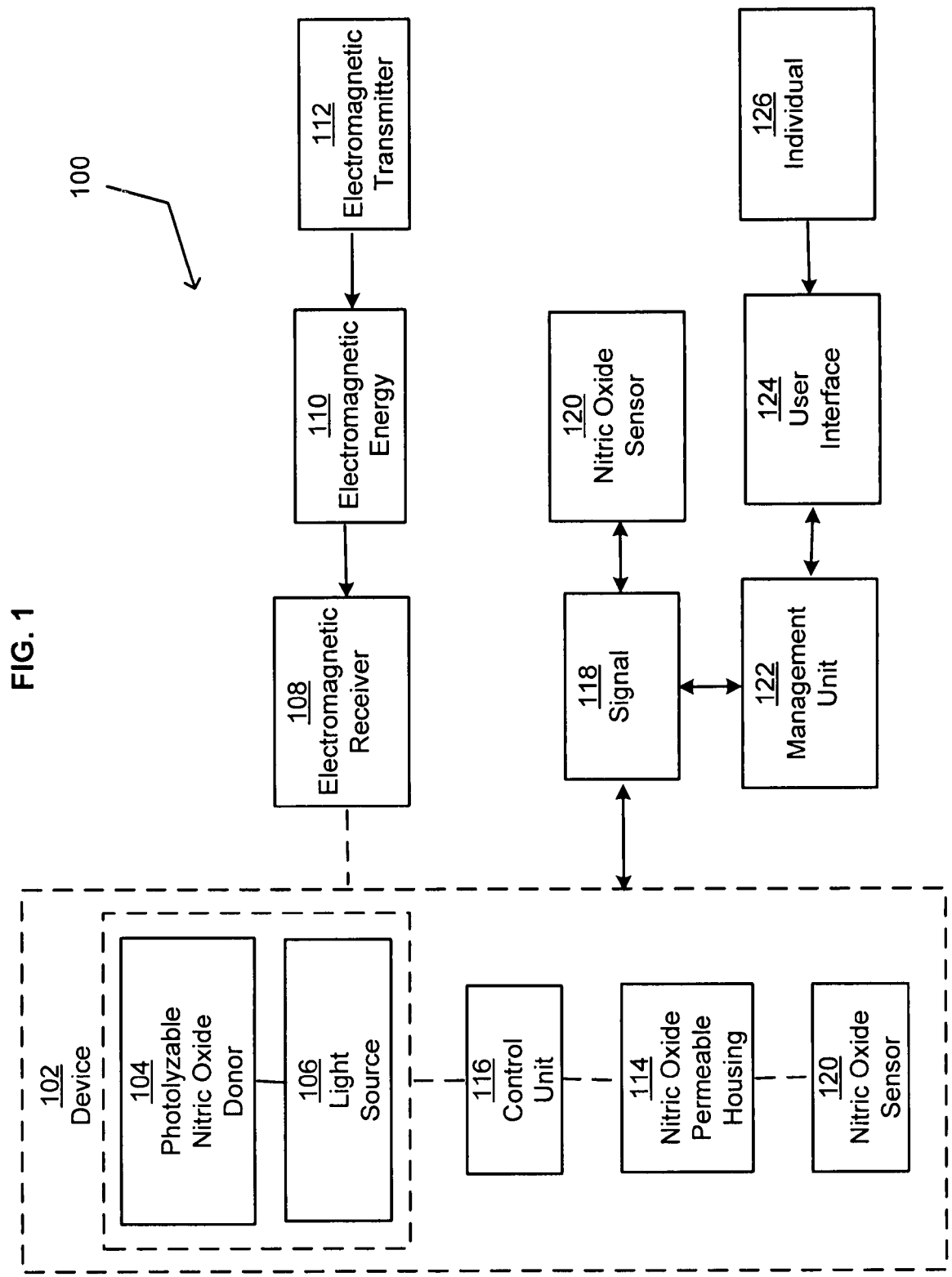
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates a system 100 in which embodiments may be implemented. System 100 may include one or more devices 102 that include one or more light sources 106 and one or more photolyzable nitric oxide donors 104. In some embodiments, system 100 may include one or more control units 116, one or more nitric oxide permeable housings 114, one or more nitric oxide sensors 120, and substantially any combination thereof. In some embodiments, the photolyzable nitric oxide donors 104 may be physically coupled with the one or more light sources 106. For example, in some embodiments, the one or more light sources 106 may be coated with the one or more photolyzable nitric oxide donors 104. In some embodiments, the one or more light sources 106 may include one or more polymeric materials that are coupled to at least one of the photolyzable nitric oxide donors 104. In some embodiments, one or more light sources 106 may be coated with a composition that includes one or more photolyzable nitric oxide donors 104. In some embodiments, one or more light sources 106 may be included within a housing that is coated with one or more photolyzable nitric oxide donors 104. Accordingly, in some embodiments, one or more light sources 106 may be in direct contact with one or more photolyzable nitric oxide donors 104. In some embodiments, one or more light sources 106 may be in indirect contact with one or more photolyzable nitric oxide donors 104. In some embodiments, the device 102 may include one or more operably coupled control units 116. In some embodiments, the one or more control units 116 may be operably coupled to the one or more light sources 106. In some embodiments, the one or more control units 116 may be operably coupled to the one or more light sources 106 and may be used to control the operation of the one or more light sources 106. In some embodiments, the one or more control units 116 may be configured to receive one or more signals 118. In some embodiments, the one or more control units 116 may be configured to receive one or more signals 118 from one or more transmitters. In some embodiments, the one or more control units 116 may be configured to receive one or more signals 118 from one or more nitric oxide sensors 120. In some embodiments, one or more nitric oxide permeable housings 114 may be configured to enclose one or more photolyzable nitric oxide donors 104. In some embodiments, one or more nitric oxide permeable housings 114 may be configured to enclose one or more photolyzable nitric oxide donors 104 and one or more light sources 106. In some embodiments, one or more nitric oxide permeable housings 114 may be configured to enclose one or more photolyzable nitric oxide donors 104, one or more light sources 106, and one or more control units 116. In some embodiments, one or more nitric oxide permeable housings 114 may be configured to enclose one or more photolyzable nitric oxide donors 104, one or more light sources 106, one or more control units 116, and one or more nitric oxide sensors 120. In some embodiments, one or more nitric oxide permeable housings 114 may be configured to enclose one or more photolyzable nitric oxide donors 104, one or more light sources 106, one or more control units 116, one or more nitric oxide sensors 120, or substantially any combination thereof. In some embodiments, one or more devices may be operably coupled to one or more electromagnetic receivers 108. In some embodiments, system 100 may include one or more electromagnetic receivers 108 that are configured to receive electromagnetic energy. In some embodiments, system 100 may include one or more electromagnetic receivers 108 that are configured to receive electromagnetic energy 110 that is transmitted by one or more electromagnetic transmitters 112. In some embodiments, the one or more electromagnetic receivers 108 may be operably coupled to the device. In some embodiments, the one or more electromagnetic receivers 108 may be operably coupled to the one or more light sources 106. In some embodiments, the one or more electromagnetic receivers 108 may be operably coupled to the one or more light sources 106 such that the one or more light sources 106 are energized through receipt of electromagnetic energy. In some embodiments, system 100 may include one or more light sources 106, one or more photolyzable nitric oxide donors 104, one or more control units 116, one or more nitric oxide permeable housings 114, one or more nitric oxide sensors 120, one or more electromagnetic receivers 108, one or more electromagnetic transmitters 112, or substantially any combination thereof.

Device

System 100 includes one or more devices 102. A device 102 may be configured in numerous ways. In some embodiments, a device 102 may be configured for implantation into an individual 126. For example, in some embodiments, a device 102 may be configured for implantation into the genital region of an individual 126. In some embodiments, a device 102 may be configured for application to an inside surface of an individual 126. For example, in some embodiments, a device 102 may be configured for insertion into the urethra of an individual 126. In some embodiments, a device 102 may be configured for vaginal insertion into an individual 126. In some embodiments, a device 102 may be configured for application to an outside surface of an individual 126. For example, in some embodiments, a device 102 may be configured for application to the skin of an individual 126. Accordingly, a device 102 may be configured in numerous ways to deliver nitric oxide to a surface or region of an individual 126. In some embodiments, a device 102 may be configured to deliver nitric oxide as a therapeutic agent. In some embodiments, a device 102 may be configured to deliver nitric oxide as a sanitizing agent. For example, in some embodiments, a device 102 may be configured to deliver nitric oxide to the surface of a table, a chair, to surgical instruments, and the like. In some embodiments, a device 102 may be incorporated into clothing. For example, in some embodiments, one or more devices 102 may be incorporated into a glove, a mitten, a hood, a mask, a sock, a shirt, a sheet, a bandage, tape, and the like.

Light Source

Numerous light sources 106 may be used within system 100. In some embodiments, one or more light sources 106 may be used to facilitate release of nitric oxide from one or more photolyzable nitric oxide donors 104. In some embodiments, one or more light sources 106 may be configured to emit light of multiple wavelengths. In some embodiments, one or more light sources 106 may be configured to emit light that is selected to facilitate release of nitric oxide from one or more photolyzable nitric oxide donors 104. For example, in some embodiments, one or more light sources 106 may be configured to emit one or more wavelengths of light that are selected to facilitate release of nitric oxide from one or more identified photolyzable nitric oxide donors 104. In some embodiments, one or more light sources 106 may emit one or more wavelengths of light that are selected based on the absorption spectrum of one or more photolyzable nitric oxide donors 104. In some embodiments, one or more light sources 106 may emit one or more wavelengths of light that are selected based on decomposition of one or more photolyzable nitric oxide donors 104. For example, in some embodiments, one or more light sources 106 may be configured to emit one or more wavelengths of light that cause decomposition of one or more photolyzable nitric oxide donors 104 without causing injury to adjacent structures and/or tissues. In some embodiments, a first light source 106 may be configured to emit one or more wavelengths of light that cause a first photolyzable nitric oxide donor 104 to release nitric oxide and a second light source 106 may be configured to emit one or more wavelengths of light that cause a second photolyzable nitric oxide donor 104 to release nitric oxide. Accordingly, numerous light sources 106 may be coupled with numerous types of photolyzable nitric oxide donors 104 to provide for selective release of nitric oxide.

In some embodiments, one or more light sources 106 may include one or more quantum dots (e.g., U.S. Pat. No. 7,235,361; herein incorporated by reference). For example, in some embodiments, one or more light sources 106 may be configured to emit one or more wavelengths of light that are absorbed by one or more quantum dots. In some embodiments, one or more quantum dots may be configured to absorb light and then emit one or more wavelengths of light that cause release of nitric oxide from one or more photolyzable nitric oxide donors 104. Accordingly, in some embodiments, emission from one or more first quantum dots may be tuned to facilitate release of nitric oxide from one or more first photolyzable nitric oxide donors 104 and emission from one or more second quantum dots may be tuned to facilitate release of nitric oxide from one or more second photolyzable nitric oxide donors 104.

In some embodiments, one or more light sources 106 may be configured to be used internally to illuminate one or more regions of an individual 126. A light source 106 may be configured in numerous ways. For example, in some embodiments, one or more light sources 106 may be configured for insertion into the urethra of a male and/or a female (e.g., U.S. Pat. No. 4,248,214; herein incorporated by reference). In some embodiments, one or more light sources 106 may be configured for vaginal insertion into a female. In some embodiments, one or more light sources 106 may be configured for implantation into an individual 126. For example, in some embodiments, one or more light sources 106 may be configured for implantation into the genital region of a male and/or a female. For example, in some embodiments, one or more light sources 106 may be configured for implantation within the corpus cavernosa of a penis. In some embodiments, one or more light sources 106 may be configured for implantation into the scrotal sack of a male. For example, in some embodiments, one or more light sources 106 may be configured to include one or more energy sources (e.g., one or more batteries), one or more light emitters (e.g., one or more light emitting diodes), and one or more optical fibers to deliver light to a selected region of an individual 126. In some embodiments, such light sources 106 may be implanted such that the energy sources and the light emitters are implanted into the scrotal sack of a male and optical fibers may be operably coupled to the one or more light emitters and implanted within the corpus cavernosa of the associated penis.

In some embodiments, one or more light sources 106 may be configured to externally illuminate an individual 126. Accordingly, one or more light sources 106 may be configured in numerous ways. For example, in some embodiments, a light source 106 may be associated with a lamp, a flashlight, a wand, a ring, a glove, a sheet, a condom, and the like. In some embodiments, one or more light sources 106 may be associated with clothing.

In some embodiments, light sources 106 may be remotely controlled. For example, in some embodiments, one or more light sources 106 may be configured to receive one or more signals 118 that include instructions for operation of the one or more light sources 106. Such instructions may be associated with emission of light, non-emission of light, time when light is emitted, length of light emission, intensity of light emission, wavelengths of emitted light, and the like.

In some embodiments, light sources 106 may be configured to include one or more control units 116. In some embodiments, one or more light sources 106 may be configured to include a switch that may be used to turn the light source 106 on and off. For example, in some embodiments, a light source 106 may be configured to include a push button switch to turn the light source 106 on and off.

In some embodiments, one or more light sources 106 may include one or more light emitters that are coupled to one or more electromagnetic receivers 108. The one or more electromagnetic receivers 108 may be configured to couple with one or more electromagnetic transmitters 112 that produce one or more electromagnetic fields that induce an electrical current to flow in the one or more electromagnetic receivers 108 to energize the light emitters (e.g., U.S. Pat. No. 5,571, 152; herein incorporated by reference). Accordingly, in some embodiments, one or more light sources 106 may be configured such that they are not directly coupled to an energy source.

A light source 106 may be configured to emit numerous types of light. In some embodiments, emitted light may be visible light. In some embodiments, emitted light may be infrared light. In some embodiments, emitted light may be ultraviolet light. In some embodiments, emitted light may be substantially any combination of visible light, infrared light, and/or ultraviolet light. In some embodiments, one or more light sources 106 may emit fluorescent light. In some embodiments, one or more light sources 106 may emit phosphorescent light.

In some embodiments, one or more light sources 106 may be configured to emit light continuously. In some embodiments, one or more light sources 106 may be configured to emit light as a pulse. In some embodiments, one or more light sources 106 may be configured to emit light as a flash. In some embodiments, one or more light sources 106 may be configured to emit light continuously, as a pulse, as a flash, or substantially any combination thereof.

In some embodiments, one or more light emitters and/or light sources 106 may be configured to provide for upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 106 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 106 may be associated with $Nd^{3+}$ doped $KPb_2Cl_5$ crystals. In some embodiments, one or more light sources 106 may be associated with thiogallates doped with rare earths, such as $CaGa_2S_4:Ce^{3+}$ and $SrGa_2S_4:Ce^{3+}$. In some embodiments, one or more light sources 106 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

Photolyzable Nitric Oxide Donor/Nitric Oxide

Numerous photolyzable nitric oxide donors 104 may be used within system 100. Examples of such photolyzable nitric oxide donors 104 include, but are not limited to, diazeniumdiolates (e.g., U.S. Pat. Nos. 7,105,502; 7,122,529; 6,673, 338; herein incorporated by reference), trans-[RuCl([15] aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

In some embodiments, one or more photolyzable nitric oxide donors 104 may be used in association with additional nitric oxide donors that are not photolyzable. In some embodiments, one or more photolyzable nitric oxide donors 104 may be used in association with additional agents. Examples of such additional agents include, but are not limited to, enzyme inhibitors (e.g., U.S. Pat. No. 6,943,166;

herein incorporated by reference), agents that increase the effects and/or concentration of nitric oxide 106 (e.g., methylene blue and N(w)-nitro-L-arginine (L-NOARG) (see Chen and Gillis, Biochem. Biophys. Res. Commun., 190, 559-563 (1993) and Kim et al., J. Vet. Sci., 1:81-86 (2000)), L-arginine (e.g., U.S. Published Patent Application No.: 20020068365 and U.S. Pat. No. 6,635,273; herein incorporated by reference), agents that stabilize nitric oxide donors (e.g., dimethyl sulfoxide and ethanol), agents that increase the half life of nitric oxide (e.g., U.S. Published Patent Application No.: 20030039697; herein incorporated by reference), and the like.

Control Unit

Numerous types of control units 116 may be used within system 100. In some embodiments, one or more control units 116 may be operably coupled with one or more light sources 106, one or more nitric oxide sensors 120, one or more electromagnetic receivers 108, one or more electromagnetic transmitters 112, or substantially any combination thereof. In some embodiments, one or more control units 116 may be operably coupled to other components through use of one or more wireless connections, one or more hardwired connections, or substantially any combination thereof. Control units 116 may be configured in numerous ways. For example, in some embodiments, a control unit 116 may be configured as an on/off switch. Accordingly, in some embodiments, a control unit 116 may be configured to turn a light source on and/or off. In some embodiments, a control unit 116 may be configured to control the emission of light from one or more light sources 106. For example, in some embodiments, one or more control units 116 may regulate the intensity of light emitted from one or more light sources 106, the duration of light emitted from one or more light sources 106, the frequency of light emitted from one or more light sources 106, wavelengths of light emitted from one or more light sources 106, or substantially any combination thereof. In some embodiments, one or more control units 116 may be configured to receive one or more signals 118 from one or more nitric oxide sensors 120. Accordingly, in some embodiments, one or more control units 116 may be configured to control one or more light sources 106 in response to one or more signals 118 received from one or more nitric oxide sensors 120. For example, in some embodiments, one or more nitric oxide sensors 120 may sense a low concentration of nitric oxide in one or more tissues and send one or more signals 118 to one or more control units 116. The one or more control units 116 may then turn one or more light sources 106 on to facilitate release of nitric oxide from one or more photolyzable nitric oxide donors 104. Accordingly, in some embodiments, one or more nitric oxide sensors 120 may sense a high concentration of nitric oxide in one or more tissues and send one or more signals 118 to one or more control units 116. The one or more control units 116 may then turn one or more light sources 106 off to end release of nitric oxide from one or more photolyzable nitric oxide donors 104. In some embodiments, one or more control units 116 may be programmed to control one or more light sources 106. For example, in some embodiments, one or more control units 116 may be programmed to turn one or more light sources 106 on for a predetermined amount of time and then turn off. Accordingly, in some embodiments, one or more control units 116 may be preprogrammed. In some embodiments, one or more control units 116 may be dynamically programmed. For example, in some embodiments, one or more management units 122 may receive one or more signals 118 from one or more nitric oxide sensors 120 and program one or more control units 116 in response to the one or more signals 118 received from the one or more nitric oxide sensors 120. In some embodiments, one or more control units 116 may include one or more receivers that are able to receive one or more signals 118, one or more information packets, or substantially any combination thereof. Control units 116 may be configured in numerous ways. For example, in some embodiments, one or more control units 116 may be operably coupled to one or more light sources 106 that include numerous light emitting diodes that emit light of different wavelengths. Accordingly, in some embodiments, one or more control units 116 may control the wavelengths of light emitted by the one or more light sources 106 by controlling the operation of light emitting diodes that emit light of the selected wavelength. Accordingly, control units 116 may be configured in numerous ways and utilize numerous types of mechanisms.

Nitric Oxide Permeable Housing

Numerous types of nitric oxide permeable housings 114 may be used within system 100. Nitric oxide permeable housings 114 may be configured for implantation within an individual 126. In some embodiments, one or more nitric oxide permeable housings 114 may be configured for implantation into the genital region of an individual 126. For example, in some embodiments, one or more nitric oxide permeable housings 114 may be configured for implantation into the corpus cavernosa of a penis. Nitric oxide permeable housings 114 may be configured to facilitate application of nitric oxide to a surface. In some embodiments, one or more nitric oxide permeable housings 114 may be configured to facilitate application of nitric oxide to one or more surfaces of an individual 126. For example, in some embodiments, one or more nitric oxide permeable housings 114 may be configured as a canister having a nitric oxide permeable end that may be positioned on a skin surface of an individual 126 to deliver nitric oxide to the skin surface. In some embodiments, one or more nitric oxide permeable housings 114 may be configured for insertion into the urethra of a male. In some embodiments, one or more nitric oxide permeable housings 114 may be configured for insertion into the vagina of a female.

In some embodiments, one or more nitric oxide permeable housings 114 may be configured to enclose at least a portion of one or more photolyzable nitric oxide donors 104. In some embodiments, one or more nitric oxide permeable housings 114 may be configured to enclose at least a portion of one or more light sources 106. In some embodiments, one or more nitric oxide permeable housings 114 may be configured to enclose at least a portion of one or more control units 116. In some embodiments, one or more nitric oxide permeable housings 114 may be configured to enclose at least a portion of one or more nitric oxide sensors 120. In some embodiments, one or more nitric oxide permeable housings 114 may be configured to enclose one or more photolyzable nitric oxide donors 104. In some embodiments, one or more nitric oxide permeable housings 114 may be configured to enclose one or more light sources 106. In some embodiments, one or more nitric oxide permeable housings 114 may be configured to enclose one or more photolyzable nitric oxide donors 104 and one or more light sources 106. In some embodiments, one or more nitric oxide permeable housings 114 may be configured to enclose one or more photolyzable nitric oxide donors 104, one or more light sources 106, and one or more control units 116. In some embodiments, one or more nitric oxide permeable housings 114 may be configured to enclose one or more photolyzable nitric oxide donors 104, one or more light sources 106, one or more control units 116, and one or more electromagnetic receivers 108. In some embodiments, one or more nitric oxide permeable housings 114 may be configured to enclose one or more photolyzable nitric oxide donors 104, one or more light sources 106, one or more control units 116, one or more electromagnetic receivers 108, or substantially any combination thereof. In some embodiments, one or more nitric oxide permeable housings 114 may be configured to include one or more compartments. For example, in some embodiments, a nitric oxide permeable housing 114 may include a compartment that is configured to accept one or more light sources 106 and a second compartment that is configured to accept one or more photolyzable nitric oxide donors 104. In some embodiments, a nitric oxide permeable housing 114 may include a compartment that is configured to accept one or more light sources 106, a light permeable divider, and a second compartment that is configured to accept one or more photolyzable nitric oxide donors 104. In some embodiments, a light permeable divider may be made of a material that allows light to pass through the divider. Examples of such material include, but are not limited to, plastic, quartz, and the like.

Nitric oxide permeable housings 114 may be constructed of numerous types of materials and combinations of materials. Examples of such materials include, but are not limited to, ceramics, polymeric materials, metals, plastics, and the like. In some embodiments, nitric oxide permeable housings 114 may include numerous combinations of materials. For example, in some embodiments, a nitric oxide permeable housing 114 may include a nitric oxide impermeable metal canister that is coupled to a nitric oxide permeable membrane (e.g., U.S. Patent Application No.: 20020026937). In some embodiments, a nitric oxide permeable housing 114 may include a selectively permeable membrane. For example, in some embodiments, a nitric oxide permeable housing 114 may include a selectively permeable, hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable housing 114 may include a scintered glass portion that is permeable to nitric oxide. Accordingly, nitric oxide permeable housings 114 may include numerous types of porous ceramics that are permeable to nitric oxide. In some embodiments, a nitric oxide permeable housing 114 may include a nitric oxide permeable coating (e.g., U.S. Patent Application Nos. 20050220838; 20030093143). In some embodiments, one or more nitric oxide permeable housing 114 may include one or more valves. In some embodiments, a nitric oxide permeable housing 114 may include one or more valves that are controllable by one or more control units 116. Accordingly, in some embodiments, valves may be opened or closed in response to one or more nitric oxide sensors 120, one or more signals 118, one or more information packets, one or more management units 122, or substantially any combination thereof.

Nitric Oxide Sensor

Numerous types of nitric oxide sensors 120 may be used within system 100. In some embodiments, a nitric oxide sensor 120 may be configured for implantation into an individual 126. For example, in some embodiments, one or more nitric oxide sensors 120 may be configured to be implanted into the genital region of an individual 126. Accordingly, in some embodiments, one or more nitric oxide sensors 120 may be used to determine the presence of nitric oxide in one or more tissues. In some embodiments, a nitric oxide sensor 120 may be configured for use on the outside surface of an individual 126. For example, in some embodiments, one or more nitric oxide sensors 120 may be configured to detect the concentration of nitric oxide on the surface of skin, a wound, a surface of a table, and the like. In some embodiments, one or more nitric oxide sensors 120 may be configured to be included within one or more housings. In some embodiments, one or more nitric oxide sensors 120 may be configured to be included within one or more nitric oxide permeable housings 114. In some embodiments, a nitric oxide sensor 120 may be configured to utilize fluorescence to detect nitric oxide. For example, in some embodiments, a nitric oxide sensor may detect nitric oxide through use of one or more fluorescent probes, such as 4,5-diaminofluorescein diacetate (EMD Chemicals Inc., San Diego, Calif.). In some embodiments, a nitric oxide sensor may detect nitric oxide through use of one or more electrodes. For example, in some embodiments, a nitric oxide sensor may utilize an electrode that includes a single walled carbon nanotube and an ionic liquid to detect nitric oxide (e.g., Li et al., Electroanalysis, 18:713-718 (2006)). Numerous nitric oxide sensors 120 are commercially available and have been described (e.g., World Precision Instruments, Inc., Sarasota, Fla., USA; U.S. Pat. Nos. 6,100, 096; 6,280,604; 5,980,705). In some embodiments, a nitric oxide sensor 120 may include one or more transmitters. In some embodiments, a nitric oxide sensor 120 may include one or more receivers. In some embodiments, a nitric oxide sensor 120 may be configured to transmit one or more signals 118. In some embodiments, a nitric oxide sensor 120 may be configured to receive one or more signals 118.

Electromagnetic Receiver

Numerous types of electromagnetic receivers 108 may be used within system 100. In some embodiments, one or more electromagnetic receivers 108 may be used to electromagnetically couple power to energize one or more light sources 106 from an external power supply. Methods to construct such electromagnetic receivers 108 have been described (e.g., U.S. Pat. No. 5,571,152). Briefly, in some embodiments, one or more electromagnetic receivers 108 may be associated with one or more rectifier chips. The one or more electromagnetic receivers 108 may include one or more cores about which are wrapped an electrical conductor. In some embodiments, cores may comprise a material, such as a ferrite material, due to its relatively high magnetic permeability and low magnetic hysteresis. However, other materials can be used for this purpose. In some embodiments, the electromagnetic receiver 108 may be operably coupled to a light emitting diode.

Electromagnetic Transmitter

Numerous types of electromagnetic transmitters 112 may be used within system 100. Methods to construct electromagnetic transmitters 112 have been described (e.g., U.S. Pat. No. 5,571,152). Briefly, in some embodiments, the electromagnetic transmitter 112 may include a ferrite core around which is wrapped an electrical conductor. Other types of material having high magnetic permeability and relatively low magnetic hysteresis may be used for the core. Insulating tape may be wrapped around the electrical conductor, or the electromagnetic transmitter 112 may be dipped in a resin to form a coating that stabilizes and fixes the electrical conductor on the core. A return lead from one end of the electrical conductor may include one of two leads that are coupled to an AC power supply.

Electromagnetic Energy

Electrical power may be electromagnetically coupled from one or more electromagnetic transmitters 112 with one or more electromagnetic receivers 108. Accordingly, electrical power that is transferred to the one or more electromagnetic receivers 108 may be used to power one or more operably linked light emitters. Methods and devices that may be used to transmit electrical power to a light emitter have been described (e.g., U.S. Pat. No. 5,571,152).

Management Unit

In some embodiments, system 100 may include one or more management units 122. In some embodiments, a management unit 122 may be configured as a computer. Accordingly, in some embodiments, a management unit 122 may be configured to accept input and provide output. For example, in some embodiments, a management unit 122 may receive one or more signals 118 from one or more nitric oxide sensors 120, process the one or more signals 118, and then transmit one or more signals 118. In some embodiments, one or more transmitted signals 118 may be received by one or more control units 116. In some embodiments, one or more transmitted signals 118 may be received by one or more light sources 106. Accordingly, in some embodiments, a management unit 122 may be configured to manage nitric oxide production by a device. For example, in some embodiments, a management unit 122 may include and execute a set of instructions for the operation of one or more control units 116 that facilitate production of nitric oxide by one or more devices 102 at preselected times and for preselected concentrations. In some embodiments, such production may be regulated through control of the intensity of light emitted by one or more light sources 106, the duration of light emitted by one or more light sources 106, the frequency of light emitted by one or more light sources 106, and the like. In some embodiments, a management unit 122 may dynamically control the production of nitric oxide by one or more devices. For example, in some embodiments, a management unit 122 may be configured to maintain a nitric oxide concentration within a range of concentrations. Accordingly, the management unit 122 may receive one or more signals 118 from one or more nitric oxide sensors 120 indicating a current concentration of nitric oxide. The management unit 122 may then determine if the nitric oxide concentration is within a range of nitric oxide concentrations or out of a range of nitric oxide concentrations and then increase nitric oxide production, decrease nitric oxide production, or maintain nitric oxide production to cause the nitric oxide concentration to be maintained within a range. Accordingly, a management unit 122 may be used in numerous ways to regulate nitric oxide production.

Transmitter

The system 100 may include one or more transmitters. In some embodiments, one or more transmitters may be operably coupled to one or more nitric oxide sensors 120. In some embodiments, one or more transmitters may be operably coupled to one or more management units 122. In some embodiments, one or more transmitters may be operably coupled to one or more control units 116. In some embodiments, one or more transmitters may be operably coupled to one or more nitric oxide sensors 120, one or more control units 116, one or more management units 122, or substantially any combination thereof. Numerous types of transmitters may be used in association with system 100. Examples of such transmitters include, but are not limited to, transmitters that transmit one or more optical signals 118, radio signals 118, wireless signals 118, hardwired signals 118, infrared signals 118, ultrasonic signals 118, and the like (e.g., U.S. Pat. Nos. RE39,785; 7,260,768; 7,260,764; 7,260,402; 7,257,327; 7,215,887; 7,218,900; herein incorporated by reference). In some embodiments, one or more transmitters may transmit one or more signals 118 that are encrypted. Numerous types of transmitters are known and have been described (e.g., U.S. Pat. Nos. and Published U.S. Patent Application No. 7,236,595; 7,260,155; 7,227,956; US2006/0280307; herein incorporated by reference).

Signal

Numerous types of signals 118 may be used in association with system 100. Examples of such signals 118 include, but are not limited to, optical signals 118, radio signals 118, wireless signals 118, hardwired signals 118, infrared signals 118, ultrasonic signals 118, and the like.

In some embodiments, one or more signals 118 may not be encrypted. In some embodiments, one or more signals 118 may be encrypted. In some embodiments, one or more signals 118 may be sent through use of a secure mode of transmission. In some embodiments, one or more signals 118 may be coded for receipt by a specific individual 126. In some embodiments, such code may include anonymous code that is specific for an individual 126. Accordingly, information included within one or more signals 118 may be protected against being accessed by others who are not the intended recipient.

Receiver

System 100 may include one or more receivers. In some embodiments, one or more receivers may be operably coupled to one or more nitric oxide sensors 120. In some embodiments, one or more receivers may be operably coupled to one or more management units 122. In some embodiments, one or more receivers may be operably coupled to one or more control units 116. In some embodiments, one or more receivers may be operably coupled to one or more nitric oxide sensors 120, one or more control units 116, one or more management units 122, or substantially any combination thereof. Numerous types of receivers may be used in association with system 100. Examples of such receivers include, but are not limited to, receivers that receive one or more optical signals 118, radio signals 118, wireless signals 118, hardwired signals 118, infrared signals 118, ultrasonic signals 118, and the like. Such receivers are known and have been described (e.g., U.S. Pat. Nos. RE39,785; 7,218,900; 7,254,160; 7,245,894; 7,206,605; herein incorporated by reference).

User Interface/User

System 100 may include numerous types of user interfaces 124. For example, one or more users (e.g., individuals 126) may interact through use of numerous user interfaces 124 that utilize hardwired methods, such as through use of an on/off switch, a push button, a keyboard, and the like. In some embodiments, the user interface 124 may utilize wireless methods, such as methods that utilize a transmitter and receiver, utilize the internet, and the like.

Individual

A device 102 may be used to deliver nitric oxide to an individual 126. In some embodiments, an individual 126 may be a human. In some embodiments, an individual 126 may be a human male. In some embodiments, an individual 126 may be a human female. A device 102 may be used within numerous contexts. For example, in some embodiments, a device 102 may be used to deliver nitric oxide to an individual 126 to treat sexual dysfunction. In some embodiments, a device 102 may be used to treat female arousal disorder. In some embodiments, a device 102 may be used to treat male erectile disorder. In some embodiments, sexual dysfunction may be due to a physical condition. For example, in some embodiments, sexual dysfunction may result from surgery, a physical injury, pharmaceutical use, age, or the like. In some embodiments, sexual dysfunction may be due to a mental condition. For example, in some embodiments, sexual dysfunction may be due to depression, lack of interest, insecurity, anxiety, or the like. In some embodiments, a device 102 may deliver nitric oxide to increase sexual performance and/or pleasure. In some embodiments, a device 102 may be used to deliver nitric oxide to the skin of an individual 126. In some embodiments, such delivery may be for cosmetic purposes. In some embodiments, such delivery may be for therapeutic purposes. For example, in some embodiments, a device 102 may be used to deliver nitric oxide to a skin lesion, such as a skin ulcer, a burn, a cut, a puncture, a laceration, a blunt trauma, an acne lesion, a boil, and the like. In some embodiments, a device 102 may be used to deliver nitric oxide to a skin surface to increase the expression of endogenous collagenase. In some embodiments, a device 102 may be used to deliver nitric oxide to a skin surface to regulate the formation of collagen. In some embodiments, a device 102 may be used to deliver nitric oxide to reduce inflammation (e.g., reduce exudate secretion) at the site of a lesion (e.g., U.S. Patent Application No.: 2007/0088316). In some embodiments, a device 102 may be used to deliver nitric oxide to reduce the microbial burden within a wound site. For example, in some embodiments, a device 102 may be used to deliver nitric oxide as an antibacterial agent against methicillin-resistant *Staphylococcus aureus*. A device 102 may deliver nitric oxide to an individual 126 at numerous concentrations. For example, in some embodiments, nitric oxide may be delivered at a concentration ranging from about 160 ppm to about 400 ppm. Such concentrations may be used without inducing toxicity in the healthy cells around a wound site (e.g., U.S. Patent Application No.: 2007/0088316).

Administration Form

Numerous types of administration forms 110 may be used to provide one or more photolyzable nitric oxide donors 104 to an individual 126. In some embodiments, an administration form may be a formulation of one or more photolyzable nitric oxide donors 104. In some embodiments, an administration form may be configured for oral delivery of one or more photolyzable nitric oxide donors 104 to an individual 126. For example, in some embodiments, an administration form may be configured as a pill, a lozenge, a capsule, a liquid, and the like. In some embodiments, an administration form may be configured for topical delivery of one or more photolyzable nitric oxide donors 104 to an individual 126. For example, in some embodiments, an administration form may be configured as a gel, a cream, a lotion, a lubricant, a jelly, and the like. In some embodiments, one or more photolyzable nitric oxide donors 104 may be formulated with one or more liposomes to provide for delivery of the one or more photolyzable nitric oxide donors 104 to the individual 126. In some embodiments, one or more photolyzable nitric oxide donors 104 may be formulated with one or more detergents to facilitate delivery of the one or more photolyzable nitric oxide donors 104 to the individual 126. In some embodiments, one or more photolyzable nitric oxide donors 104 may be formulated with one or more agents that stabilize the one or more photolyzable nitric oxide donors 104. In some embodiments, one or more photolyzable nitric oxide donors 104 may be formulated for administration to one or more individuals 126 through inhalation. In some embodiments, one or more photolyzable nitric oxide donors 104 may be formulated for administration to one or more individuals 126 through parenteral administration.

In some embodiments, an administration form may include an implant. In some embodiments, one or more photolyzable nitric oxide donors 104 may be coupled to a structure that can be implanted within an individual 126. For example, in some embodiments, one or more photolyzable nitric oxide donors 104 may be coupled to a polymeric structure for implantation into an individual 126 (e.g., U.S. Pat. Nos. 5,405,919; 6,451,337; 7,052,711: herein incorporated by reference, Smith et al., J. Med. Chem., 1:1148-1156 (1996)). In some embodiments, one or more photolyzable nitric oxide donors 104 may be included within a porous structure and/or matrix for implantation into an individual 126 (e.g., U.S. Published Patent Application No. 20030039697; herein incorporated by reference). Such structures may be constructed from numerous materials that include, but are not limited to, polymers, ceramics, metals, and the like. In some embodiments, one or more photolyzable nitric oxide donors 104 may be formulated for depot administration to an individual 126. For example, in some embodiments, one or more photolyzable nitric oxide donors 104 may be formulated with one or more biodegradable materials that degrade within an individual 126 to release the one or more photolyzable nitric oxide donors 104 (e.g., U.S. Pat. Nos. 5,736,152; 6,143,314; 6,773,714; herein incorporated by reference). Accordingly, in some embodiments, one or more photolyzable nitric oxide donors 104 may be included within a flowable material that forms an implant upon being injected into an individual 126.

In some embodiments, one or more photolyzable nitric oxide donors 104 may be formulated with one or more additional agents. Examples of such agents include, but are not limited to, enzyme inhibitors, additional nitric oxide donors, free radical scavengers, and the like. In some embodiments, one or more photolyzable nitric oxide donors 104 may be formulated with one or more light sources 106 (e.g., U.S. Pat. No. 5,571,152; herein incorporated by reference). In some embodiments, one or more photolyzable nitric oxide donors 104 may be formulated with one or more quantum dots (e.g., U.S. Pat. No. 7,235,361; herein incorporated by reference).

Figure 2:
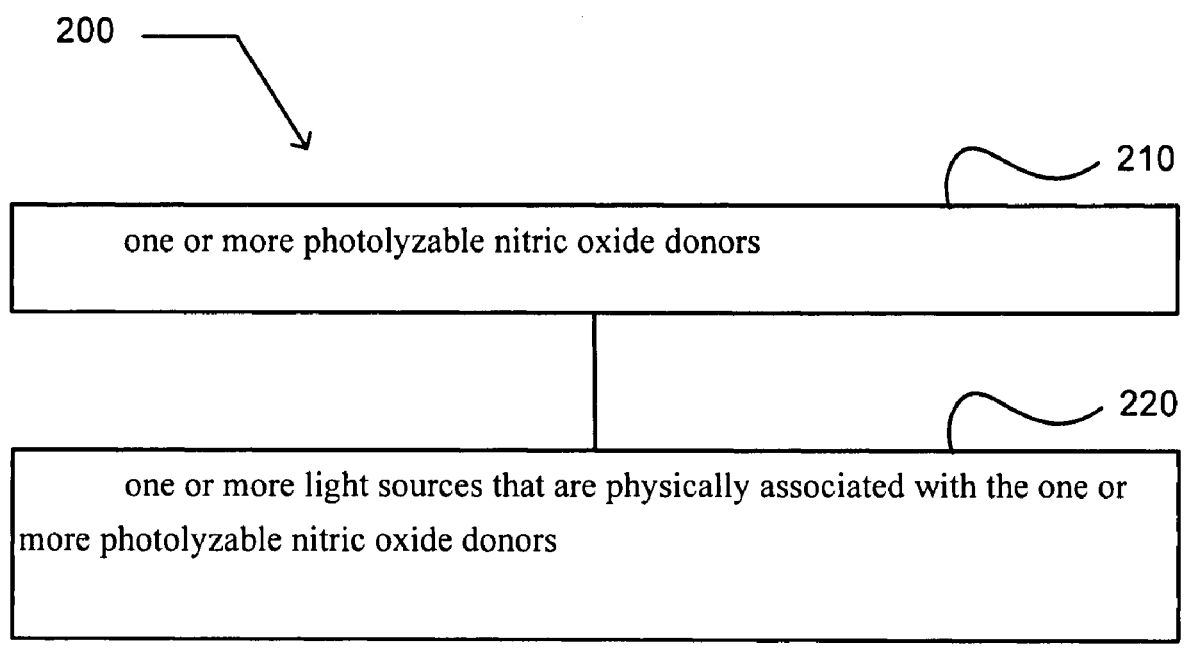
FIG. 2 illustrates embodiment 200 of device 102 within system 100.

FIG. 2 illustrates embodiment 200 of device 102 within system 100. In FIG. 2, discussion and explanation may be provided with respect to the above-described example of FIG. 1, and/or with respect to other examples and contexts. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 200 may include module 210 that includes one or more photolyzable nitric oxide donors. In some embodiments, device 102 may include one or more photolyzable nitric oxide donors 104 that release nitric oxide upon photolysis. Examples of such photolyzable nitric oxide donors 104 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[A]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 200 may include module 220 that includes one or more light sources that are physically associated with the one or more photolyzable nitric oxide donors. In some embodiments, device 102 may include one or more light sources 106 that are physically associated with one or more photolyzable nitric oxide donors 104. In some embodiments, the one or more light sources 106 may be directly coupled to one or more photolyzable nitric oxide donors 104. For example, in some embodiments, the one or more photolyzable nitric oxide donors 104 may be chemically coupled to a surface of the light source 106 (e.g., chemically coupled to a polymer coating on the light source). In some embodiments, one or more photolyzable nitric oxide donors 104 may be indirectly coupled to one or more light sources 106. For example, in some embodiments, one or more photolyzable nitric oxide donors 104 may be coupled to a material that is used to coat the one or more light sources 106.

FIG. 3 illustrates alternative embodiments of embodiment 200 of device 102 within system 100 of FIG. 2. FIG. 3 illustrates example embodiments of module 210. Additional embodiments may include an embodiment 302, an embodiment 304, an embodiment 306, an embodiment 308, an embodiment 310, an embodiment 312, and/or an embodiment 314.

At embodiment 302, module 210 may include one or more photolyzable nitric oxide donors that include one or more diazeniumdiolates. In some embodiments, one or more photolyzable nitric oxide donors 104 may include one or more diazeniumdiolates. Many photolyzable nitric oxide donors 104 that are diazeniumdiolates are known and have been described (e.g., U.S. Pat. No. 7,122,529). Examples of such diazeniumdiolates include, but are not limited to, $O^2$-benzyl, $O^2$-naphthylmethyl substituted diazeniumdiolates and $O^2$-naphthylallyl substituted diazeniumdiolates.

At embodiment 304, module 210 may include one or more photolyzable nitric oxide donors that are associated with one or more quantum dots. In some embodiments, one or more photolyzable nitric oxide donors 104 may be associated with one or more quantum dots. For example, in some embodiments, one or more diazeniumdiolates may be associated with one or more quantum dots. In some embodiments, one or more quantum dots may be tuned to emit light that facilitates photolysis of one or more nitric oxide donors. In some embodiments, a quantum dot may be tuned to emit light that specifically facilitates photolysis of one or more nitric oxide donors. For example, in some embodiments, one or more quantum dots may emit select wavelengths of light that correspond to wavelengths of light that cause photolysis of one or more nitric oxide donors. In some embodiments, one or more quantum dots may be selected that absorb light emitted by one or more light sources 106 and emit light that facilitates photolysis of one or more nitric oxide donors.

At embodiment 306, module 210 may include one or more photolyzable nitric oxide donors that are associated with one or more optical fibers. In some embodiments, one or more photolyzable nitric oxide donors 104 may be associated with one or more optical fibers. In some embodiments, one or more photolyzable nitric oxide donors 104 may be directly associated with one or more optical fibers. For example, in some embodiments, one or more optical fibers may be directly coated with one or more photolyzable nitric oxide donors 104. In some embodiments, one or more optical fibers may be directly coated with one or more compositions that include one or more photolyzable nitric oxide donors 104.

In some embodiments, one or more portions of one or more optical fibers may be directly coated with one or more photolyzable nitric oxide donors 104. In some embodiments, one or more portions of one or more optical fibers may be directly coated with one or more compositions that include one or more photolyzable nitric oxide donors 104. In some embodiments, one or more photolyzable nitric oxide donors 104 may be indirectly associated with one or more optical fibers. For example, in some embodiments, one or more optical fibers may be inserted into a structure that is coated with one or more photolyzable nitric oxide donors 104. In some embodiments, one or more optical fibers may be inserted into a structure that is coated with one or more compositions that include one or more photolyzable nitric oxide donors 104. In some embodiments, one or more optical fibers may be inserted into a structure that is partially coated with one or more photolyzable nitric oxide donors 104. In some embodiments, one or more optical fibers may be inserted into a structure that is partially coated with one or more compositions that include one or more photolyzable nitric oxide donors 104. For example, in some embodiments, one or more optical fibers may be inserted into one or more tubes that are coated with one or more photolyzable nitric oxide donors 104. In some embodiments, one or more optical fibers may be inserted into one or more tubes that are coated with one or more compositions that include one or more photolyzable nitric oxide donors 104. One or more photolyzable nitric oxide donors 104 may be associated with numerous types of optical fibers. Methods to construct optical fibers have been described. Examples of optical fibers include, but are not limited to, optical fibers that include a single core and/or one or more cores. In some embodiments, an optical fiber may include silica glass. In some embodiments, an optical fiber may include a cladding. Optical fibers have been described (e.g., U.S. Pat. Nos. 7,295,741; 7,295,737).

At embodiment 308, module 210 may include one or more photolyzable nitric oxide donors that are associated with one or more fluorescent materials. In some embodiments, one or more light sources 106 may include one or more photolyzable nitric oxide donors 104 that are associated with one or more fluorescent materials. Numerous fluorescent materials may be associated with one or more light sources 106. Examples of such materials include, but are not limited to, 1,4-diphenylbutadiyne; 9,10-diphenylanthracene; benzene; biphenyl; ethyl-p-dimethylaminobenzoate; naphthalene; P-terphenyl;

ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 310, module 210 may include one or more photolyzable nitric oxide donors that are associated with one or more rare-earth materials. In some embodiments, one or more light sources 106 may include one or more photolyzable nitric oxide donors 104 that are associated with one or more rare-earth materials. In some embodiments, one or more rare-earth materials may include one or more rare-earth elements. The rare-earth elements are a collection of sixteen chemical elements in the periodic table, namely scandium, yttrium, and fourteen of the fifteen lanthanoids (excluding promethium). In some embodiments, one or more rare-earth materials may include one or more rare-earth elements that fluoresce.

At embodiment 312, module 210 may include one or more photolyzable nitric oxide donors that are associated with one or more rare-earth materials that facilitate upconversion of energy. In some embodiments, one or more photolyzable nitric oxide donors 104 may be associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more photolyzable nitric oxide donors 104 may be associated with one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more photolyzable nitric oxide donors 104 may be associated with $Nd^{3+}$ doped $KPb_2Cl_5$ crystals. In some embodiments, one or more photolyzable nitric oxide donors 104 may be associated with thiogallates doped with rare earths, such as $CaGa_2S_4:Ce^{3+}$ and $SrGa_2S_4:Ce^{3+}$. In some embodiments, one or more photolyzable nitric oxide donors 104 may be associated with aluminates that are doped with rare earths, such as $YAlO_3:Ce^{3+}$, $YGaO_3:Ce^{3+}$, $Y(Al,Ga)O_3$: $Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 314, module 210 may include one or more photolyzable nitric oxide donors that are coupled to one or more polymeric materials. In some embodiments, one or more photolyzable nitric oxide donors 104 may be coupled to one or more polymeric materials. For example, in some embodiments, one or more polymer matrices may be impregnated with one or more photolyzable nitric oxide donors 104 (e.g., U.S. Pat. No. 5,994,444). In some embodiments, one or more photolyzable nitric oxide donors 104 may be bound to a polymer. Methods that can be used to couple nitric oxide donors to a polymeric matrix have been reported (e.g., U.S. Pat. No. 5,405,919). In some embodiments, one or more photolyzable nitric oxide donors 104 may be coupled to polymeric materials used to produce condoms. Accordingly, in some embodiments, one or more photolyzable nitric oxide donors 104 may be coupled to a condom.

Figure 4:
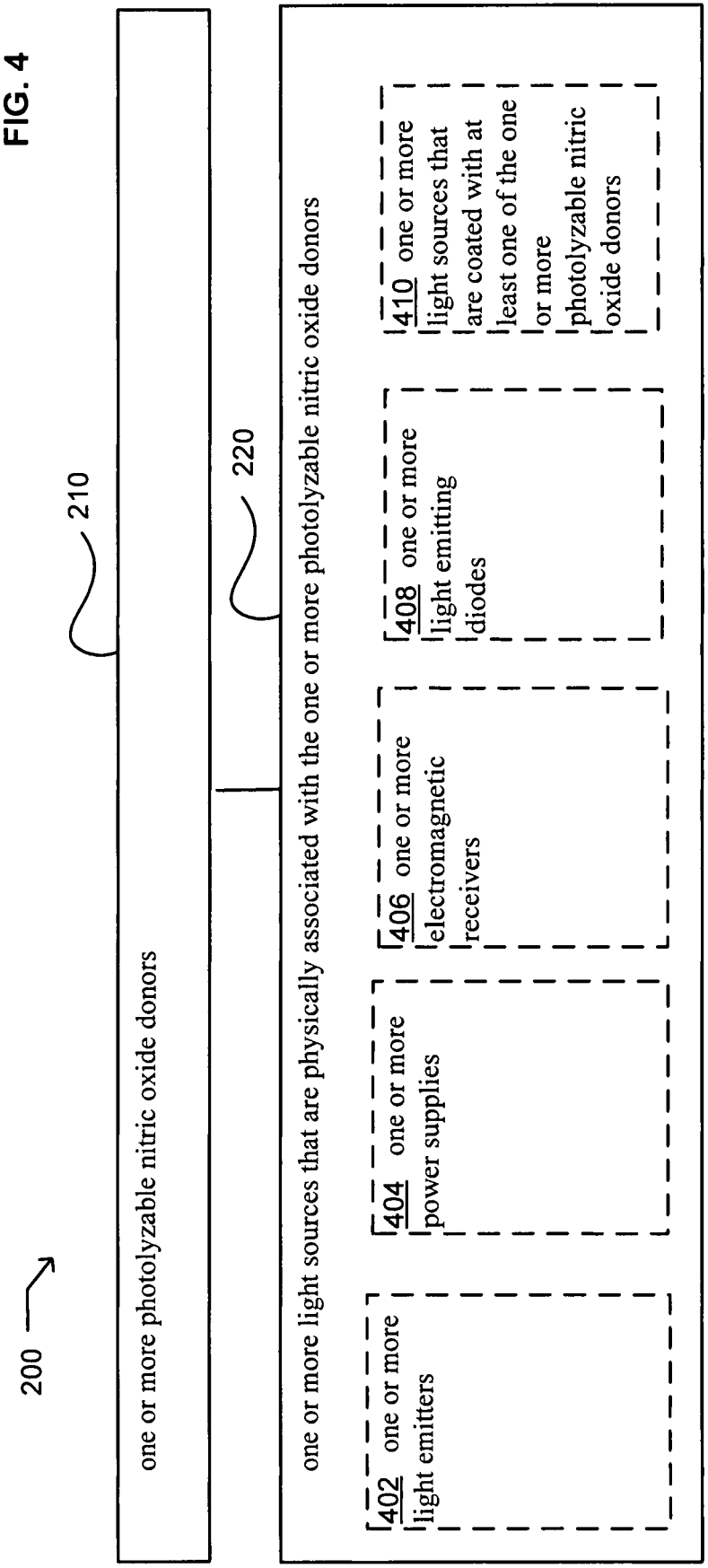
FIG. 4 illustrates alternate embodiments of embodiment 200 of device 102 within system 100.

FIG. 4 illustrates alternative embodiments of embodiment 200 of device 102 within system 100 of FIG. 2. FIG. 4 illustrates example embodiments of module 220. Additional embodiments may include an embodiment 402, an embodiment 404, an embodiment 406, an embodiment 408, and/or an embodiment 410.

At embodiment 402, module 220 may include one or more light emitters. In some embodiments, one or more light sources 106 may include one or more light emitters. Numerous types of light emitters may be associated with one or more light sources 106. Examples of such light emitters include, but are not limited to, light emitting diodes, filaments, arc lamps, fluorescent light emitters, phosphorescent light emitters, chemiluminescent emitters, and the like. In some embodiments, one or more light emitters may be coupled with one or more quantum dots. In some embodiments, one or more light emitters may be coupled with one or more rare-earth materials.

At embodiment 404, module 220 may include one or more power supplies. In some embodiments, one or more light sources 106 may include one or more power supplies. Numerous types of power supplies may be associated with one or more light sources 106. Examples of such power supplies include, but are not limited to, batteries (e.g., thin film batteries), electromagnetic receivers 108, line power, and the like.

At embodiment 406, module 220 may include one or more electromagnetic receivers. In some embodiments, one or more light sources 106 may include one or more electromagnetic receivers 108. In some embodiments, one or more electromagnetic receivers 108 may be used to receive electromagnetic energy 110 for use in providing power to one or more light emitters. Methods to construct electromagnetic receivers 108 have been described (e.g., U.S. Pat. No. 5,571,152).

At embodiment 408, module 220 may include one or more light emitting diodes. In some embodiments, one or more light sources 106 may include one or more light emitting diodes. One or more light sources 106 may include one or more light emitting diodes that are configured to emit light of select wavelengths. For example, light emitting diodes may be configured to emit infrared light, visible light, near-ultraviolet light, or ultraviolet light. In some embodiments, a light source 106 may include a conventional light emitting diode that can include a variety of inorganic semiconductor materials. Examples of such materials and the emitting light include, but are not limited to, aluminium gallium arsenide (red and infrared), aluminium gallium phosphide (green), aluminium gallium indium phosphide (high-brightness orange-red, orange, yellow, and green), gallium arsenide phosphide (red, orange-red, orange, and yellow), gallium phosphide (red, yellow and green), gallium nitride (green, pure green, emerald green, blue, and white (if it has an AlGaN Quantum Barrier)), indium gallium nitride (near ultraviolet, bluish-green and blue), silicon carbide (blue), silicon (blue), sapphire (blue), zinc selenide (blue), diamond (ultraviolet), aluminium nitride (near to far ultraviolet), aluminium gallium nitride (near to far ultraviolet), aluminium gallium indium nitride (near to far ultraviolet).

At embodiment 410, module 220 may include one or more light sources that are coated with at least one of the one or more photolyzable nitric oxide donors. In some embodiments, one or more light sources 106 may be coated with at least one photolyzable nitric oxide donor 104. For example, in some embodiments, a light source 106 may be configured as a wand that emits light which can be coated with one or more photolyzable nitric oxide donors 104. In some embodiments, a light source 106 may be configured as a sheet that is coated with one or more photolyzable nitric oxide donors 104. In some embodiments, one or more light sources 106 may be partially coated with one or more photolyzable nitric oxide donors 104.

Figure 4A:
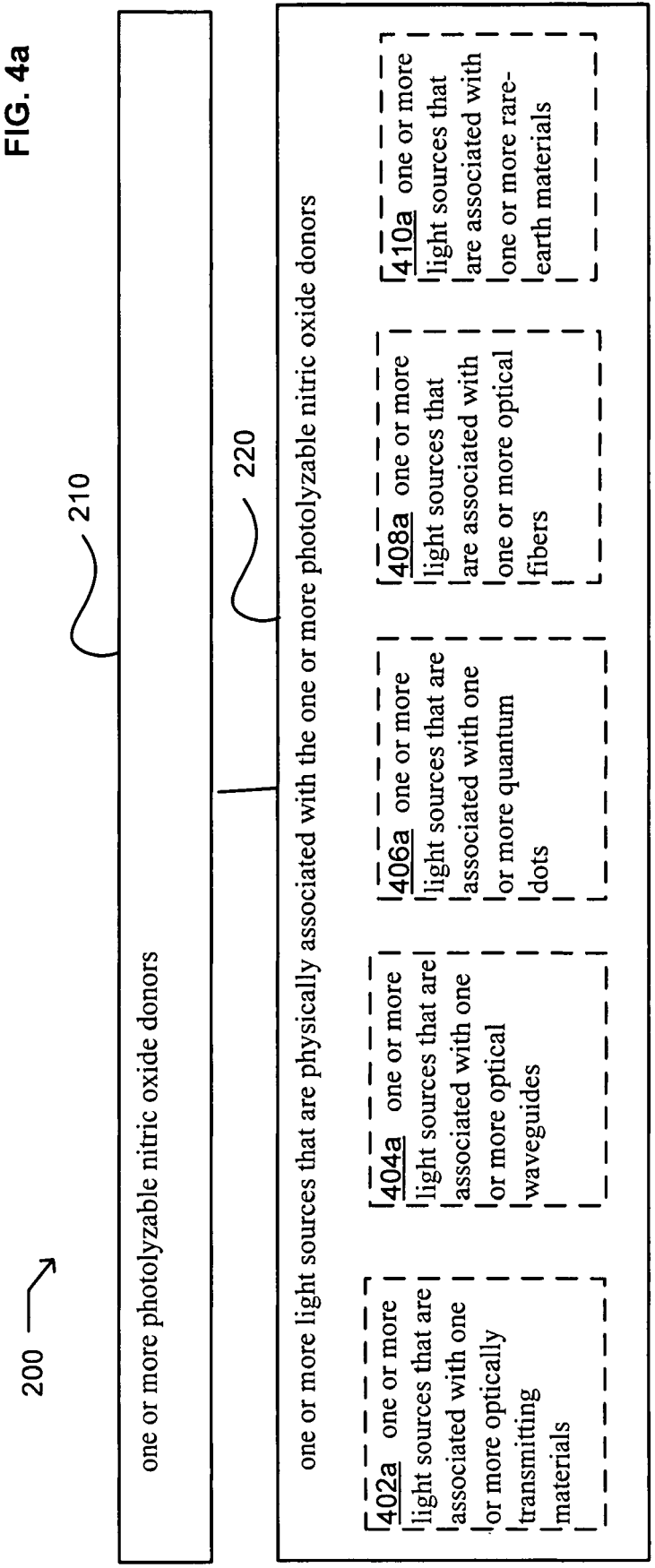
FIG. 4a illustrates alternate embodiments of embodiment 200 of device 102 within system 100.

FIG. 4a illustrates alternative embodiments of embodiment 200 of device 102 within system 100 of FIG. 2. FIG. 4a illustrates example embodiments of module 220. Additional embodiments may include an embodiment 402a, an embodiment 404a, an embodiment 406a, an embodiment 408a, and/or an embodiment 410a.

At embodiment 402a, module 220 may include one or more light sources that are associated with one or more optically transmitting materials. In some embodiments, one or more light sources 106 may be associated with one or more optically transmitting materials. In some embodiments, optically transmitting materials include all substances that function to alter or control electromagnetic radiation in the ultraviolet, visible, or infrared spectral regions. Such materials may be fabricated into optical elements such as lenses, mirrors, windows, prisms, polarizers, detectors, and modulators. These materials may refract, reflect, transmit, disperse, polarize, detect, and/or transform light. Examples of optically transmitting materials include, but are not limited to, glass, crystalline materials, polymers, plastics, and the like. In some embodiments, one or more light sources 106 may include fused silica which transmits to about 180 nm. In some embodiments, one or more light sources 106 may include calcium fluoride which transmits into the ultraviolet region to about 140 nm. Accordingly, a light source 106 may include numerous types of optically transmitting materials.

At embodiment 404a, module 220 may include one or more light sources that are associated with one or more optical waveguides. In some embodiments, one or more light sources 106 may be associated with one or more optical waveguides. Numerous types of optical waveguides may be associated with one or more light sources 106. For example, in some embodiments, a waveguide may be an optical fiber waveguide. In some embodiments, a waveguide may be a rectangular waveguide. In some embodiments, a waveguide may be a dielectric slab waveguide. In some embodiments, optical waveguides may include, but are not limited to, planar waveguides, strip waveguides, and/or fiber waveguides. In some embodiments, an optical waveguide may have a single-mode structure. In some embodiments, an optical waveguide may have a multi-mode structure. In some embodiments, an optical waveguide may exhibit a step refractive index distribution. In some embodiments, an optical waveguide may exhibit a gradient refractive index distribution. An optical waveguide may be constructed from numerous types of materials that include, but are not limited to, glass, polymers, semiconductors, and the like. Methods to construct optical waveguides have been described (e.g., U.S. Pat. No. 7,283,710).

At embodiment 406a, module 220 may include one or more light sources that are associated with one or more quantum dots. In some embodiments, one or more light sources 106 may be associated with one or more quantum dots (e.g., U.S. Pat. No. 7,235,361; herein incorporated by reference). For example, in some embodiments, one or more light sources 106 may be configured to emit one or more wavelengths of light that are absorbed by one or more quantum dots. In some embodiments, one or more quantum dots may be configured to absorb light and then emit one or more wavelengths of light that cause release of nitric oxide from one or more nitric oxide donors. Accordingly, in some embodiments, emission from one or more first quantum dots may be tuned to facilitate release of nitric oxide from one or more first photolyzable nitric oxide donors 104 and emission from one or more second quantum dots may be tuned to facilitate release of nitric oxide from one or more second photolyzable nitric oxide donors 104.

At embodiment 408a, module 220 may include one or more light sources that are associated with one or more optical fibers. In some embodiments, one or more photolyzable nitric oxide donors 104 may be associated with one or more optical fibers. In some embodiments, one or more photolyzable nitric oxide donors 104 may be directly associated with one or more optical fibers. For example, in some embodiments, one or more optical fibers may be directly coated with one or more photolyzable nitric oxide donors 104. In some embodiments, one or more optical fibers may be directly coated with one or more compositions that include one or more photolyzable nitric oxide donors 104.

In some embodiments, one or more portions of one or more optical fibers may be directly coated with one or more photolyzable nitric oxide donors 104. In some embodiments, one or more portions of one or more optical fibers may be directly coated with one or more compositions that include one or more photolyzable nitric oxide donors 104. In some embodiments, one or more photolyzable nitric oxide donors 104 may be indirectly associated with one or more optical fibers. For example, in some embodiments, one or more optical fibers may be inserted into a structure that is coated with one or more photolyzable nitric oxide donors 104. In some embodiments, one or more optical fibers may be inserted into a structure that is coated with one or more compositions that include one or more photolyzable nitric oxide donors 104. In some embodiments, one or more optical fibers may be inserted into a structure that is partially coated with one or more photolyzable nitric oxide donors 104. In some embodiments, one or more optical fibers may be inserted into a structure that is partially coated with one or more compositions that include one or more photolyzable nitric oxide donors 104. For example, in some embodiments, one or more optical fibers may be inserted into one or more tubes that are coated with one or more photolyzable nitric oxide donors 104. In some embodiments, one or more optical fibers may be inserted into one or more tubes that are coated with one or more compositions that include one or more photolyzable nitric oxide donors 104. One or more photolyzable nitric oxide donors 104 may be associated with numerous types of optical fibers. Methods to construct optical fibers have been described. Examples of optical fibers include, but are not limited to, optical fibers that include a single core and/or one or more cores. In some embodiments, an optical fiber may include silica glass. In some embodiments, an optical fiber may include a cladding. Optical fibers have been described (e.g., U.S. Pat. Nos. 7,295,741; 7,295,737).

At embodiment 410a, module 220 may include one or more light sources that are associated with one or more rare-earth materials. In some embodiments, one or more light sources 106 may include one or more photolyzable nitric oxide donors 104 that are associated with one or more rare-earth materials. In some embodiments, one or more rare-earth materials may include one or more rare-earth elements. The rare-earth elements are a collection of sixteen chemical elements in the periodic table, namely scandium, yttrium, and fourteen of the fifteen lanthanoids (excluding promethium). In some embodiments, one or more rare-earth materials may include one or more rare-earth elements that fluoresce.

Figure 5:
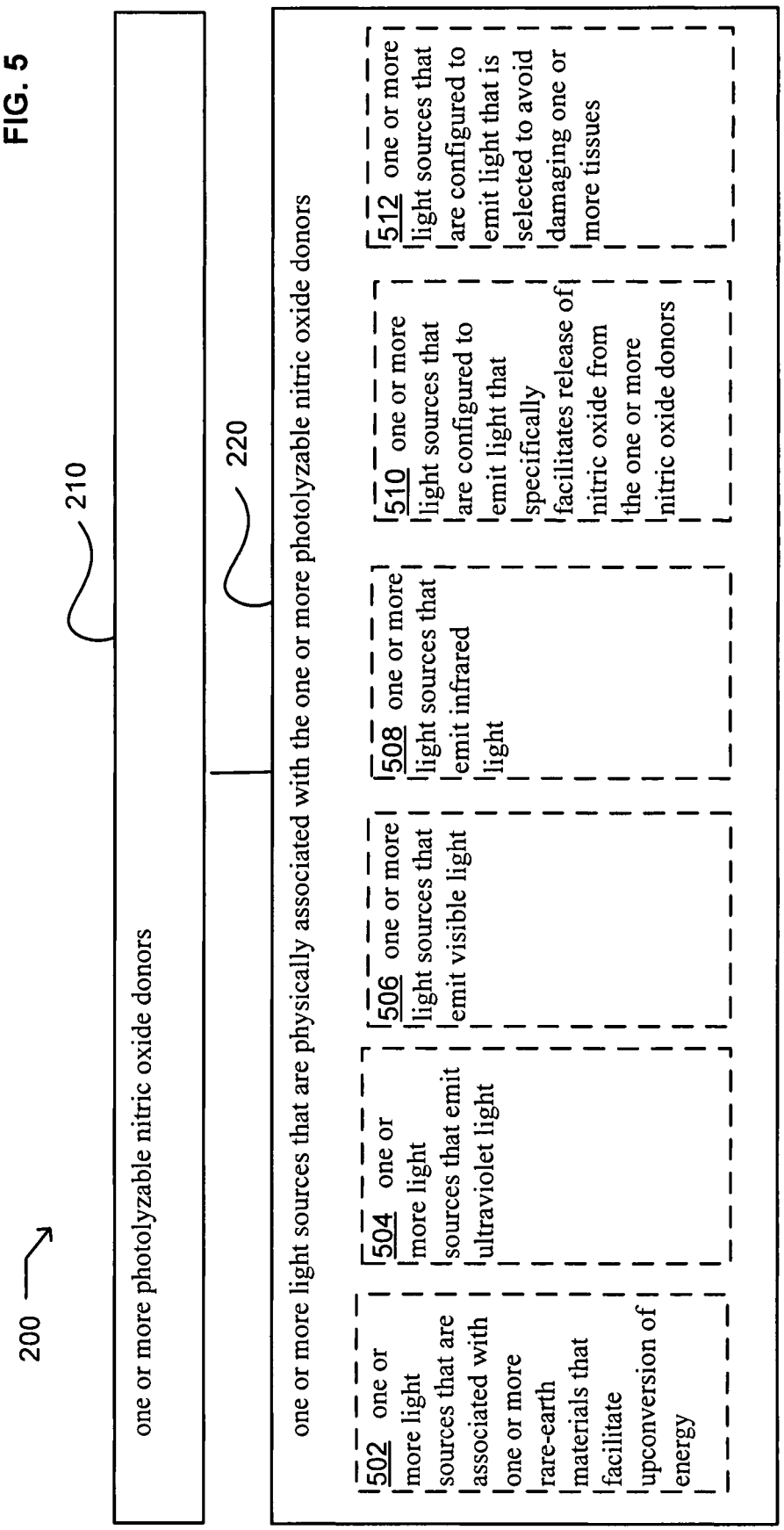
FIG. 5 illustrates alternate embodiments of embodiment 200 of device 102 within system 100.

FIG. 5 illustrates alternative embodiments of embodiment 200 of device 102 within system 100 of FIG. 2. FIG. 5 illustrates example embodiments of module 220. Additional embodiments may include an embodiment 502, an embodiment 504, an embodiment 506, an embodiment 508, an embodiment 510, and/or an embodiment 512.

At embodiment 502, module 220 may include one or more light sources that are associated with one or more rare-earth materials that facilitate upconversion of energy. In some embodiments, one or more light sources 106 may be associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 106 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 106 may be associated with Nd3+ doped KPb2Cl5 crystals. In some embodiments, one or more light sources 106 may be associated with thiogallates doped with rare earths, such as CaGa2S4:Ce3+ and SrGa2S4:Ce3+. In some embodiments, one or more light sources 106 may be associated with aluminates that are doped with rare earths, such as YAlO3:Ce3+, YGaO3:Ce3+, Y(Al,Ga)O3:Ce3+, and orthosilicates M2SiO5:Ce3+ (M:Sc, Y, Sc) doped with rare earths, such as, for example, Y2SiO5:Ce3+. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 504, module 220 may include one or more light sources that emit ultraviolet light. In some embodiments, one or more light sources 106 may emit ultraviolet light. In some embodiments, one or more light sources 106 may emit a broad spectrum of ultraviolet light. In some embodiments, one or more light sources 106 may emit a narrow spectrum of ultraviolet light. In some embodiments, one or more light sources 106 that emit one or more wavelengths of ultraviolet light that are specifically selected to release nitric oxide from one or more photolyzable nitric oxide donors 104. In some embodiments, one or more light sources 106 may emit ultraviolet light that does not include one or more wavelengths of light. In some embodiments, one or more light sources 106 may emit ultraviolet light that is selected to avoid and/or reduce damage to structures and/or tissues of an individual 126. For example, in some embodiments, one or more light sources 106 may emit ultraviolet light that does not include wavelengths of light that are absorbed by nucleic acids. In some embodiments, one or more light sources 106 may emit ultraviolet light that does not include wavelengths of light that are absorbed by polypeptides. In some embodiments, one or more light sources 106 may emit light that does not include one or more wavelengths of ultraviolet light within the following range: 250-320 nm. For example, in some embodiments, one or more light sources 106 may not emit 260 nm light. In some embodiments, one or more light sources 106 may not emit 280 nm light. In some embodiments, one or more light sources 106 may not emit 260 nm light or 280 nm light. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof.

At embodiment 506, module 220 may include one or more light sources that emit visible light. In some embodiments, one or more light sources 106 may emit visible light. In some embodiments, one or more light sources 106 may emit a broad spectrum of visible light. In some embodiments, one or more light sources 106 may emit a narrow spectrum of visible light. In some embodiments, one or more light sources 106 may emit one or more wavelengths of visible light that are specifically selected to release nitric oxide from one or more photolyzable nitric oxide donors 104. In some embodiments, one or more light sources 106 may emit visible light that does not include one or more wavelengths of light. In some embodiments, one or more light sources 106 may emit visible light that is selected to avoid and/or reduce damage to structures and/or tissues of an individual 126. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the visible light may be upconverted.

At embodiment 508, module 220 may include one or more light sources that emit infrared light. In some embodiments, one or more light sources 106 may emit infrared light. In some embodiments, one or more light sources 106 may emit a broad spectrum of infrared light. In some embodiments, one or more light sources 106 may emit a narrow spectrum of infrared light. In some embodiments, one or more light sources 106 may emit one or more wavelengths of infrared light that are specifically selected to release nitric oxide from one or more photolyzable nitric oxide donors 104. In some embodiments, one or more light sources 106 may emit infrared light that does not include one or more wavelengths of light. In some embodiments, one or more light sources 106 may emit infrared light that is selected to avoid and/or reduce damage to structures and/or tissues of an individual 126. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the infrared light may be upconverted.

At embodiment 510, module 220 may include one or more light sources that are configured to emit light that specifically facilitates release of nitric oxide from the one or more nitric oxide donors. In some embodiments, one or more light sources 106 may emit light that specifically facilitates release of nitric oxide from the one or more nitric oxide donors. For example, in some embodiments, one or more light sources 106 may be configured to emit light that includes one or more wavelengths of light that correspond to the absorption maximum for one or more nitric oxide donors. Examples of nitric oxide donors and their associated $\lambda_{max}$ (nm) are provided in Table I below. Accordingly, one or more light sources 106 may be configured to emit numerous wavelengths of light.

TABLE I

Example Nitric Oxide Donors

| Compound Name | $\lambda_{max}$ (nm) |
|---|---|
| $O^2$-(Acetoxymethyl) 1-(N,N-Diethylamino)diazen-1-ium-1,2-diolate | 230 |
| $O^2$-(Acetoxymethyl) 1-(Pyrrolidin-1-yl)diazen-1-ium-1,2-diolate | 256 |
| Sodium 1-(N-Benzyl-N-methylamino)diazen-1-ium-1,2-diolate | 252 |
| $O^2$-[(2,3,4,6-Tetra-O-acetyl)-β-D-glucosyl] 1-[4-(2,3-Dihydroxypropyl)piperazin-1 | 232 |
| Sodium 1-[4-(2,3-Dihydroxypropyl)piperazin-1-yl-]diazen-1-ium-1,2-diolate | 248.5 |
| $O^2$-Methyl 1-[(4-Carboxamido)piperidin-1-yl]diazen-1-ium-1,2-diolate | 241 |
| $O^2$-(2-Chloropyrimidin-4-yl) 1-(Pyrrolidin-1-yl)diazen-1-ium-1,2-diolate | 274 |
| $O^2$-(2,4-Dinitrophenyl) 1-[4-(N,N-Diethylcarboxamido)piperazin-1-yl]diazen-1-ium-1,2-diolate | 300 |
| $O^2$-(2,4-Dinitrophenyl) 1-(4-Nicotinylpiperazin-1-yl)diazen-1-ium-1,2-diolate | 300 |
| $O^2$-(2,4-Dinitrophenyl) 1-{4-[2-(4-{2-Methylpropyl}phenyl)propionyl]piperazin-1-yl}diazen-1-ium-1,2-diolate | 300 |
| Sodium 1-(4-Benzyloxycarbonylpiperazin-1-yl)diazen-1-ium-1,2-diolate | 252 |
| $O^2$-(2,4-Dinitrophenyl) 1-[4-(tert-Butoxycarbonyl)piperazin-1-yl]diazen-1-ium-1,2-diolate | 299 |
| $O^2$-(2,4-Dinitrophenyl) 1-(4-Acetylpiperazin-1-yl)diazen-1-ium-1,2-diolate | 394 |
| $O^2$-(2,4-Dinitrophenyl) 1-[4-(Succinimidoxycarbonyl)piperazin-1-yl]diazen-1-ium-1,2-diolate | 300 |
| $O^2$-(2,4-Dinitrophenyl) 1-(Piperazin-1-yl)diazen-1-ium-1,2-diolate, Hydrochloride Salt | 297 |
| $O^2$-(2,3,4,6-Tetra-O-acetyl-D-glucopyranosyl) 1-(N,N-Diethylamino)diazen-1-ium-1,2-diolate | 228 |
| $O^2$-(-D-Glucopyranosyl) 1-(N,N-Diethylamino)diazen-1-ium-1,2-diolate | 228 |
| Sodium (Z)-1-(N,N-Diethylamino)diazen-1-ium-1,2-diolate | 250 |
| 1-[N-(2-Aminoethyl)-N-(2-ammonioethyl)amino]diazen-1-ium-1,2-diolate | 252 |
| Sodium 1-(N,N-Dimethylamino)diazen-1-ium-1,2-diolate | 250 |
| $O^2$-(2,4-Dinitrophenyl) 1-(N,N-Diethylamino)diazen-1-ium-1,2-diolate | 302 |
| 1-[N-(3-Aminopropyl)-N-(3-ammoniopropyl]diazen-1-ium-1,2-diolate | 252 |
| 1-[N-(3-Aminopropyl)-N-(3-ammoniopropyl]diazen-1-ium-1,2-diolate | 252 |
| Bis-diazeniumdiolated benzyl imidate dehydrate | 264 |
| p-Bisdiazeniumdiolated benzene | 316 |
| Methane Trisdiazeniumdiolate trihydrate | 316 |
| $O^2$-(β-D-Glucopyranosyl) 1-(Isopropylamino)diazen-1-ium-1,2-diolate | 278 |
| Sodium 1-[4-(5-Dimethylamino-1-naphthalenesulfonyl)piperazin-1-yl]diazen-1-ium-1,2-diolate | 344 |
| 1-(2-Methyl-1-propenyl)piperidine diazeniumdiolate | 246 |
| 1-(2-Methyl-1-propenyl)pyrrolidine diazeniumdiolate | 246 |
| $O^2$-Vinyl 1-(Pyrrolidin-1-yl)diazen-1-ium-1,2-diolate | 268 |
| 1-{N-[3-Aminopropyl]-N-[4-(3-aminopropylammoniobutyl)]}diazen-1-ium-1,2-diolate | 252 |
| Disodium 1-[(2-Carboxylato)pyrrolidin-1-yl]diazen-1-ium-1,2-diolate | 252 |
| 1-[N-(3-Ammoniopropyl)-N-(n-propyl)amino]diazen-1-ium-1,2-diolate | 250 |
| (Z)-1-{N-Methyl-N-[6-(N-methylammoniohexyl)amino]}diazen-1-ium-1,2-diolate | 250 |
| $O^2$-(2,4-Dinitrophenyl) 1-[(4-Ethoxycarbonyl)piperazin-1-yl]diazen-1-ium-1,2-diolate | 300 |

At embodiment 512, module 220 may include one or more light sources that are configured to emit light that is selected to avoid damaging one or more tissues. In some embodiments, one or more light sources 106 may be configured to emit light that is selected to avoid damaging one or more tissues. In some embodiments, one or more light sources 106 may emit light that is selected to avoid and/or reduce damage to structures and/or tissues of an individual 126. For example, in some embodiments, one or more light sources 106 may emit light that does not include wavelengths of light that are absorbed by nucleic acids. In some embodiments, one or more light sources 106 may emit light that does not include wavelengths of light that are absorbed by polypeptides. In some embodiments, one or more light sources 106 may emit light that does not include one or more wavelengths of light within the following range: 250-320 nm. For example, in some embodiments, one or more light sources 106 may not emit 260 nm light. In some embodiments, one or more light sources 106 may not emit 280 nm light. In some embodiments, one or more light sources 106 may not emit 260 nm light or 280 nm light. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse.

Figure 6:
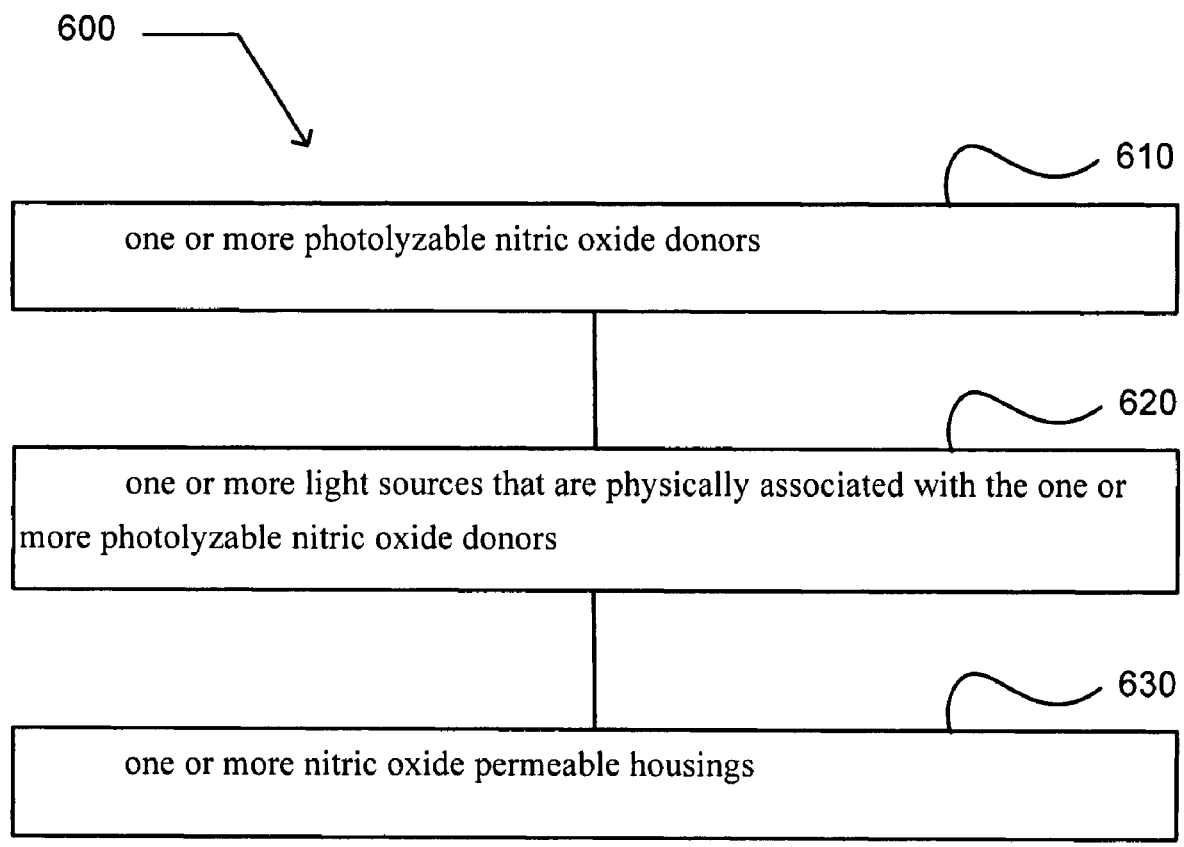
FIG. 6 illustrates embodiment 600 of device 102 within system 100.

FIG. 6 illustrates alternative embodiment 600 of device 102 within system 100 of FIG. 1. In FIG. 6, discussion and explanation may be provided with respect to the above-described example of FIG. 1, and/or with respect to other examples and contexts. In some embodiments, modules 210 and 220 as described with respect to embodiment 200 of device 102 of FIG. 2 may correspond to modules 610 and 620 as described with respect to embodiment 600 of device 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 600 includes module 610 that includes one or more photolyzable nitric oxide donors. In some embodiments, device 102 includes one or more photolyzable nitric oxide donors 104 that release nitric oxide upon photolysis. Examples of such photolyzable nitric oxide donors 104 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 600 includes module 620 that includes one or more light sources that are physically associated with the one or more photolyzable nitric oxide donors. In some embodiments, device 102 includes one or more light sources 106 that are physically associated with one or more photolyzable nitric oxide donors 104. In some embodiments, the one or more light sources 106 may be directly coupled to one or more photolyzable nitric oxide donors 104. For example, in some embodiments, the one or more photolyzable nitric oxide donors 104 may be chemically coupled to a surface of the light source 106 (e.g., chemically coupled to a polymer coating on the light source). In some embodiments, one or more photolyzable nitric oxide donors 104 may be indirectly coupled to one or more light sources 106. For example, in some embodiments, one or more photolyzable nitric oxide donors 104 may be coupled to a material that is used to coat the one or more light sources 106.

The embodiment 600 includes module 630 that includes one or more nitric oxide permeable housings. In some embodiments, device 102 may include one or more nitric oxide permeable housings 114. In some embodiments, nitric oxide permeable housings 114 may be configured for implantation within an individual 126. In some embodiments, nitric oxide permeable housings 114 may be configured to facilitate application of nitric oxide to a surface. In some embodiments, one or more nitric oxide permeable housings 114 may be configured to facilitate application of nitric oxide to one or more surfaces of an individual 126. For example, in some embodiments, one or more nitric oxide permeable housings 114 may be configured as a canister having a nitric oxide permeable end that may be positioned on a skin surface of an individual to deliver nitric oxide to the skin surface. In some embodiments, one or more nitric oxide permeable housings 114 may be configured for insertion into the urethra of a male. In some embodiments, one or more nitric oxide permeable housings 114 may be configured for insertion into the vagina of a female.

In some embodiments, one or more nitric oxide permeable housings 114 may be configured to enclose at least a portion of one or more photolyzable nitric oxide donors 104. In some embodiments, one or more nitric oxide permeable housings 114 may be configured to enclose at least a portion of one or more light sources 106. In some embodiments, one or more nitric oxide permeable housings 114 may be configured to enclose at least a portion of one or more control units 116. In some embodiments, one or more nitric oxide permeable housings 114 may be configured to enclose at least a portion of one or more nitric oxide sensors 120. In some embodiments, one or more nitric oxide permeable housings 114 may be configured to enclose one or more photolyzable nitric oxide donors 104. In some embodiments, one or more nitric oxide permeable housings 114 may be configured to enclose one or more light sources 106. In some embodiments, one or more nitric oxide permeable housings 114 may be configured to enclose one or more photolyzable nitric oxide donors 104 and one or more light sources 106. In some embodiments, one or more nitric oxide permeable housings 114 may be configured to enclose one or more photolyzable nitric oxide donors 104, one or more light sources 106, and one or more control units 116. In some embodiments, one or more nitric oxide permeable housings 114 may be configured to enclose one or more photolyzable nitric oxide donors 104, one or more light sources 106, one or more control units 116, and one or more electromagnetic receivers 108. In some embodiments, one or more nitric oxide permeable housings 114 may be configured to enclose one or more photolyzable nitric oxide donors 104, one or more light sources 106, one or more control units 116, one or more electromagnetic receivers 108, or substantially any combination thereof. In some embodiments, one or more nitric oxide permeable housings 114 may be configured to include one or more compartments. For example, in some embodiments, a nitric oxide permeable housing 114 may include a compartment that is configured to accept one or more light sources 106 and a second compartment that is configured to accept one or more photolyzable nitric oxide donors 104. In some embodiments, a nitric oxide permeable housing 114 may include a compartment that is configured to accept one or more light sources 106, a light permeable divider, and a second compartment that is configured to accept one or more photolyzable nitric oxide donors 104. In some embodiments, a light permeable divider may be made of a material that allows light to pass through the divider. Examples of such material include, but are not limited to, plastic, quartz, and the like.

Nitric oxide permeable housings 114 may be constructed of numerous types of materials and combinations of materials. Examples of such materials include, but are not limited to, ceramics, polymeric materials, metals, plastics, and the like. In some embodiments, nitric oxide permeable housings 114 may include numerous combinations of materials.

Figure 7:
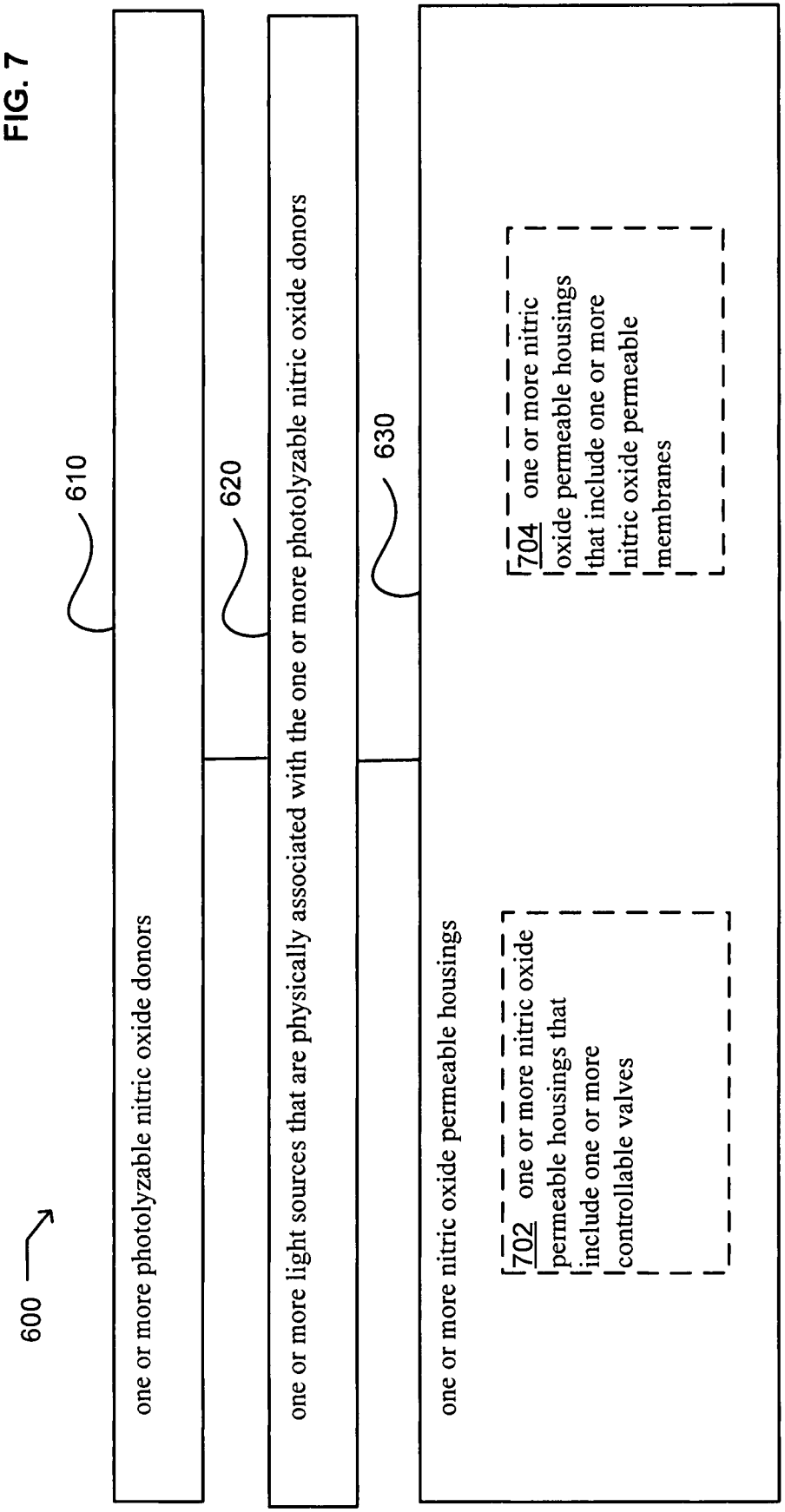
FIG. 7 illustrates alternate embodiments of embodiment 600 of device 102 within system 100.

FIG. 7 illustrates alternative embodiments of embodiment 600 of device 102 within system 100 of FIG. 6. FIG. 7 illustrates example embodiments of module 630. Additional embodiments may include an embodiment 702, and/or an embodiment 704.

At embodiment 702, module 630 may include one or more nitric oxide permeable housings that include one or more controllable valves. In some embodiments, one or more nitric oxide permeable housings 114 may include one or more controllable valves. In some embodiments, a controllable valve may provide for the passage of nitric oxide. In some embodiments, a controllable valve may provide for the passage of one or more photolyzable nitric oxide donors 104. In some embodiments, one or more controllable valves may include one or more electromagnets that provide for controlled opening and closing of an orifice associated with the valve. In some embodiments, one or more controllable valves may include one or more screw closures that provide for controlled opening and closing of the valve. For example, in some embodiments, a nitric oxide permeable housing 114 may include an electric motor that operates the screw mechanism to provide for opening and closure of an orifice associated with the nitric oxide permeable housing 114. Numerous controllable valves may be associated with one or more nitric oxide permeable housings 114. In some embodiments, a nitric oxide permeable housing 114 may include one or more valves that are controllable by one or more control units 116. Accordingly, in some embodiments, valves may be opened or closed in response to one or more nitric oxide sensors 120, one or more signals 118, one or more information packets, one or more management units 122, or substantially any combination thereof.

At embodiment 704, module 630 may include one or more nitric oxide permeable housings that include one or more nitric oxide permeable membranes. In some embodiments, one or more nitric oxide permeable housings 114 may include one or more nitric oxide permeable membranes. For example, in some embodiments, a nitric oxide permeable housing 114 may include a nitric oxide impermeable metal canister that is coupled to a nitric oxide permeable membrane (e.g., U.S. Patent Application No. 20020026937). In some embodiments, a nitric oxide permeable housing 114 may include a selectively permeable membrane. For example, in some embodiments, a nitric oxide permeable housing 114 may include a selectively permeable, hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable housing 114 may include a scintered glass portion that is permeable to nitric oxide. Accordingly, nitric oxide permeable housings 114 may include numerous types of porous ceramics that are permeable to nitric oxide. In some embodiments, a nitric oxide permeable housing 114 may include a nitric oxide permeable coating (e.g., U.S. Patent Application Nos. 20050220838; 20030093143).

Figure 8:
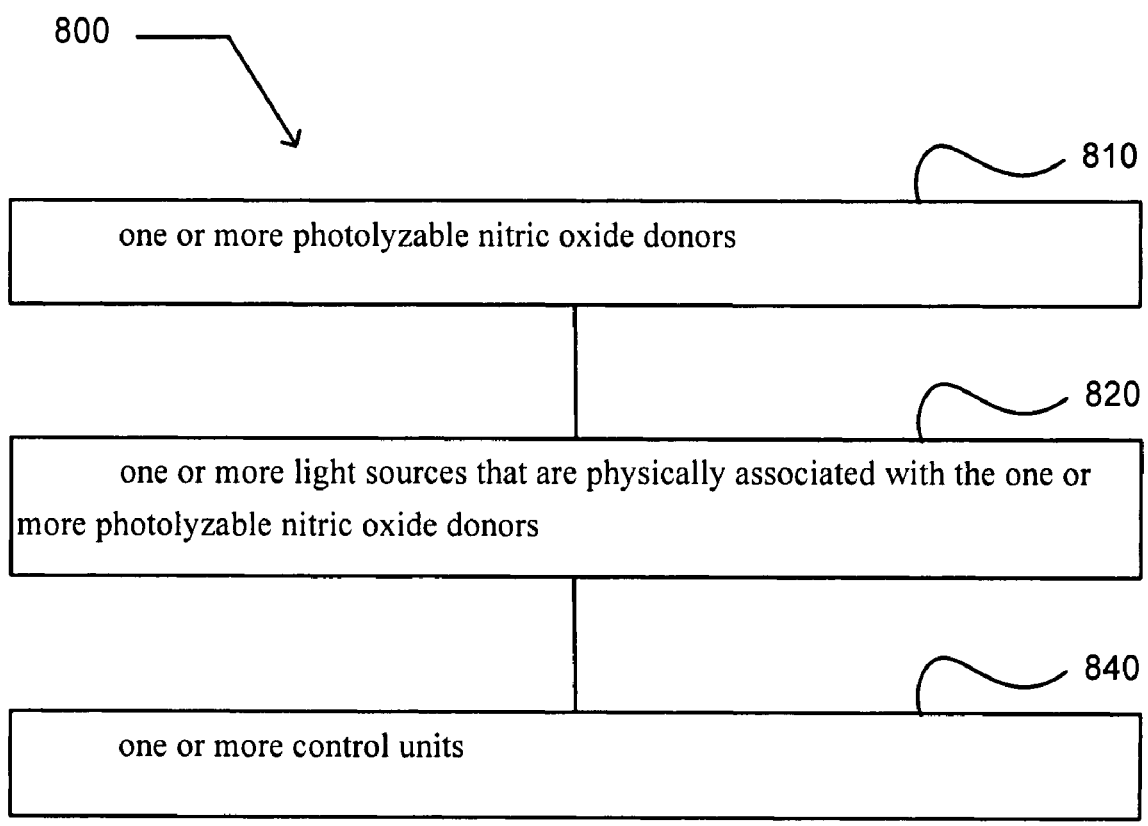
FIG. 8 illustrates embodiment 800 of device 102 within system 100.

FIG. 8 illustrates alternative embodiment 800 of device 102 within system 100 of FIG. 1. In FIG. 8, discussion and explanation may be provided with respect to the above-described example of FIG. 1, and/or with respect to other examples and contexts. In some embodiments, modules 210 and 220 as described with respect to embodiment 200 of device 102 of FIG. 2 may correspond to modules 810 and 820 as described with respect to embodiment 800 of FIG. 8. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 800 includes module 810 that includes one or more photolyzable nitric oxide donors. In some embodiments, a device 102 includes one or more photolyzable nitric oxide donors 104 that release nitric oxide upon photolysis. Examples of such photolyzable nitric oxide donors 104 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 800 includes module 820 that includes one or more light sources that are physically associated with the one or more photolyzable nitric oxide donors. In some embodiments, device 102 includes one or more light sources 106 that are physically associated with one or more photolyzable nitric oxide donors 104. In some embodiments, the one or more light sources 106 may be directly coupled to one or more photolyzable nitric oxide donors 104. For example, in some embodiments, the one or more photolyzable nitric oxide donors 104 may be chemically coupled to a surface of the light source 106 (e.g., chemically coupled to a polymer coating on the light source). In some embodiments, one or more photolyzable nitric oxide donors 104 may be indirectly coupled to one or more light sources 106. For example, in some embodiments, one or more photolyzable nitric oxide donors 104 may be coupled to a material that is used to coat the one or more light sources 106.

The embodiment 800 includes module 840 that includes one or more control units. In some embodiments, device 102 may include one or more control units 116. A device 102 may include numerous types of control units 116. In some embodiments, one or more control units 116 may be operably coupled with one or more light sources 106, one or more nitric oxide sensors 120, one or more electromagnetic receivers 108, one or more electromagnetic transmitters 112, or substantially any combination thereof. In some embodiments, one or more control units 116 may be operably coupled to other components through use of one or more wireless connections, one or more hardwired connections, or substantially any combination thereof. Control units 116 may be configured in numerous ways. For example, in some embodiments, a control unit 116 may be configured as an on/off switch. Accordingly, in some embodiments, a control unit 116 may be configured to turn a light source 106 on and/or off. In some embodiments, a control unit 116 may be configured to control the emission of light from one or more light sources 106. For example, in some embodiments, one or more control units 116 may regulate the intensity of light emitted from one or more light sources 106, the duration of light emitted from one or more light sources 106, the frequency of light emitted from one or more light sources 106, wavelengths of light emitted from one or more light sources 106, or substantially any combination thereof. In some embodiments, one or more control units 116 may be configured to receive one or more signals 118 from one or more nitric oxide sensors 120. Accordingly, in some embodiments, one or more control units 116 may be configured to control one or more light sources 106 in response to one or more signals 118 received from one or more nitric oxide sensors 120. For example, in some embodiments, one or more nitric oxide sensors 120 may sense a low concentration of nitric oxide in one or more tissues and send one or more signals 118 to one or more control units 116. The one or more control units 116 may then turn one or more light sources 106 on to facilitate release of nitric oxide from one or more photolyzable nitric oxide donors 104. Accordingly, in some embodiments, one or more nitric oxide sensors 120 may sense a high concentration of nitric oxide in one or more tissues and send one or more signals 118 to one or more control units 116. The one or more control units 116 may then turn one or more light sources 106 off to end release of nitric oxide from one or more photolyzable nitric oxide donors 104. In some embodiments, one or more control units 116 may be programmed to control one or more light sources 106. For example, in some embodiments, one or more control units 116 may be programmed to turn one or more light sources 106 on for a predetermined amount of time and then turn off. Accordingly, in some embodiments, one or more control units 116 may be preprogrammed. In some embodiments, one or more control units 116 may be dynamically programmed. For example, in some embodiments, one or more management units 122 may receive one or more signals 118 from one or more nitric oxide sensors 120 and program one or more control units 116 in response to the one or more signals 118 received from the one or more nitric oxide sensors 120. In some embodiments, one or more control units 116 may include one or more receivers that are able to receive one or more signals 118, one or more information packets, or substantially any combination thereof. Control units 116 may be configured in numerous ways. For example, in some embodiments, one or more control units 116 may be operably coupled to one or more light sources 106 that include numerous light emitting diodes that emit light of different wavelengths. Accordingly, in some embodiments, one or more control units 116 may control the wavelengths of light emitted by the one or more light sources 106 by controlling the operation of light emitting diodes that emit light of the selected wavelength. Accordingly, control units 116 may be configured in numerous ways and utilize numerous types of mechanisms.

Figure 9:
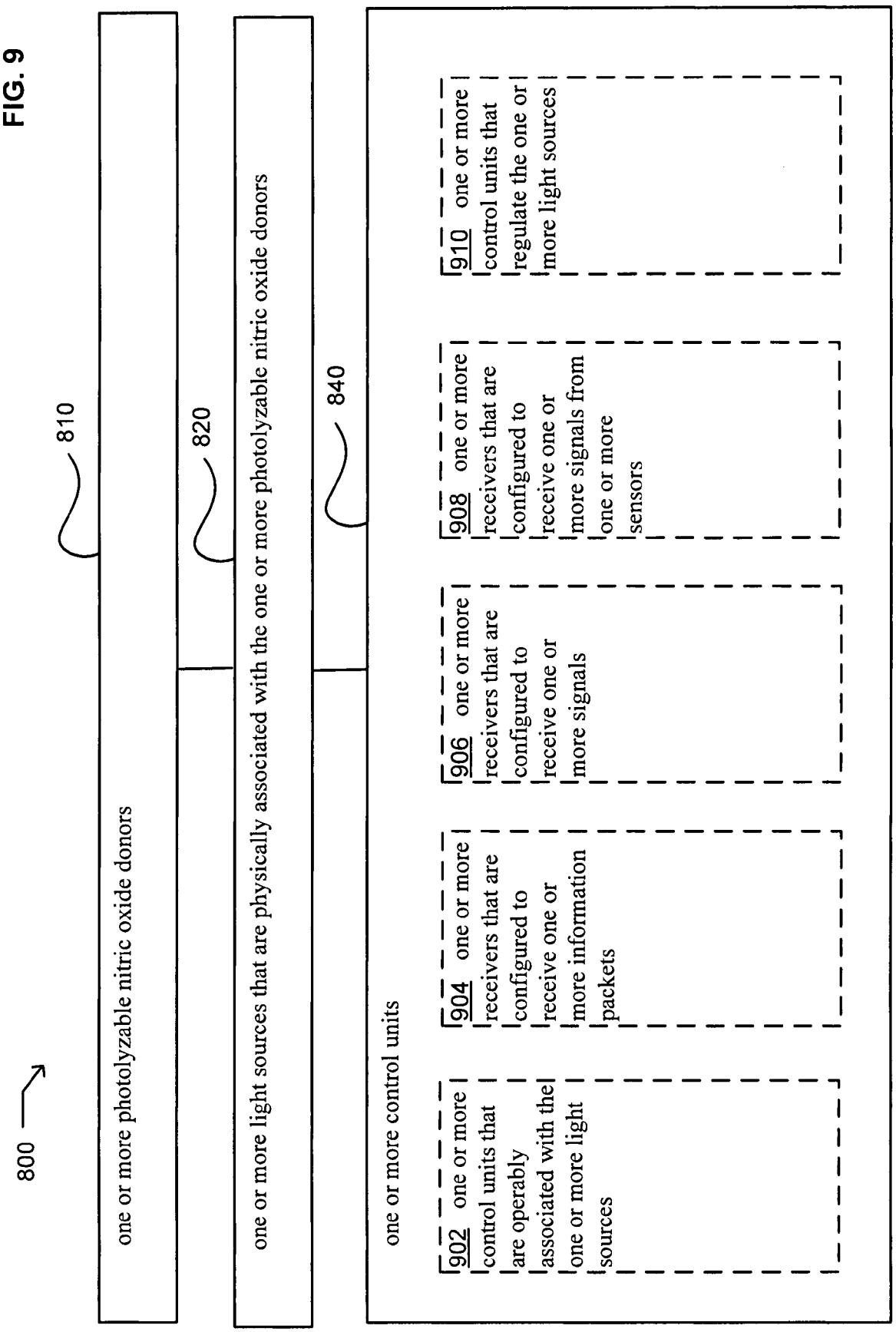
FIG. 9 illustrates alternate embodiments of embodiment 800 of device 102 within system 100.

FIG. 9 illustrates alternative embodiments of embodiment 800 of device 102 within system 100 of FIG. 8. FIG. 9 illustrates example embodiments of module 840. Additional embodiments may include an embodiment 902, an embodiment 904, an embodiment 906, an embodiment 908, and/or an embodiment 910.

At embodiment 902, module 840 may include one or more control units that are operably associated with the one or more light sources. In some embodiments, one or more control units 116 may be operably associated with one or more light sources 106. In some embodiments, the one or more control units 116 may be operably associated with one or more light sources 106 through use of a hardwired connection. In some embodiments, the one or more control units 116 may be operably associated with one or more light sources 106 through use of a wireless connection. In some embodiments, one or more control units 116 may include numerous types of receivers. Examples of such receivers include, but are not limited to, receivers that receive one or more optical signals 118, radio signals 118, wireless signals 118, hardwired signals 118, infrared signals 118, ultrasonic signals 118, and the like. Such receivers are known and have been described (e.g., U.S. Pat. Nos. RE39,785; 7,218,900; 7,254,160; 7,245,894; 7,206,605; herein incorporated by reference).

At embodiment 904, module 840 may include one or more receivers that are configured to receive one or more information packets. In some embodiments, one or more control units 116 may include one or more receivers that are configured to receive one or more information packets. In some embodiments, one or more control units 116 may be configured to receive one or more information packets that include numerous types of information. Examples of such information include, but are not limited to, intensity of light to be emitted by one or more light sources 106, duration of light to be emitted by one or more light sources 106, frequency of light to be emitted by one or more light sources 106, wavelengths of light to be emitted by one or more light sources 106, and the like.

At embodiment 906, module 840 may include one or more receivers that are configured to receive one or more signals. In some embodiments, one or more control units 116 may include one or more receivers that are configured to receive one or more signals 118. A control unit 116 may include a receiver that is configured to receive numerous types of signals 118. Examples of such signals 118 include, but are not limited to, optical signals 118, radio signals 118, wireless signals 118, hardwired signals 118, infrared signals 118, ultrasonic signals 118, and the like. In some embodiments, one or more signals 118 may not be encrypted. In some embodiments, one or more signals 118 may be encrypted. In some embodiments, one or more signals 118 may be sent through use of a secure mode of transmission. In some embodiments, one or more signals 118 may be coded for receipt by a specific individual 126. In some embodiments, such code may include anonymous code that is specific for an individual 126. Accordingly, information included within one or more signals 118 may be protected against being accessed by others who are not the intended recipient.

At embodiment 908, module 840 may include one or more receivers that are configured to receive one or more signals from one or more sensors. In some embodiments, one or more control units 116 may include one or more receivers that are configured to receive one or more signals 118 from one or more sensors. In some embodiments, one or more control units 116 may include one or more receivers that are configured to receive one or more signals 118 from one or more nitric oxide sensors 120. Control units 116 may be configured to receive one or more signals 118 from numerous types of sensor. Examples of such sensors include, but are not limited to, temperature sensors, blood pressure sensors, pulse rate sensors, hydrostatic pressure sensors, clocks, and the like.

At embodiment 910, module 840 may include one or more control units that regulate the one or more light sources. In some embodiments, one or more control units 116 may include one or more control units 116 that regulate one or more light sources 106. One or more control units 116 may regulate numerous aspects of one or more light sources 106. Examples of such aspects include, but are not limited to, intensity of emitted light, duration of emitted light, pulse frequency of emitted light, wavelengths of emitted light, and the like.

Figure 10:
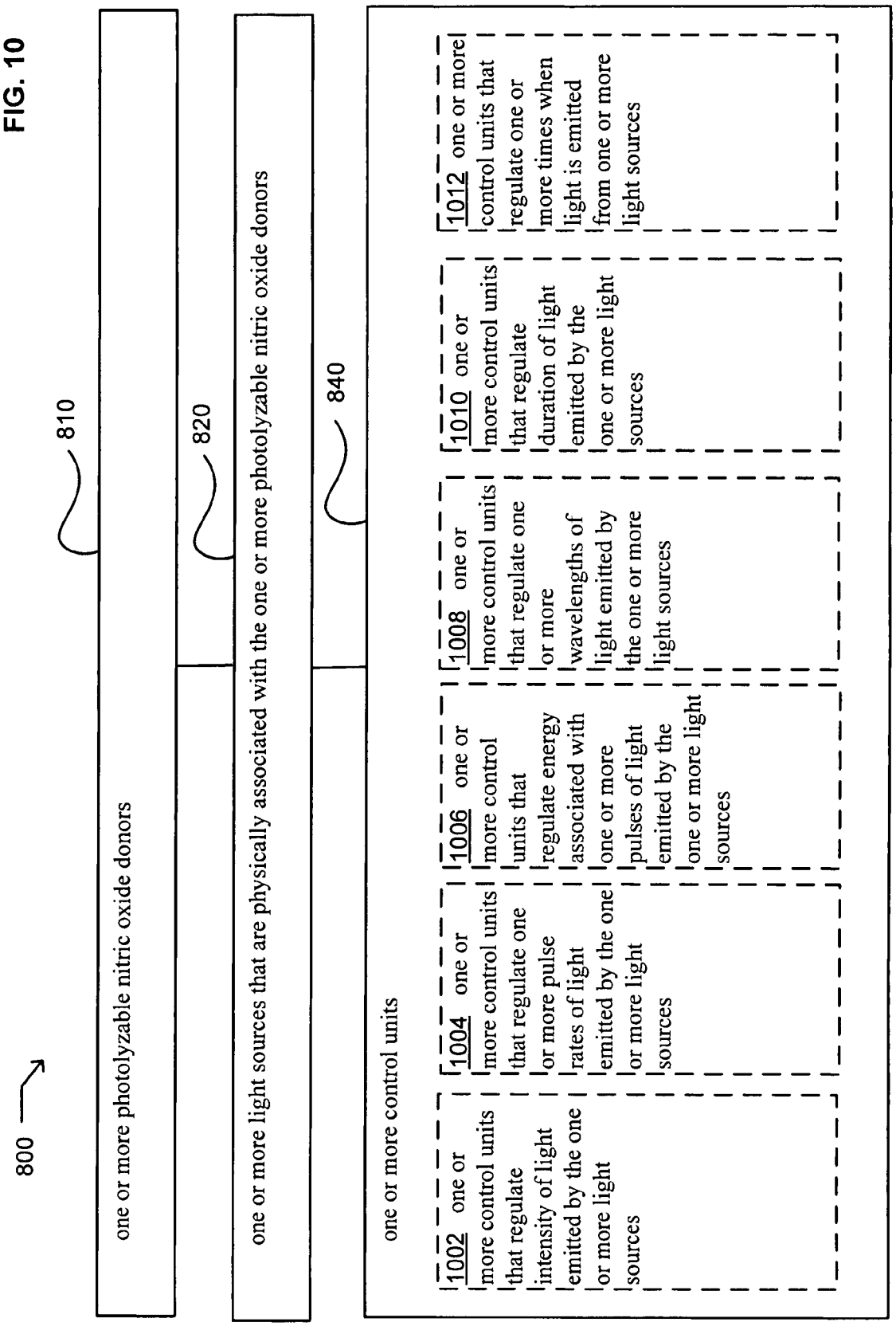
FIG. 10 illustrates alternate embodiments of embodiment 800 of device 102 within system 100.

FIG. 10 illustrates alternative embodiments of embodiment 800 device 102 of FIG. 8. FIG. 10 illustrates example embodiments of module 840. Additional embodiments may include an embodiment 1002, an embodiment 1004, an embodiment 1006, an embodiment 1008, an embodiment 1010, and/or an embodiment 1012.

At embodiment 1002, module 840 may include one or more control units that regulate intensity of light emitted by the one or more light sources. In some embodiments, one or more control units 116 may include one or more control units 116 that regulate the intensity of light emitted by one or more light sources 106. For example, in some embodiments, one or more control units 116 may regulate the current flowing through a light source 106 to regulate the intensity of light emitted from the light source. For example, in some embodiments, one or more control units 116 may include a potentiometer.

At embodiment 1004, module 840 may include one or more control units that regulate one or more pulse rates of light emitted by the one or more light sources. In some embodiments, one or more control units 116 may include one or more control units 116 that regulate one or more pulse rates of light emitted by the one or more light sources 106. For example, in some embodiments, one or more control units 116 may cause a light source 106 to emit light in short pulses (e.g., nanosecond pulses, microsecond pulses). In some embodiments, one or more control units 116 may cause a light source 106 to emit light in medium pulses (e.g., second pulses, minute pulses). In some embodiments, one or more control units 116 may cause a light source 106 to emit light in medium pulses (e.g., hour pulses, day long pulses).

At embodiment 1006, module 840 may include one or more control units that regulate energy associated with one or more pulses of light emitted by the one or more light sources. In some embodiments, one or more control units 116 may include one or more control units 116 that regulate energy associated with one or more pulses of light emitted by the one or more light sources 106. For example, in some embodiments, one or more control units 116 may regulate the current flowing through a light source 106 to regulate the energy associated with one or more pulses of light emitted by the one or more light sources 106. In some embodiments, one or more control units 116 may regulate what wavelengths of light are emitted by a light source 106 to regulate the energy associated with one or more pulses of light emitted by the one or more light sources 106.

At embodiment 1008, module 840 may include one or more control units that regulate one or more wavelengths of light emitted by the one or more light sources. In some embodiments, one or more control units 116 may include one or more control units 116 that regulate one or more wavelengths of light emitted by one or more light sources 106. For example, in some embodiments, one or more control units 116 may be coupled to a light source 106 that includes numerous light emitting diodes that emit light of different wavelengths. Accordingly, in some embodiments, one or more control units 116 may regulate wavelengths of light emitted from the light source 106 by selectively illuminating light emitting diodes that emit the desired wavelengths of light.

At embodiment 1010, module 840 may include one or more control units that regulate duration of light emitted by the one or more light sources. In some embodiments, one or more control units 116 may include one or more control units 116 that regulate the duration of light emitted by one or more light sources 106. For example, one or more control units 116 may cause one or more light sources 106 to emit light for a period of nanoseconds, microseconds, milliseconds, seconds, minutes, hours, days, and the like.

At embodiment 1012, module 840 may include one or more control units that regulate one or more times when light is emitted from one or more light sources. In some embodiments, one or more control units 116 may include one or more control units 116 that regulate one or more times when light is emitted from one or more light sources 106. For example, in some embodiments, one or more control units 116 may facilitate illumination of one or more photolyzable nitric oxide donors 104 at predetermined time intervals. In some embodiments, one or more control units 116 may facilitate illumination of one or more photolyzable nitric oxide donors 104 at predetermined time intervals. In some embodiments, one or more control units 116 may facilitate illumination of one or more photolyzable nitric oxide donors 104 at selected times during the day. Accordingly, one or more control units may regulate one or more times when one or more light sources emit light.

Figure 11:
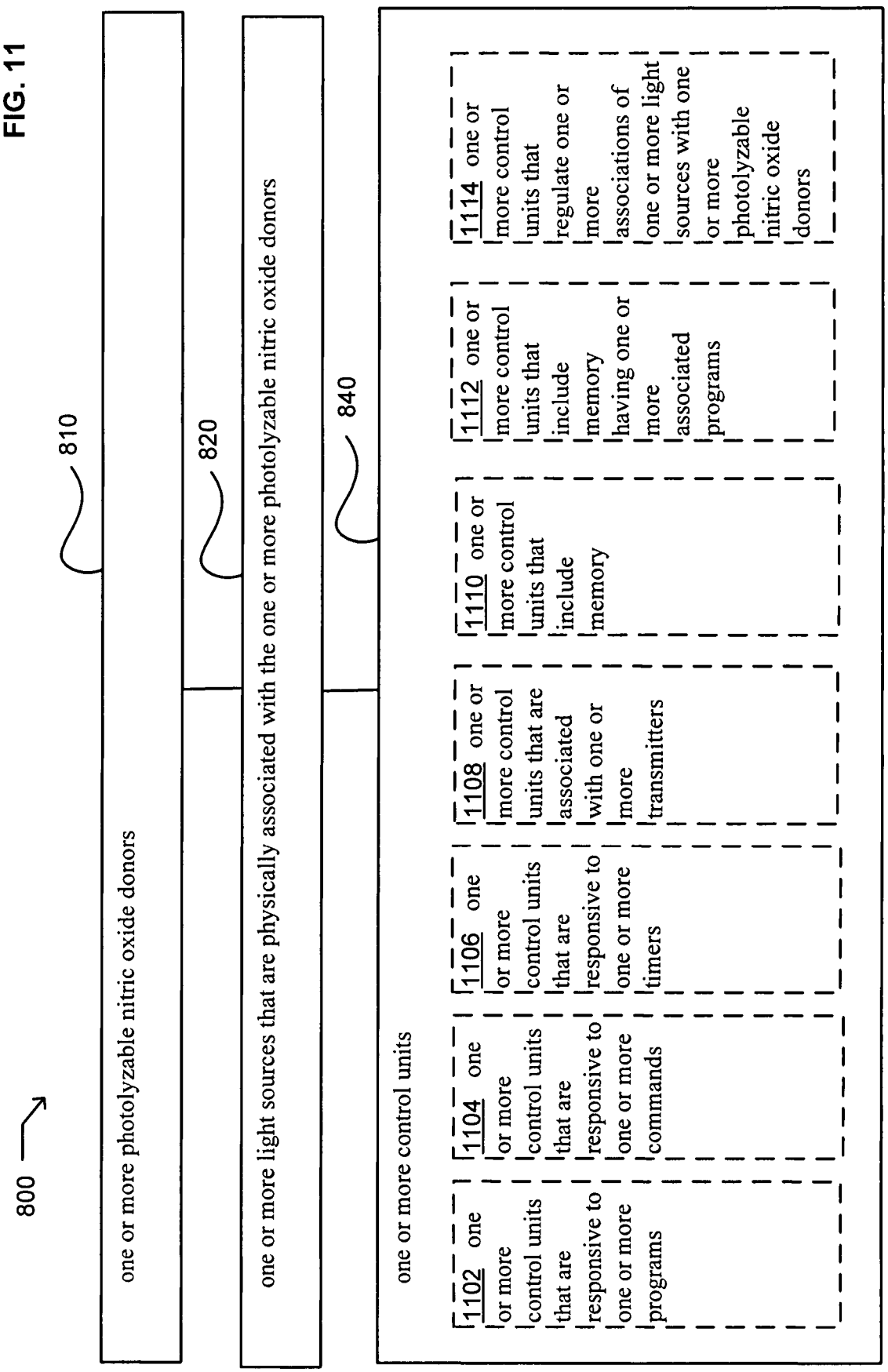
FIG. 11 illustrates alternate embodiments of embodiment 800 of device 102 within system 100.

FIG. 11 illustrates alternative embodiments of embodiment 840 of device 102 of FIG. 8. FIG. 11 illustrates example embodiments of module 840. Additional embodiments may include an embodiment 1102, an embodiment 1104, an embodiment 1106, an embodiment 1108, an embodiment 1110, an embodiment 1112, and/or an embodiment 1114.

At embodiment 1102, module 840 may include one or more control units that are responsive to one or more programs. In some embodiments, one or more control units 116 may include one or more control units 116 that are responsive to one or more programs. For example, in some embodiments, one or more control units 116 may be responsive to a programmed set of instructions. In some embodiments, the one or more control units 116 may be directly programmed. For example, in some embodiments, one or more control units 116 may include a programmable memory that can include instructions. In some embodiments, the one or more control units 116 may receive instructions from a program that is associated with one or more management units 122.

At embodiment 1104, module 840 may include one or more control units that are responsive to one or more commands. In some embodiments, one or more control units 116 may include one or more control units 116 that are responsive to one or more commands. For example, in some embodiments, one or more control units 116 may receive one or more signals 118 that act as commands for the one or more control units 116. In some embodiments, one or more control units 116 may receive one or more information packets that act as commands for the one or more control units 116.

At embodiment 1106, module 840 may include one or more control units that are responsive to one or more timers. In some embodiments, one or more control units 116 may include one or more control units 116 that are responsive to one or more timers. In some embodiments, one or more control units 116 may be configured to include one or more timers to which the one or more control units 116 are responsive. In some embodiments, one or more control units 116 may be responsive to one or more timers that are remote from the one or more control units 116. For example, in some embodiments, one or more control units 116 may be responsive to one or more timers that are associated with one or more management units 122 that send instructions to the one or more control units 116.

At embodiment 1108, module 840 may include one or more control units that are associated with one or more transmitters. In some embodiments, one or more control units 116 may be associated with one or more transmitters. In some embodiments, one or more control units 116 may transmit one or more signals 118. In some embodiments, one or more control units 116 may transmit one or more information packets. Accordingly, in some embodiments, control units 116 may be configured to operate within a feedback scheme that can receive information and transmit information to regulate the generation of nitric oxide. For example, in some embodiments, one or more control units 116 may regulate one or more light sources 106 to generate nitric oxide and then transmit information related to the operation of the one or more light sources 106. In some embodiments, one or more control units 116 may regulate one or more nitric oxide permeable housings 114 to release nitric oxide and then transmit information related to the operation of the one or more housings.

At embodiment 1110, module 840 may include one or more control units that include memory. In some embodiments, one or more control units 116 may include memory. Numerous types of memory may be associated with one or more control units 116. Examples of such memory include, but are not limited to, magnetic memory, semiconductor memory, and the like.

At embodiment 1112, module 840 may include one or more control units that include memory having one or more associated programs. In some embodiments, one or more control units 116 may include memory having one or more associated programs. In some embodiments, one or more control units 116 may include memory that includes a program that provides instructions for operating one or more light sources 106. For example, in some embodiments, one or more control units 116 may receive information with regard to a current concentration of nitric oxide within an area and then process the information with one or more programs to determine one or more operating parameters for one or more light sources 106. In some embodiments, one or more control units 116 may receive information with regard to bacterial contamination within an area and then process the information with one or more programs to determine one or more operating parameters for one or more light sources 106. Accordingly, one or more control units 116 may include one or more programs that may be configured to respond to numerous types of information.

At embodiment 1114, module 840 may include one or more control units that regulate one or more associations of one or more light sources with one or more photolyzable nitric oxide donors. In some embodiments, one or more control units 116 may regulate one or more associations of one or more light sources 106 with one or more photolyzable nitric oxide donors 104. For example, in some embodiments, one or more control units 116 may regulate one or more connections that couple one or more light sources 106 with one or more optical fibers that are associated with one or more photolyzable nitric oxide donors 104. Accordingly, in some embodiments, one or more control units 116 may regulate light emission through regulation of the coupling of one or more light sources 106 with one or more optically transmitting materials that are associated with one or more photolyzable nitric oxide donors 104.

Figure 12:
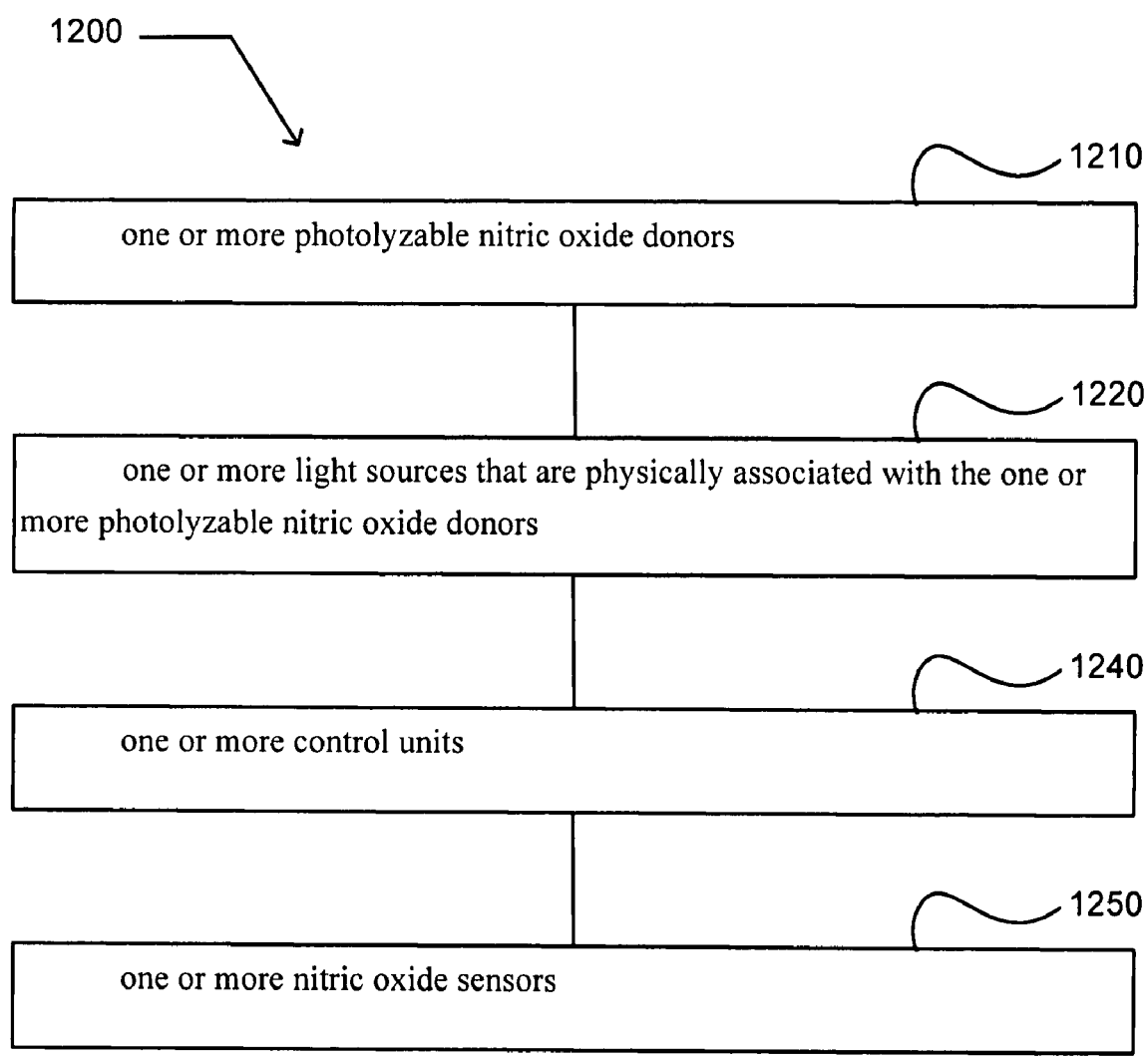
FIG. 12 illustrates embodiment 1200 of device 102 within system 100.

FIG. 12 illustrates alternative embodiments of device 102 within system 100 of FIG. 1. In FIG. 12, discussion and explanation may be provided with respect to the above-described example of FIG. 1, and/or with respect to other examples and contexts. In some embodiments, modules 810, 820, and 840 as described with respect to embodiment 800 of device 102 of FIG. 8 may correspond to modules 1210, 1220, and 1240 as described with respect to embodiment 1200 of device 102 of FIG. 12. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 1200 includes module 1210 that includes one or more photolyzable nitric oxide donors. In some embodiments, a device 102 includes one or more photolyzable nitric oxide donors 104 that release nitric oxide upon photolysis. Examples of such photolyzable nitric oxide donors 104 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 1200 includes module 1220 that includes one or more light sources that are physically associated with the one or more photolyzable nitric oxide donors. In some embodiments, device 102 includes one or more light sources 106 that are physically associated with one or more photolyzable nitric oxide donors 104. In some embodiments, the one or more light sources 106 may be directly coupled to one or more photolyzable nitric oxide donors 104. For example, in some embodiments, the one or more photolyzable nitric oxide donors 104 may be chemically coupled to a surface of the light source 106 (e.g., chemically coupled to a polymer coating on the light source). In some embodiments, one or more photolyzable nitric oxide donors 104 may be indirectly coupled to one or more light sources 106. For example, in some embodiments, one or more photolyzable nitric oxide donors 104 may be coupled to a material that is used to coat the one or more light sources 106.

The embodiment 1200 includes module 1240 that includes one or more control units. In some embodiments, device 102 includes one or more control units 116. A device 102 may include numerous types of control units 116. In some embodiments, one or more control units 116 may be operably coupled with one or more light sources 106, one or more nitric oxide sensors 120, one or more electromagnetic receivers 108, one or more electromagnetic transmitters 112, or substantially any combination thereof. In some embodiments, one or more control units 116 may be operably coupled to other components through use of one or more wireless connections, one or more hardwired connections, or substantially any combination thereof. Control units 116 may be configured in numerous ways. For example, in some embodiments, a control unit 116 may be configured as an on/off switch. Accordingly, in some embodiments, a control unit 116 may be configured to turn a light source 106 on and/or off. In some embodiments, a control unit 116 may be configured to control the emission of light from one or more light sources 106. For example, in some embodiments, one or more control units 116 may regulate the intensity of light emitted from one or more light sources 106, the duration of light emitted from one or more light sources 106, the frequency of light emitted from one or more light sources 106, wavelengths of light emitted from one or more light sources 106, or substantially any combination thereof. In some embodiments, one or more control units 116 may be configured to receive one or more signals 118 from one or more nitric oxide sensors 120. Accordingly, in some embodiments, one or more control units 116 may be configured to control one or more light sources 106 in response to one or more signals 118 received from one or more nitric oxide sensors 120. For example, in some embodiments, one or more nitric oxide sensors 120 may sense a low concentration of nitric oxide in one or more tissues and send one or more signals 118 to one or more control units 116. The one or more control units 116 may then turn one or more light sources 106 on to facilitate release of nitric oxide from one or more photolyzable nitric oxide donors 104. Accordingly, in some embodiments, one or more nitric oxide sensors 120 may sense a high concentration of nitric oxide in one or more tissues and send one or more signals 118 to one or more control units 116. The one or more control units 116 may then turn one or more light sources 106 off to end release of nitric oxide from one or more photolyzable nitric oxide donors 104. In some embodiments, one or more control units 116 may be programmed to control one or more light sources 106. For example, in some embodiments, one or more control units 116 may be programmed to turn one or more light sources 106 on for a predetermined amount of time and then turn off. Accordingly, in some embodiments, one or more control units 116 may be preprogrammed. In some embodiments, one or more control units 116 may be dynamically programmed. For example, in some embodiments, one or more management units 122 may receive one or more signals 118 from one or more nitric oxide sensors 120 and program one or more control units 116 in response to the one or more signals 118 received from the one or more nitric oxide sensors 120. In some embodiments, one or more control units 116 may include one or more receivers that are able to receive one or more signals 118, one or more information packets, or substantially any combination thereof. Control units 116 may be configured in numerous ways. For example, in some embodiments, one or more control units 116 may be operably coupled to one or more light sources 106 that include numerous light emitting diodes that emit light of different wavelengths. Accordingly, in some embodiments, one or more control units 116 may control the wavelengths of light emitted by the one or more light sources 106 by controlling the operation of light emitting diodes that emit light of the selected wavelength. Accordingly, control units 116 may be configured in numerous ways and utilize numerous types of mechanisms.

The embodiment 1200 includes module 1250 that includes one or more nitric oxide sensors. In some embodiments, device 102 includes one or more nitric oxide sensors 120. In some embodiments, one or more nitric oxide sensors 120 may be used to determine the presence of nitric oxide in one or more tissues. In some embodiments, a nitric oxide sensor 120 may be configured for use on the outside surface of an individual 126. For example, in some embodiments, one or more nitric oxide sensors 120 may be configured to detect the concentration of nitric oxide on the surface of skin, a wound, a surface of a table, and the like. In some embodiments, one or more nitric oxide sensors 120 may be configured to be included within one or more housings. In some embodiments, one or more nitric oxide sensors 120 may be configured to be included within one or more nitric oxide permeable housings 114. In some embodiments, a nitric oxide sensor 120 may be configured to utilize fluorescence to detect nitric oxide. For example, in some embodiments, a nitric oxide sensor may detect nitric oxide through use of one or more fluorescent probes, such as 4,5-diaminofluorescein diacetate (EMD Chemicals Inc., San Diego, Calif.). In some embodiments, a nitric oxide sensor may detect nitric oxide through use of one or more electrodes. For example, in some embodiments, a nitric oxide sensor may utilize an electrode that includes a single walled carbon nanotube and an ionic liquid to detect nitric oxide (e.g., Li et al., Electroanalysis, 18:713-718 (2006)). Numerous nitric oxide sensors 120 are commercially available and have been described (e.g., World Precision Instruments, Inc., Sarasota, Fla., USA; U.S. Pat. Nos. 6,100,096; 6,280,604; 5,980,705). In some embodiments, a nitric oxide sensor 120 may include one or more transmitters. In some embodiments, a nitric oxide sensor 120 may include one or more receivers. In some embodiments, a nitric oxide sensor 120 may be configured to transmit one or more signals 118. In some embodiments, a nitric oxide sensor 120 may be configured to receive one or more signals 118.

FIG. 13 illustrates alternative embodiments of embodiment 1200 of device 102 within system 100 of FIG. 12. FIG. 13 illustrates example embodiments of module 1250. Additional embodiments may include an embodiment 1302, an embodiment 1304, an embodiment 1306, an embodiment 1308, and/or an embodiment 1310.

At embodiment 1302, module 1250 may include one or more nitric oxide sensors that are configured to detect nitric oxide. In some embodiments, one or more nitric oxide sensors 120 may include one or more nitric oxide sensors 120 that are configured to detect nitric oxide. Nitric oxide sensors 120 may be configured in numerous ways. In some embodiments, a nitric oxide sensor 120 may be configured to utilize fluorescence to detect nitric oxide. For example, in some embodiments, a nitric oxide sensor may detect nitric oxide through use of one or more fluorescent probes, such as 4,5-diaminofluorescein diacetate (EMD Chemicals Inc., San Diego, Calif.). In some embodiments, a nitric oxide sensor may detect nitric oxide through use of one or more electrodes. For example, in some embodiments, a nitric oxide sensor may utilize an electrode that includes a single walled carbon nanotube and an ionic liquid to detect nitric oxide (e.g., Li et al., Electroanalysis, 18:713-718 (2006)). Numerous nitric oxide sensors 120 are commercially available and have been described (e.g., World Precision Instruments, Inc., Sarasota, Fla., USA; U.S. Pat. Nos. 6,100,096; 6,280,604; 5,980,705).

At embodiment 1304, module 1250 may include one or more nitric oxide sensors that are configured to detect one or more nitric oxide synthases. In some embodiments, one or more nitric oxide sensors 120 may include one or more nitric oxide sensors 120 that are configured to detect one or more nitric oxide synthases. In some embodiments, one or more nitric oxide sensors 120 may be configured to detect nitric oxide synthase activity. Nitric oxide synthase detection kits are commercially available (e.g., Cell Technology, Inc., Mountain View, Calif.). In some embodiments, one or more nitric oxide sensors 120 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more nitric oxide sensors 120 may be configured to detect nitric oxide synthase through immunological methods. Methods that may be used to detect nitric oxide synthase directly been reported (e.g., Burrell et al., J. Histochem. Cytochem., 44:339-346 (1996) and Hattenbach et al., Opthalmologica, 216:209-214 (2002)). In some embodiments, microelectromechanical systems may be used to detect nitric oxide synthase. In some embodiments, antibodies and/or aptamers that bind to nitric oxide synthase may be used within one or more microelectromechanical systems to detect nitric oxide synthase. Methods to construct microelectromechanical detectors have been described (e.g., Gau et al., Biosensors & Bioelectronics, 16:745-755 (2001)). Accordingly, nitric oxide sensors may be configured in numerous ways to detect one or more nitric oxide synthases.

At embodiment 1306, module 1250 may include one or more nitric oxide sensors that are configured to detect one or more nitric oxide donors. In some embodiments, one or more nitric oxide sensors 120 may include one or more nitric oxide sensors 120 that are configured to detect one or more nitric oxide donors. In some embodiments, one or more nitric oxide sensors 120 may include one or more surface plasmon resonance chemical electrodes that are configured to detect one or more nitric oxide donors. For example, in some embodiments, one or more nitric oxide sensors 120 may include one or more surface plasmon resonance chemical electrodes that include antibodies and/or aptamers that bind to one or more nitric oxide donors. Accordingly, such electrodes may be used to detect the one or more nitric oxide donors through use of surface plasmon resonance. Methods to construct surface plasmon resonance chemical electrodes are known and have been described (e.g., U.S. Pat. No. 5,858,799; Lin et al., Applied Optics, 46:800-806 (2007)). In some embodiments, antibodies and/or aptamers that bind to one or more nitric oxide donors may be used within one or more microelectromechanical systems to detect one or more nitric oxide donors. Methods to construct microelectromechanical detectors have been described (e.g., Gau et al., Biosensors & Bioelectronics, 16:745-755 (2001)).

At embodiment 1308, module 1250 may include one or more nitric oxide sensors that are operably associated with the one or more control units. In some embodiments, one or more nitric oxide sensors 120 may be operably associated with one or more control units 116. In some embodiments, one or more nitric oxide sensors 120 may be operably associated with one or more control units 116 through a hardwired connection. In some embodiments, one or more nitric oxide sensors 120 may be operably associated with one or more control units 116 through a wireless connection. In some embodiments, one or more nitric oxide sensors 120 may be configured to send one or more signals 118 to one or more control units 116. In some embodiments, one or more nitric oxide sensors 120 may be configured to receive one or more signals 118 from one or more control units 116.

At embodiment 1310, module 1250 may include one or more nitric oxide sensors that are configured to transmit one or more information packets. In some embodiments, one or more nitric oxide sensors 120 may be configured to transmit one or more information packets. In some embodiments, one or more nitric oxide sensors 120 may be configured to transmit one or more information packets to one or more control units 116. Information packets may include numerous types of information. Examples of such information include, but are not limited to, nitric oxide concentration, temperature, time, and the like.

Figure 13A:
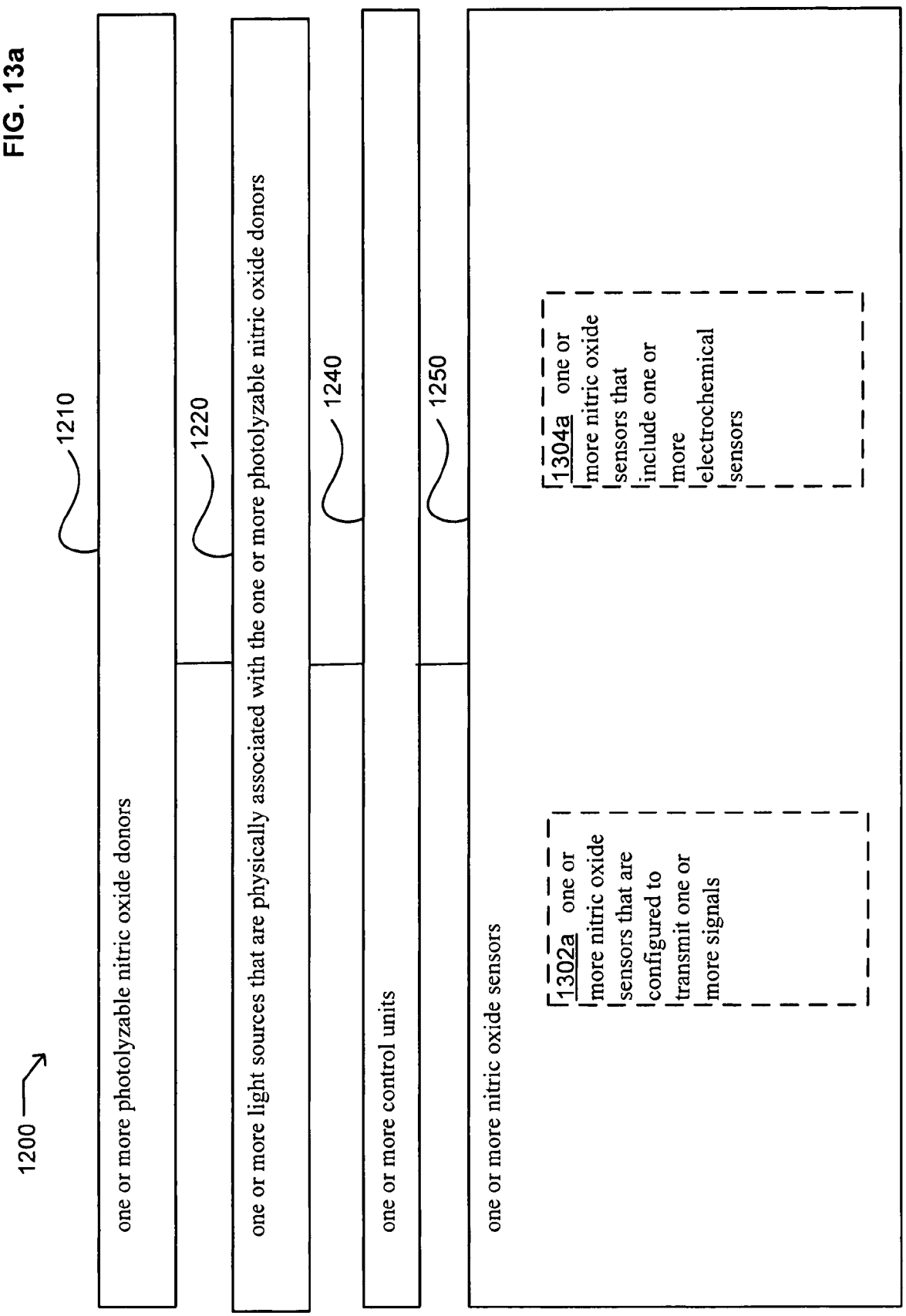
FIG. 13a illustrates alternate embodiments of embodiment 1200 of device 102 within system 100.

FIG. 13*a* illustrates alternative embodiments of embodiment 1200 of device 102 within system 100 of FIG. 12. FIG. 13*a* illustrates example embodiments of module 1250. Additional embodiments may include an embodiment 1302*a*, and/or an embodiment 1304*a*.

At embodiment 1302*a*, module 1250 may include one or more nitric oxide sensors that are configured to transmit one or more signals. In some embodiments, one or more nitric oxide sensors 120 may be configured to transmit one or more signals 118. In some embodiments, one or more nitric oxide sensors 120 may be configured to transmit one or more signals 118. Numerous types of signals 118 may be transmitted. Examples of such signals 118 include, but are not limited to, optical signals 118, radio signals 118, wireless signals 118, hardwired signals 118, infrared signals 118, ultrasonic signals 118, and the like.

At embodiment 1304*a*, module 1250 may include one or more nitric oxide sensors that include one or more electrochemical sensors. In some embodiments, a device 102 may include one or more nitric oxide sensors 120 that include one or more electrochemical sensors. Nitric oxide sensors 120 may include numerous types of electrochemical sensors. For example, in some embodiments, an electrochemical sensor may be configured as a nitric oxide specific electrode. In some embodiments, a nitric oxide specific electrode may include ruthenium and/or at least one oxide of ruthenium. Methods to construct such electrodes are known and have been described (e.g., U.S. Pat. Nos. 6,280,604; 5,980,705). In some embodiments, a nitric oxide sensor 120 may include an amperometric sensor that includes a sensing electrode that is configured to oxidize nitric oxide complexes to generate an electrical current that indicates the concentration of nitric oxide. Methods to construct such electrodes are known and have been described (e.g., U.S. Patent Application No.: 20070181444 and Ikeda et al., Sensors, 5:161-170 (2005)). Numerous types of electrochemical sensors may be associated with one or more nitric oxide sensors 120 (e.g., Li et al., Electroanalysis, 18:713-718 (2006)). Electrodes that may be used to detect nitric oxide are commercially available (World Precision Instruments, Sarasota, Fl). In some embodiments, such electrodes may be used to detect nitric oxide at concentrations of about 0.5 nanomolar and above, and may be about 100 micrometers in diameter (World Precision Instruments, Sarasota, Fl).

FIG. 14 illustrates alternative embodiments of embodiment 1200 of device 102 within system 100 of FIG. 12. FIG. 14 illustrates example embodiments of module 1250. Additional embodiments may include an embodiment 1402, an embodiment 1404, an embodiment 1406, and/or an embodiment 1408.

At embodiment 1402, module 1250 may include one or more nitric oxide sensors that include one or more semiconductor sensors. In some embodiments, one or more nitric oxide sensors 120 may include one or more nitric oxide sensors 120 that include one or more semiconductor sensors. In some embodiments, the sensor may be a molecular controlled semiconductor resistor of a multilayered GaAs structure to which a layer of multifunctional NO-binding molecules are adsorbed. Such nitric oxide binding molecules may include, but are not limited to, vicinal diamines, metalloporphyrins, metallophthalocyanines, and iron-dithiocarbamate complexes that contain at least one functional group selected from carboxyl, thiol, acyclic sulfide, cyclic disulfide, hydroxamic acid, trichlorosilane or phosphate (e.g., U.S. Published Patent Application No.: 20040072360). In some embodiments, a semiconductive nitric oxide sensor 120 may employ a polycrystalline-oxide semiconductor material that is coated with porous metal electrodes to form a semiconductor sandwich. In some embodiments, the semiconductor material may be formed of $SnO_2$ or $ZnO$. The porous electrodes may be formed with platinum and used to measure the conductivity of the semiconductor material. The conductivity of the semiconductor material changes when nitric oxide is absorbed on the surface of the semiconductor material (e.g., U.S. Pat. No. 5,580,433; International Application Publication Number WO 02/057738). Numerous other semiconductor sensors may be used to detect nitric oxide.

At embodiment 1404, module 1250 may include one or more nitric oxide sensors that include one or more chemical sensors. In some embodiments, a device 102 may include one or more nitric oxide sensors 120 that include one or more chemical sensors. For example, in some embodiments, one or more nitric oxide sensors 120 may include one or more chemical sensors that include a reagent solution that undergoes a chemiluminescent reaction with nitric oxide. Accordingly, one or more photodetectors may be used to detect nitric oxide. Methods to construct such detectors are known and have been described (e.g., U.S. Pat. No. 6,100,096). In some embodiments, ozone may be reacted with nitric oxide to produce light in proportion to the amount of nitric oxide present. The light produced may be measured with a photodetector. In some embodiments, sensors may include one or more charge-coupled devices to detect photonic emission.

At embodiment 1406, module 1250 may include one or more nitric oxide sensors that include one or more fluorescent sensors. In some embodiments, one or more nitric oxide sensors 120 may include one or more nitric oxide sensors 120 that include one or more fluorescent sensors. In some embodiments, a fluorescent sensor may include one or more fluorescent probes that may be used to detect nitric oxide. For example, in some embodiments, 4,5-diaminofluorescein may be used to determine nitric oxide concentration (e.g., Rathel et al., Biol. Proced. Online, 5:136-142 (2003)). Probes that may be used to detect nitric oxide are commercially available (EMD Chemicals Inc., San Diego, Calif.).

At embodiment 1408, module 1250 may include one or more nitric oxide sensors that include one or more Raman sensors. In some embodiments, one or more nitric oxide sensors 120 may include one or more nitric oxide sensors 120 that include one or more Raman sensors. Methods to use Raman spectroscopy to detect nitric oxide are known and have been described (e.g., U.S. Patent Application No.: 20060074282). In addition, Raman spectrometers are commercially available (e.g., Raman Systems, Austin, Tex. and B&W Tek, Inc., Newark, Del.).

Figure 15:
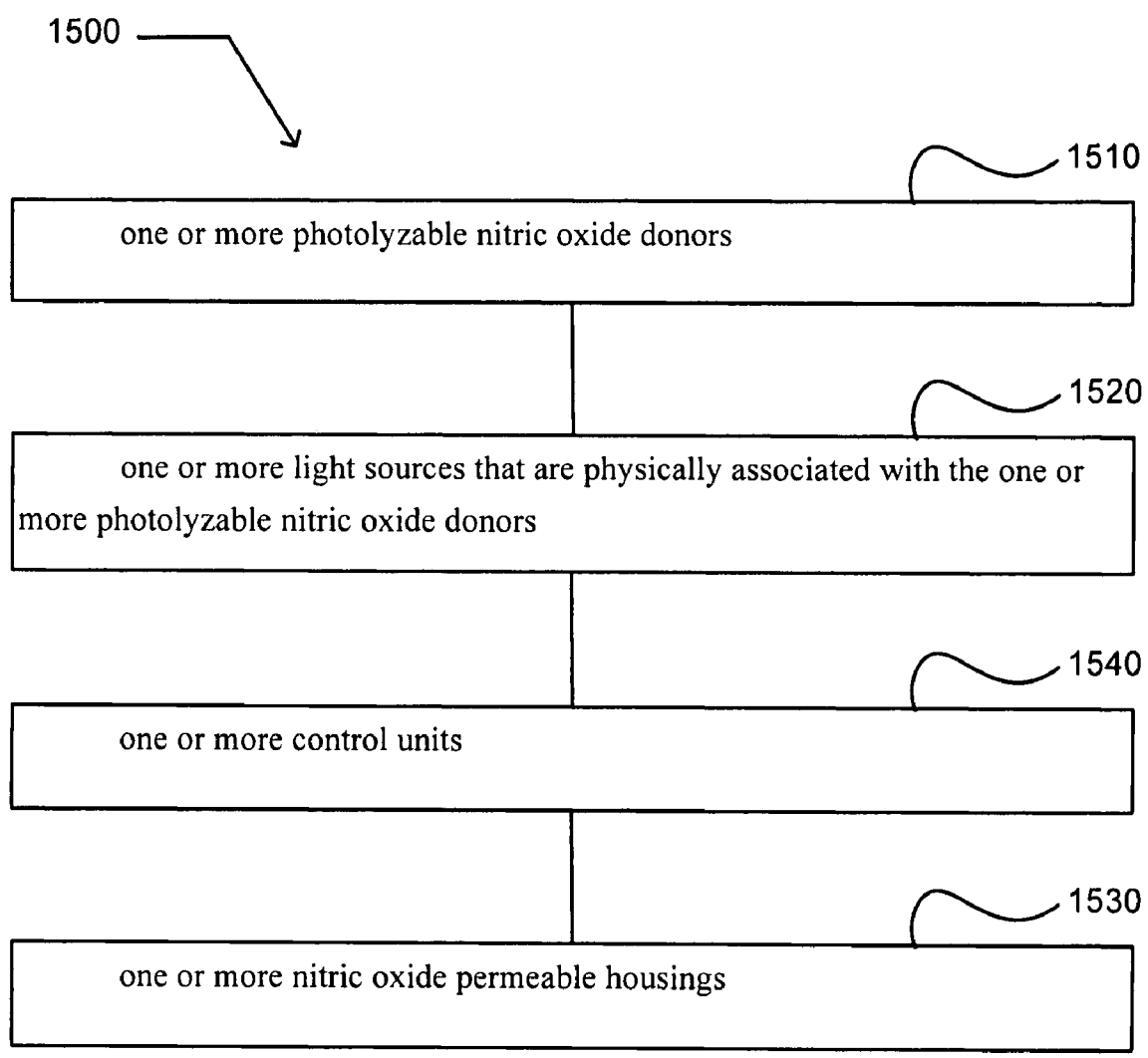
FIG. 15 illustrates embodiment 1500 of device 102 within system 100.

FIG. 15 illustrates alternative embodiment 1500 of device 102 within system 100 of FIG. 1. In FIG. 15, discussion and explanation may be provided with respect to the above-described example of FIG. 1, and/or with respect to other examples and contexts. In some embodiments, modules 810, 820, and 840 as described with respect to embodiment 800 of device 102 of FIG. 8 may correspond to modules 1510, 1520, and 1540 as described with respect to embodiment 1500 of device 102 of FIG. 15. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 1500 includes module 1510 that includes one or more photolyzable nitric oxide donors. In some embodiments, a device 102 includes one or more photolyzable nitric oxide donors 104 that release nitric oxide upon photolysis. Examples of such photolyzable nitric oxide donors 104 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 1500 includes module 1520 that includes one or more light sources that are physically associated with the one or more photolyzable nitric oxide donors. In some embodiments, device 102 includes one or more light sources 106 that are physically associated with one or more photolyzable nitric oxide donors 104. In some embodiments, the one or more light sources 106 may be directly coupled to one or more photolyzable nitric oxide donors 104. For example, in some embodiments, the one or more photolyzable nitric oxide donors 104 may be chemically coupled to a surface of the light source 106 (e.g., chemically coupled to a polymer coating on the light source). In some embodiments, one or more photolyzable nitric oxide donors 104 may be indirectly coupled to one or more light sources 106. For example, in some embodiments, one or more photolyzable nitric oxide donors 104 may be coupled to a material that is used to coat the one or more light sources 106.

The embodiment 1500 includes module 1540 that includes one or more control units. In some embodiments, device 102 includes one or more control units 116. A device 102 may include numerous types of control units 116. In some embodiments, one or more control units 116 may be operably coupled with one or more light sources 106, one or more nitric oxide sensors 120, one or more electromagnetic receivers 108, one or more electromagnetic transmitters 112, or substantially any combination thereof. In some embodiments, one or more control units 116 may be operably coupled to other components through use of one or more wireless connections, one or more hardwired connections, or substantially any combination thereof. Control units 116 may be configured in numerous ways. For example, in some embodiments, a control unit 116 may be configured as an on/off switch. Accordingly, in some embodiments, a control unit 116 may be configured to turn a light source 106 on and/or off. In some embodiments, a control unit 116 may be configured to control the emission of light from one or more light sources 106. For example, in some embodiments, one or more control units 116 may regulate the intensity of light emitted from one or more light sources 106, the duration of light emitted from one or more light sources 106, the frequency of light emitted from one or more light sources 106, wavelengths of light emitted from one or more light sources 106, or substantially any combination thereof. In some embodiments, one or more control units 116 may be configured to receive one or more signals 118 from one or more nitric oxide sensors 120. Accordingly, in some embodiments, one or more control units 116 may be configured to control one or more light sources 106 in response to one or more signals 118 received from one or more nitric oxide sensors 120. For example, in some embodiments, one or more nitric oxide sensors 120 may sense a low concentration of nitric oxide in one or more tissues and send one or more signals 118 to one or more control units 116. The one or more control units 116 may then turn one or more light sources 106 on to facilitate release of nitric oxide from one or more photolyzable nitric oxide donors 104. Accordingly, in some embodiments, one or more nitric oxide sensors 120 may sense a high concentration of nitric oxide in one or more tissues and send one or more signals 118 to one or more control units 116. The one or more control units 116 may then turn one or more light sources 106 off to end release of nitric oxide from one or more photolyzable nitric oxide donors 104. In some embodiments, one or more control units 116 may be programmed to control one or more light sources 106. For example, in some embodiments, one or more control units 116 may be programmed to turn one or more light sources 106 on for a predetermined amount of time and then turn off. Accordingly, in some embodiments, one or more control units 116 may be preprogrammed. In some embodiments, one or more control units 116 may be dynamically programmed. For example, in some embodiments, one or more management units 122 may receive one or more signals 118 from one or more nitric oxide sensors 120 and program one or more control units 116 in response to the one or more signals 118 received from the one or more nitric oxide sensors 120. In some embodiments, one or more control units 116 may include one or more receivers that are able to receive one or more signals 118, one or more information packets, or substantially any combination thereof. Control units 116 may be configured in numerous ways. For example, in some embodiments, one or more control units 116 may be operably coupled to one or more light sources 106 that include numerous light emitting diodes that emit light of different wavelengths. Accordingly, in some embodiments, one or more control units 116 may control the wavelengths of light emitted by the one or more light sources 106 by controlling the operation of light emitting diodes that emit light of the selected wavelength. Accordingly, control units 116 may be configured in numerous ways and utilize numerous types of mechanisms.

The embodiment 1500 includes module 1530 that includes one or more nitric oxide permeable housings. In some embodiments, device 102 may include one or more nitric oxide permeable housings 114. In some embodiments, nitric oxide permeable housings 114 may be configured for implantation within an individual 126. In some embodiments, nitric oxide permeable housings 114 may be configured to facilitate application of nitric oxide to a surface. In some embodiments, one or more nitric oxide permeable housings 114 may be configured to facilitate application of nitric oxide to one or more surfaces of an individual 126. For example, in some embodiments, one or more nitric oxide permeable housings 114 may be configured as a canister having a nitric oxide permeable end that may be positioned on a skin surface of an individual 126 to deliver nitric oxide to the skin surface. In some embodiments, one or more nitric oxide permeable housings 114 may be configured for insertion into the urethra of a male. In some embodiments, one or more nitric oxide permeable housings 114 may be configured for insertion into the vagina of a female.

In some embodiments, one or more nitric oxide permeable housings 114 may be configured to enclose at least a portion of one or more photolyzable nitric oxide donors 104. In some embodiments, one or more nitric oxide permeable housings 114 may be configured to enclose at least a portion of one or more light sources 106. In some embodiments, one or more nitric oxide permeable housings 114 may be configured to enclose at least a portion of one or more control units 116. In some embodiments, one or more nitric oxide permeable housings 114 may be configured to enclose at least a portion of one or more nitric oxide sensors 120. In some embodiments, one or more nitric oxide permeable housings 114 may be configured to enclose one or more photolyzable nitric oxide donors 104. In some embodiments, one or more nitric oxide permeable housings 114 may be configured to enclose one or more light sources 106. In some embodiments, one or more nitric oxide permeable housings 114 may be configured to enclose one or more photolyzable nitric oxide donors 104 and one or more light sources 106. In some embodiments, one or more nitric oxide permeable housings 114 may be configured to enclose one or more photolyzable nitric oxide donors 104, one or more light sources 106, and one or more control units 116. In some embodiments, one or more nitric oxide permeable housings 114 may be configured to enclose one or more photolyzable nitric oxide donors 104, one or more light sources 106, one or more control units 116, and one or more electromagnetic receivers 108. In some embodiments, one or more nitric oxide permeable housings 114 may be configured to enclose one or more photolyzable nitric oxide donors 104, one or more light sources 106, one or more control units 116, one or more electromagnetic receivers 108, or substantially any combination thereof. In some embodiments, one or more nitric oxide permeable housings 114 may be configured to include one or more compartments. For example, in some embodiments, a nitric oxide permeable housing 114 may include a compartment that is configured to accept one or more light sources 106 and a second compartment that is configured to accept one or more photolyzable nitric oxide donors 104. In some embodiments, a nitric oxide permeable housing 114 may include a compartment that is configured to accept one or more light sources 106, a light permeable divider, and a second compartment that is configured to accept one or more photolyzable nitric oxide donors 104. In some embodiments, a light permeable divider may be made of a material that allows light to pass through the divider. Examples of such material include, but are not limited to, plastic, quartz, and the like.

Nitric oxide permeable housings 114 may be constructed of numerous types of materials and combinations of materials. Examples of such materials include, but are not limited to, ceramics, polymeric materials, metals, plastics, and the like. In some embodiments, nitric oxide permeable housings 114 may include numerous combinations of materials.

Figure 16:
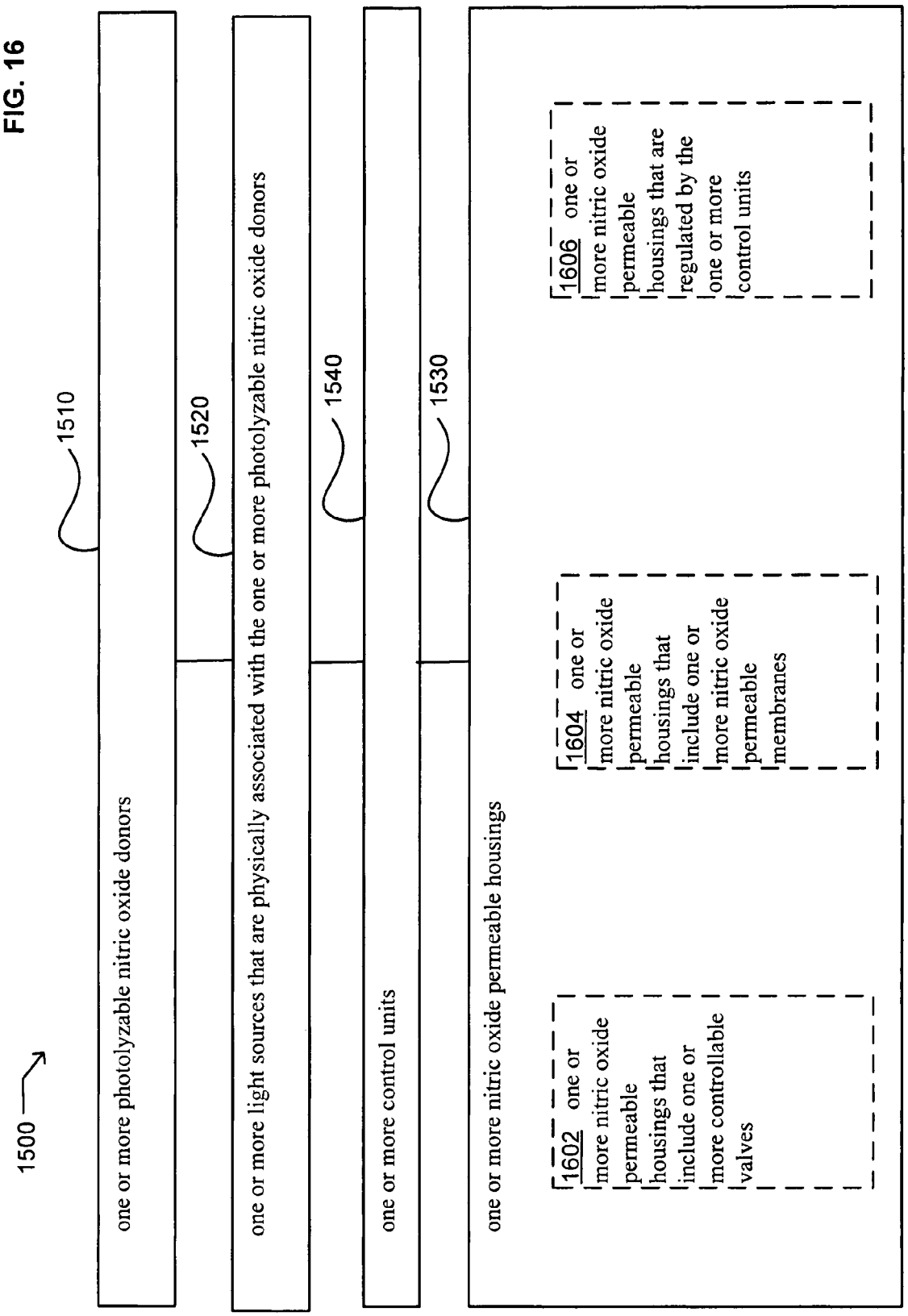
FIG. 16 illustrates alternate embodiments of embodiment 1500 of device 102 within system 100.

FIG. 16 illustrates alternative embodiments of embodiment 1500 of device 102 within system 100 of FIG. 15. FIG. 16 illustrates example embodiments of module 1530. Additional embodiments may include an embodiment 1602, an embodiment 1604, and/or an embodiment 1606.

At embodiment 1602, module 1530 may include one or more nitric oxide permeable housings that include one or more controllable valves. In some embodiments, one or more nitric oxide permeable housings 114 may include one or more controllable valves. In some embodiments, a controllable valve may provide for the passage of nitric oxide. In some embodiments, a controllable valve may provide for the passage of one or more photolyzable nitric oxide donors 104. In some embodiments, one or more controllable valves may include one or more electromagnets that provide for controlled opening and closing of an orifice associated with the valve. In some embodiments, one or more controllable valves may include one or more screw closures that provide for controlled opening and closing of the valve. For example, in some embodiments, a nitric oxide permeable housing 114 may include an electric motor that operates the screw mechanism to provide for opening and closure of an orifice associated with the nitric oxide permeable housing 114. Numerous controllable valves may be associated with one or more nitric oxide permeable housings 114. In some embodiments, a nitric oxide permeable housing 114 may include one or more valves that are controllable by one or more control units 116. Accordingly, in some embodiments, valves may be opened or closed in response to one or more nitric oxide sensors 120, one or more signals 118, one or more information packets, one or more management units 122, or substantially any combination thereof.

At embodiment 1604, module 1530 may include one or more nitric oxide permeable housings that include one or more nitric oxide permeable membranes. In some embodiments, one or more nitric oxide permeable housings 114 may include one or more nitric oxide permeable membranes. For example, in some embodiments, a nitric oxide permeable housing 114 may include a nitric oxide impermeable metal canister that is coupled to a nitric oxide permeable membrane (e.g., U.S. Patent Application No. 20020026937). In some embodiments, a nitric oxide permeable housing 114 may include a selectively permeable membrane. For example, in some embodiments, a nitric oxide permeable housing 114 may include a selectively permeable, hydrophilic polyester co-polymer membrane system that includes a copolymer with 70% polyester and 30% polyether (e.g., Sympatex™ 10 µm membrane, see Hardwick et al., Clinical Science, 100:395-400 (2001)). In some embodiments, a nitric oxide permeable housing 114 may include a scintered glass portion that is permeable to nitric oxide. Accordingly, nitric oxide permeable housings 114 may include numerous types of porous ceramics that are permeable to nitric oxide. In some embodiments, a nitric oxide permeable housing 114 may include a nitric oxide permeable coating (e.g., U.S. Patent Application Nos. 20050220838 and 20030093143).

At embodiment 1606, module 1530 may include one or more nitric oxide permeable housings that are regulated by the one or more control units. In some embodiments, one or more nitric oxide permeable housings 114 may include one or more nitric oxide permeable housings 114 that are regulated by the one or more control units 116. For example, in some embodiments, one or more nitric oxide permeable housings 114 may include one or more controllable valves that are regulated (e.g., opened and/or closed) in response to one or more control units 116.

Figure 17:
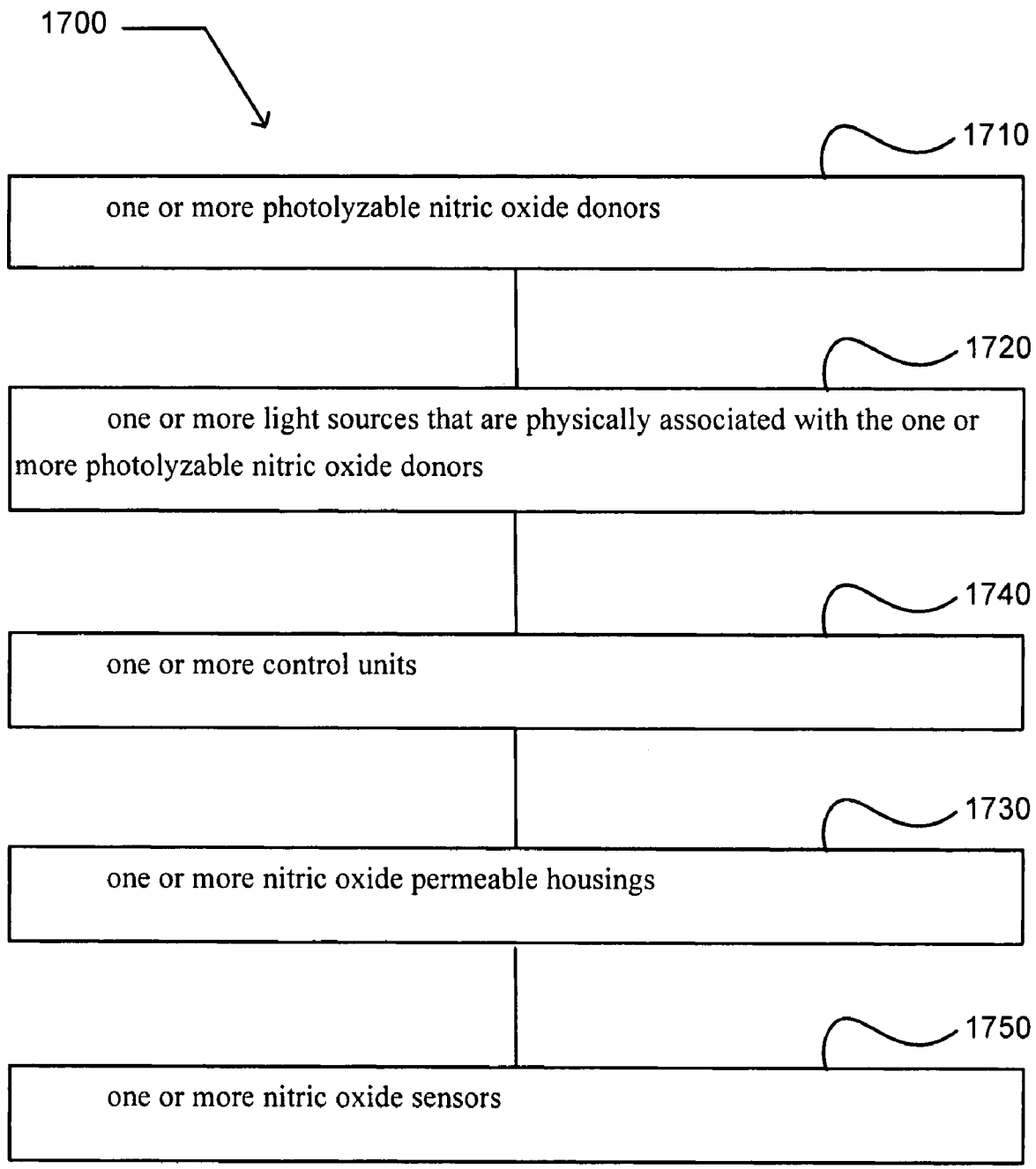
FIG. 17 illustrates embodiment 1700 of device 102 within system 100.

FIG. 17 illustrates alternative embodiment 1700 of device 102 within system 100 of FIG. 1. In FIG. 17, discussion and explanation may be provided with respect to the above-described example of FIG. 1, and/or with respect to other examples and contexts. In some embodiments, modules 1510, 1520, 1530, and 1540 as described with respect to embodiment 1500 of device 102 of FIG. 15 may correspond to modules 1710, 1720, 1730, and 1740 as described with respect to embodiment 1700 of device 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 1700 includes module 1710 that includes one or more photolyzable nitric oxide donors. In some embodiments, a device 102 includes one or more photolyzable nitric oxide donors 104 that release nitric oxide upon photolysis. Examples of such photolyzable nitric oxide donors 104 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 1700 includes module 1720 that includes one or more light sources that are physically associated with the one or more photolyzable nitric oxide donors. In some embodiments, device 102 includes one or more light sources 106 that are physically associated with one or more photolyzable nitric oxide donors 104. In some embodiments, the one or more light sources 106 may be directly coupled to one or more photolyzable nitric oxide donors 104. For example, in some embodiments, the one or more photolyzable nitric oxide donors 104 may be chemically coupled to a surface of the light source 106 (e.g., chemically coupled to a polymer coating on the light source). In some embodiments, one or more photolyzable nitric oxide donors 104 may be indirectly coupled to one or more light sources 106. For example, in some embodiments, one or more photolyzable nitric oxide donors 104 may be coupled to a material that is used to coat the one or more light sources 106.

The embodiment 1700 includes module 1740 that includes one or more control units. In some embodiments, device 102 includes one or more control units 116. A device 102 may include numerous types of control units 116. In some embodiments, one or more control units 116 may be operably coupled with one or more light sources 106, one or more nitric oxide sensors 120, one or more electromagnetic receivers 108, one or more electromagnetic transmitters 112, or substantially any combination thereof. In some embodiments, one or more control units 116 may be operably coupled to other components through use of one or more wireless connections, one or more hardwired connections, or substantially any combination thereof. Control units 116 may be configured in numerous ways. For example, in some embodiments, a control unit 116 may be configured as an on/off switch. Accordingly, in some embodiments, a control unit 116 may be configured to turn a light source 106 on and/or off. In some embodiments, a control unit 116 may be configured to control the emission of light from one or more light sources 106. For example, in some embodiments, one or more control units 116 may regulate the intensity of light emitted from one or more light sources 106, the duration of light emitted from one or more light sources 106, the frequency of light emitted from one or more light sources 106, wavelengths of light emitted from one or more light sources 106, or substantially any combination thereof. In some embodiments, one or more control units 116 may be configured to receive one or more signals 118 from one or more nitric oxide sensors 120. Accordingly, in some embodiments, one or more control units 116 may be configured to control one or more light sources 106 in response to one or more signals 118 received from one or more nitric oxide sensors 120. For example, in some embodiments, one or more nitric oxide sensors 120 may sense a low concentration of nitric oxide in one or more tissues and send one or more signals 118 to one or more control units 116. The one or more control units 116 may then turn one or more light sources 106 on to facilitate release of nitric oxide from one or more photolyzable nitric oxide donors 104. Accordingly, in some embodiments, one or more nitric oxide sensors 120 may sense a high concentration of nitric oxide in one or more tissues and send one or more signals 118 to one or more control units 116. The one or more control units 116 may then turn one or more light sources 106 off to end release of nitric oxide from one or more photolyzable nitric oxide donors 104. In some embodiments, one or more control units 116 may be programmed to control one or more light sources 106. For example, in some embodiments, one or more control units 116 may be programmed to turn one or more light sources 106 on for a predetermined amount of time and then turn off. Accordingly, in some embodiments, one or more control units 116 may be preprogrammed. In some embodiments, one or more control units 116 may be dynamically programmed. For example, in some embodiments, one or more management units 122 may receive one or more signals 118 from one or more nitric oxide sensors 120 and program one or more control units 116 in response to the one or more signals 118 received from the one or more nitric oxide sensors 120. In some embodiments, one or more control units 116 may include one or more receivers that are able to receive one or more signals 118, one or more information packets, or substantially any combination thereof. Control units 116 may be configured in numerous ways. For example, in some embodiments, one or more control units 116 may be operably coupled to one or more light sources 106 that include numerous light emitting diodes that emit light of different wavelengths. Accordingly, in some embodiments, one or more control units 116 may control the wavelengths of light emitted by the one or more light sources 106 by controlling the operation of light emitting diodes that emit light of the selected wavelength. Accordingly, control units 116 may be configured in numerous ways and utilize numerous types of mechanisms.

The embodiment 1700 includes module 1730 that includes one or more nitric oxide permeable housings. In some embodiments, device 102 may include one or more nitric oxide permeable housings 114. In some embodiments, nitric oxide permeable housings 114 may be configured for implantation within an individual 126. In some embodiments, nitric oxide permeable housings 114 may be configured to facilitate application of nitric oxide to a surface. In some embodiments, one or more nitric oxide permeable housings 114 may be configured to facilitate application of nitric oxide to one or more surfaces of an individual 126. For example, in some embodiments, one or more nitric oxide permeable housings 114 may be configured as a canister having a nitric oxide permeable end that may be positioned on a skin surface of an individual 126 to deliver nitric oxide to the skin surface. In some embodiments, one or more nitric oxide permeable housings 114 may be configured for insertion into the urethra of a male. In some embodiments, one or more nitric oxide permeable housings 114 may be configured for insertion into the vagina of a female.

In some embodiments, one or more nitric oxide permeable housings 114 may be configured to enclose at least a portion of one or more photolyzable nitric oxide donors 104. In some embodiments, one or more nitric oxide permeable housings 114 may be configured to enclose at least a portion of one or more light sources 106. In some embodiments, one or more nitric oxide permeable housings 114 may be configured to enclose at least a portion of one or more control units 116. In some embodiments, one or more nitric oxide permeable housings 114 may be configured to enclose at least a portion of one or more nitric oxide sensors 120. In some embodiments, one or more nitric oxide permeable housings 114 may be configured to enclose one or more photolyzable nitric oxide donors 104. In some embodiments, one or more nitric oxide permeable housings 114 may be configured to enclose one or more light sources 106. In some embodiments, one or more nitric oxide permeable housings 114 may be configured to enclose one or more photolyzable nitric oxide donors 104 and one or more light sources 106. In some embodiments, one or more nitric oxide permeable housings 114 may be configured to enclose one or more photolyzable nitric oxide donors 104, one or more light sources 106, and one or more control units 116. In some embodiments, one or more nitric oxide permeable housings 114 may be configured to enclose one or more photolyzable nitric oxide donors 104, one or more light sources 106, one or more control units 116, and one or more electromagnetic receivers 108. In some embodiments, one or more nitric oxide permeable housings 114 may be configured to enclose one or more photolyzable nitric oxide donors 104, one or more light sources 106, one or more control units 116, one or more electromagnetic receivers 108, or substantially any combination thereof. In some embodiments, one or more nitric oxide permeable housings 114 may be configured to include one or more compartments. For example, in some embodiments, a nitric oxide permeable housing 114 may include a compartment that is configured to accept one or more light sources 106 and a second compartment that is configured to accept one or more photolyzable nitric oxide donors 104. In some embodiments, a nitric oxide permeable housing 114 may include a compartment that is configured to accept one or more light sources 106, a light permeable divider, and a second compartment that is configured to accept one or more photolyzable nitric oxide donors 104. In some embodiments, a light permeable divider may be made of a material that allows light to pass through the divider. Examples of such material include, but are not limited to, plastic, quartz, and the like.

Nitric oxide permeable housings 114 may be constructed of numerous types of materials and combinations of materials. Examples of such materials include, but are not limited to, ceramics, polymeric materials, metals, plastics, and the like. In some embodiments, nitric oxide permeable housings 114 may include numerous combinations of materials.

The embodiment 1700 includes module 1750 that includes one or more nitric oxide sensors. In some embodiments, device 102 includes one or more nitric oxide sensors 120. In some embodiments, one or more nitric oxide sensors 120 may be used to determine the presence of nitric oxide in one or more tissues. In some embodiments, a nitric oxide sensor 120 may be configured for use on the outside surface of an individual 126. For example, in some embodiments, one or more nitric oxide sensors 120 may be configured to detect the concentration of nitric oxide on the surface of skin, a wound, a surface of a table, and the like. In some embodiments, one or more nitric oxide sensors 120 may be configured to be included within one or more housings. In some embodiments, one or more nitric oxide sensors 120 may be configured to be included within one or more nitric oxide permeable housings 114. In some embodiments, a nitric oxide sensor 120 may be configured to utilize fluorescence to detect nitric oxide. For example, in some embodiments, a nitric oxide sensor may detect nitric oxide through use of one or more fluorescent probes, such as 4,5-diaminofluorescein diacetate (EMD Chemicals Inc., San Diego, Calif.). In some embodiments, a nitric oxide sensor may detect nitric oxide through use of one or more electrodes. For example, in some embodiments, a nitric oxide sensor may utilize an electrode that includes a single walled carbon nanotube and an ionic liquid to detect nitric oxide (e.g., Li et al., Electroanalysis, 18:713-718 (2006)). Numerous nitric oxide sensors 120 are commercially available and have been described (e.g., World Precision Instruments, Inc., Sarasota, Fla., USA; U.S. Pat. Nos. 6,100, 096; 6,280,604; 5,980,705). In some embodiments, a nitric oxide sensor 120 may include one or more transmitters. In some embodiments, a nitric oxide sensor 120 may include one or more receivers. In some embodiments, a nitric oxide sensor 120 may be configured to transmit one or more signals 118. In some embodiments, a nitric oxide sensor 120 may be configured to receive one or more signals 118.

FIG. 18 illustrates alternative embodiments of embodiment 1700 of device 102 of FIG. 17. FIG. 18 illustrates example embodiments of module 1750. Additional embodiments may include an embodiment 1802, an embodiment 1804, an embodiment 1806, an embodiment 1808, an embodiment 1810, an embodiment 1812, and/or an embodiment 1814.

At embodiment 1802, module 1750 may include one or more nitric oxide sensors that are configured to detect nitric oxide. In some embodiments, one or more nitric oxide sensors 120 may include one or more nitric oxide sensors 120 that are configured to detect nitric oxide. Nitric oxide sensors 120 may be configured in numerous ways. In some embodiments, a nitric oxide sensor 120 may be configured to utilize fluorescence to detect nitric oxide. For example, in some embodiments, a nitric oxide sensor may detect nitric oxide through use of one or more fluorescent probes, such as 4,5-diaminofluorescein diacetate (EMD Chemicals Inc., San Diego, Calif.). In some embodiments, a nitric oxide sensor may detect nitric oxide through use of one or more electrodes. For example, in some embodiments, a nitric oxide sensor may utilize an electrode that includes a single walled carbon nanotube and an ionic liquid to detect nitric oxide (e.g., Li et al., Electroanalysis, 18:713-718 (2006)). Numerous nitric oxide sensors 120 are commercially available and have been described (e.g., World Precision Instruments, Inc., Sarasota, Fla., USA; U.S. Pat. Nos. 6,100,096; 6,280,604; 5,980,705).

At embodiment 1804, module 1750 may include one or more nitric oxide sensors that are configured to detect nitric oxide synthase. In some embodiments, one or more nitric oxide sensors 120 may include one or more nitric oxide sensors 120 that are configured to detect one or more nitric oxide synthases. In some embodiments, one or more nitric oxide sensors 120 may be configured to detect nitric oxide synthase activity. Nitric oxide synthase detection kits are commercially available (e.g., Cell Technology, Inc., Mountain View, Calif.). In some embodiments, one or more nitric oxide sensors 120 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more nitric oxide sensors 120 may be configured to detect nitric oxide synthase through immunological methods. Methods that may be used to detect nitric oxide synthase directly been reported (e.g., Burrell et al., J. Histochem. Cytochem., 44:339-346 (1996) and Hattenbach et al., Opthalmologica, 216:209-214 (2002)). In some embodiments, microelectromechanical systems may be used to detect nitric oxide synthase. In some embodiments, antibodies and/or aptamers that bind to nitric oxide synthase may be used within one or more microelectromechanical systems to detect nitric oxide synthase. Methods to construct microelectromechanical detectors have been described (e.g., Gau et al., Biosensors & Bioelectronics, 16:745-755 (2001)). Accordingly, nitric oxide sensors may be configured in numerous ways to detect one or more nitric oxide synthases.

At embodiment 1806, module 1750 may include one or more nitric oxide sensors that are configured to detect one or more nitric oxide donors. In some embodiments, one or more nitric oxide sensors 120 may include one or more nitric oxide sensors 120 that are configured to detect one or more nitric oxide donors. In some embodiments, one or more nitric oxide sensors 120 may include one or more surface plasmon resonance chemical electrodes that are configured to detect one or more nitric oxide donors. For example, in some embodiments, one or more nitric oxide sensors 120 may include one or more surface plasmon resonance chemical electrodes that include antibodies and/or aptamers that bind to one or more nitric oxide donors. Accordingly, such electrodes may be used to detect the one or more nitric oxide donors through use of surface plasmon resonance. Methods to construct surface plasmon resonance chemical electrodes are known and have been described (e.g., U.S. Pat. No. 5,858,799; Lin et al., Applied Optics, 46:800-806 (2007)). In some embodiments, antibodies and/or aptamers that bind to one or more nitric oxide donors may be used within one or more microelectromechanical systems to detect one or more nitric oxide donors. Methods to construct microelectromechanical detectors have been described (e.g., Gau et al., Biosensors & Bioelectronics, 16:745-755 (2001)).

At embodiment 1808, module 1750 may include one or more nitric oxide sensors that are operably associated with the one or more control units. In some embodiments, a device 102 may include one or more nitric oxide sensors 120 that are operably associated with one or more control units 116. In some embodiments, one or more nitric oxide sensors 120 may be operably associated with one or more control units 116 through a hardwired connection. In some embodiments, one or more nitric oxide sensors 120 may be operably associated with one or more control units 116 through a wireless connection. In some embodiments, one or more nitric oxide sensors 120 may be configured to send one or more signals 118 to one or more control units 116. In some embodiments, one or more nitric oxide sensors 120 may be configured to receive one or more signals 118 from one or more control units 116.

At embodiment 1810, module 1750 may include one or more nitric oxide sensors that are configured to transmit one or more information packets. In some embodiments, one or more nitric oxide sensors 120 may be configured to transmit one or more information packets. In some embodiments, one or more nitric oxide sensors 120 may be configured to transmit one or more information packets to one or more control units 116. Information packets may include numerous types of information. Examples of such information include, but are not limited to, nitric oxide concentration, temperature, time, and the like.

At embodiment 1812, module 1750 may include one or more nitric oxide sensors that are configured to transmit one or more signals. In some embodiments, one or more nitric oxide sensors 120 may be configured to transmit one or more signals 118. In some embodiments, one or more nitric oxide sensors 120 may be configured to transmit one or more signals 118. Numerous types of signals 118 may be transmitted. Examples of such signals 118 include, but are not limited to, optical signals 118, radio signals 118, wireless signals 118, hardwired signals 118, infrared signals 118, ultrasonic signals 118, and the like.

At embodiment 1814, module 1750 may include one or more nitric oxide sensors that include one or more electrochemical sensors. In some embodiments, a device 102 may include one or more nitric oxide sensors 120 that include one or more electrochemical sensors. Nitric oxide sensors 120 may include numerous types of electrochemical sensors. For example, in some embodiments, an electrochemical sensor may be configured as a nitric oxide specific electrode. In some embodiments, a nitric oxide specific electrode may include ruthenium and/or at least one oxide of ruthenium. Methods to construct such electrodes are known and have been described (e.g., U.S. Pat. Nos. 6,280,604; 5,980,705). In some embodiments, a nitric oxide sensor 120 may include an amperometric sensor that includes a sensing electrode that is configured to oxidize nitric oxide complexes to generate an electrical current that indicates the concentration of nitric oxide. Methods to construct such electrodes are known and have been described (e.g., U.S. Patent Application No.: 20070181444). Numerous types of electrochemical sensors may be associated with one or more nitric oxide sensors 120 (e.g., Li et al., Electroanalysis, 18:713-718 (2006)). Electrodes that may be used to detect nitric oxide are commercially available (World Precision Instruments, Sarasota, Fl). In some embodiments, such electrodes may be used to detect nitric oxide at concentrations of about 0.5 nanomolar and above, and may be about 100 micrometers in diameter (World Precision Instruments, Sarasota, Fl).

FIG. 19 illustrates alternative embodiments of embodiment 1700 of device 102 of FIG. 17. FIG. 19 illustrates example embodiments of module 1750. Additional embodiments may include an embodiment 1902, an embodiment 1904, an embodiment 1906, and/or an embodiment 1908.

At embodiment 1902, module 1750 may include one or more nitric oxide sensors that include one or more semiconductor sensors. In some embodiments, one or more nitric oxide sensors 120 may include one or more nitric oxide sensors 120 that include one or more semiconductor sensors. In some embodiments, the sensor may be a molecular controlled semiconductor resistor of a multilayered GaAs structure to which a layer of multifunctional NO-binding molecules are adsorbed. Such nitric oxide binding molecules may include, but are not limited to, vicinal diamines, metalloporphyrins, metallophthalocyanines, and iron-dithiocarbamate complexes that contain at least one functional group selected from carboxyl, thiol, acyclic sulfide, cyclic disulfide, hydroxamic acid, trichlorosilane or phosphate (e.g., U.S. Published Patent Application No.: 20040072360). In some embodiments, a semiconductive nitric oxide sensor 120 may employ a polycrystalline-oxide semiconductor material that is coated with porous metal electrodes to form a semiconductor sandwich. In some embodiments, the semiconductor material may be formed of $SnO_2$ or ZnO. The porous electrodes may be formed with platinum and used to measure the conductivity of the semiconductor material. The conductivity of the semiconductor material changes when nitric oxide is absorbed on the surface of the semiconductor material (e.g., U.S. Pat. No. 5,580,433). Numerous other semiconductor sensors may be used to detect nitric oxide.

At embodiment 1904, module 1750 may include one or more nitric oxide sensors that include one or more chemical sensors. In some embodiments, a device 102 may include one or more nitric oxide sensors 120 that include one or more chemical sensors. For example, in some embodiments, one or more nitric oxide sensors 120 may include one or more chemical sensors that include a reagent solution that undergoes a chemiluminescent reaction with nitric oxide. Accordingly, one or more photodetectors may be used to detect nitric oxide. Methods to construct such detectors are known and have been described (e.g., U.S. Pat. No. 6,100,096). In some embodiments, ozone may be reacted with nitric oxide to produce light in proportion to the amount of nitric oxide present. The light produced may be measured with a photodetector. In some embodiments, sensors may include one or more charge-coupled devices to detect photonic emission.

At embodiment 1906, module 1750 may include one or more nitric oxide sensors that include one or more fluorescent sensors. In some embodiments, a device 102 may include one or more nitric oxide sensors 120 that include one or more fluorescent sensors. In some embodiments, a fluorescent sensor may include one or more fluorescent probes that may be used to detect nitric oxide. For example, in some embodiments, 4,5-diaminofluorescein may be used to determine nitric oxide concentration (e.g., Rathel et al., Biol. Proced. Online, 5:136-142 (2003)). Probes that may be used to detect nitric oxide are commercially available (EMD Chemicals Inc., San Diego, Calif.).

At embodiment 1908, module 1750 may include one or more nitric oxide sensors that include one or more Raman sensors. In some embodiments, one or more nitric oxide sensors 120 may include one or more nitric oxide sensors 120 that include one or more Raman sensors. Methods to use Raman spectroscopy to detect nitric oxide are known and have been described (e.g., U.S. Patent Application No.: 20060074282). In addition, Raman spectrometers are commercially available (e.g., Raman Systems, Austin, Tex. and B&W Tek, Inc., Newark, Del.).

FIG. 20A illustrates an embodiment of device 102. Photolyzable nitric oxide donor 104 is shown in association with light source 106.

FIG. 20B illustrates an embodiment of device 102. Photolyzable nitric oxide donor 104 is shown in association with light source 106 and nitric oxide permeable membrane 2000.

FIG. 20C illustrates an embodiment of device 102. Photolyzable nitric oxide donor 104 is shown in association with light source 106, and control unit 116.

FIG. 20D illustrates an embodiment of device 102. Photolyzable nitric oxide donor 104 is shown in association with light source 106, control unit 116, and nitric oxide permeable membrane 2000.

FIG. 20E illustrates an embodiment of device 102. Photolyzable nitric oxide donor 104 is shown in association with light source 106, control unit 116, and nitric oxide permeable housing 114 that includes a nitric oxide permeable membrane 2000.

FIG. 21A illustrates an embodiment of device 102. Photolyzable nitric oxide donor 104 is shown in association with light source 106, and control unit 116. Control unit 116 is shown associated with light source 106 through a hardwired connection 2100.

FIG. 21B illustrates an embodiment of device 102. Photolyzable nitric oxide donor 104 is shown in association with light source 106, control unit 116, and receiver 2110. Control unit 116 is shown associated with receiver 2110 through a wireless connection 2120.

FIG. 21C illustrates an embodiment of device 102. Photolyzable nitric oxide donor 104 is shown in association with light source 106, control unit 116, and nitric oxide permeable membrane 2000. Control unit 116 is shown associated with light source 106 through a hardwired connection 2100.

FIG. 21D illustrates an embodiment of device 102. Photolyzable nitric oxide donor 104 is shown in association with light source 106, control unit 116, nitric oxide permeable membrane 2000, and receiver 2110. Control unit 116 is shown associated with receiver 2110 through a wireless connection 2120.

FIG. 22A illustrates an embodiment of device 102. Photolyzable nitric oxide donor 104 is shown in association with light emitter 2210. Battery 2200 is shown associated with light emitter 2210 through a hardwired connection 2220.

FIG. 22B illustrates an embodiment of device 102. Photolyzable nitric oxide donor 104 is shown in association with light emitter 2210 and nitric oxide permeable membrane 2000. Battery 2200 is shown associated with light emitter 2210 through a hardwired connection 2220.

FIG. 22C illustrates an embodiment of device 102. Photolyzable nitric oxide donor 104 is shown in association with light source 106, nitric oxide permeable membrane 2000, and control unit 116.

FIG. 23A illustrates an embodiment of device 102. Photolyzable nitric oxide donor 104 is shown in association with light source 106. Control unit 116 is shown associated with light source 106 through a hardwired connection 2100.

FIG. 23B illustrates an embodiment of device 102. Photolyzable nitric oxide donor 104 is shown in association with light source 106 and receiver 2110. Control unit 116 is shown associated with receiver 2110 through a wireless connection 2120.

FIG. 23C illustrates an embodiment of device 102. Photolyzable nitric oxide donor 104 is shown in association with light source 106 and nitric oxide permeable membrane 2000. Control unit 116 is shown associated with light source 106 through a hardwired connection 2100.

FIG. 23D illustrates an embodiment of device 102. Photolyzable nitric oxide donor 104 is shown in association with light source 106, receiver 2110 and nitric oxide permeable membrane 2000. Control unit 116 is shown associated with receiver 2110 through a wireless connection 2120.

FIG. 24A illustrates an embodiment of device 102. Photolyzable nitric oxide donor 104 is shown in association with light source 106. The photolyzable nitric oxide donor 104 and light source 106 are enclosed within a nitric oxide permeable housing 114 that includes a nitric oxide permeable membrane 2000.

FIG. 24B illustrates an embodiment of device 102. Photolyzable nitric oxide donor 104 is shown in association with light source 106. The photolyzable nitric oxide donor 104 and light source 106 are enclosed within a nitric oxide permeable housing 114 that includes a nitric oxide permeable membrane 2000.

FIG. 24C illustrates an embodiment of device 102. Photolyzable nitric oxide donor 104 is shown enclosed within a nitric oxide permeable housing 114 that includes a nitric oxide permeable membrane 2000. Light source 106 is shown as being positioned within a cavity of the nitric oxide permeable housing 114 and associated with a control unit 116.

FIG. 25A illustrates an embodiment of device 102. Photolyzable nitric oxide donor 104 is shown enclosed within a nitric oxide permeable housing 114 that includes a nitric oxide permeable membrane 2000. Light source 106 is shown as being positioned within the nitric oxide permeable housing 114 in association with a light permeable barrier 2500.

FIG. 25B illustrates an embodiment of device 102. Photolyzable nitric oxide donor 104 is shown enclosed within a nitric oxide permeable housing 114 that includes a nitric oxide permeable membrane 2000. Light source 106 is shown as being positioned within the nitric oxide permeable housing 114 in association with a light permeable barrier 2500.

FIG. 25C illustrates an embodiment of device 102. Photolyzable nitric oxide donor 104 is shown enclosed within a nitric oxide permeable housing 114 that includes a nitric oxide permeable membrane 2000. Light source 106 is shown as being positioned within a cavity of the nitric oxide permeable housing 114 and associated with a control unit 116.

FIG. 26A illustrates an embodiment of device 102. Photolyzable nitric oxide donor 104 is shown enclosed within a nitric oxide permeable housing 114 that includes a controllable valve 2600. Light source 106 is shown as being positioned within the nitric oxide permeable housing 114. Receiver 2110 is associated with the nitric oxide permeable housing 114.

FIG. 26B illustrates an embodiment of device 102. Photolyzable nitric oxide donor 104 is shown enclosed within a nitric oxide permeable housing 114 that includes a controllable valve 2600. Light source 106 is shown as being positioned within the nitric oxide permeable housing 114. Receiver 2110 is associated with the nitric oxide permeable housing 114.

FIG. 26C illustrates an embodiment of device 102. Photolyzable nitric oxide donor 104 is shown enclosed within a nitric oxide permeable housing 114 that includes a controllable valve 2600. Light source 106 is shown as being positioned within a cavity of the nitric oxide permeable housing 114 and associated with a control unit 116.

FIG. 27A illustrates an embodiment of nitric oxide permeable housing 114. Nitric oxide permeable housing 114 is illustrated as including a nitric oxide impermeable portion 2720 of the nitric oxide permeable housing 114 and a nitric oxide permeable membrane 2000. The nitric oxide permeable housing 114 includes a cavity 2710 configured to accept one or more light sources 106 and a cavity 2700 configured to accept one or more photolyzable nitric oxide donors 104.

FIG. 27B illustrates an embodiment of nitric oxide permeable housing 114. Nitric oxide permeable housing 114 is illustrated as including a nitric oxide permeable membrane 2000 that includes a cavity 2700 configured to accept one or more photolyzable nitric oxide donors 104. The nitric oxide permeable housing 114 includes a cavity 2710 configured to accept one or more light sources 106. Nitric oxide permeable housing 114 includes a light permeable barrier 2500 that separates the cavity 2700 configured to accept one or more photolyzable nitric oxide donors 104 from the cavity 2710 configured to accept one or more light sources 106.

FIG. 27C illustrates an embodiment of nitric oxide permeable housing 114. Nitric oxide permeable housing 114 is illustrated as including a nitric oxide impermeable portion 2720 of the nitric oxide permeable housing 114 and a nitric oxide permeable membrane 2000. Nitric oxide permeable housing 114 is illustrated as including a cavity 2700 configured to accept one or more photolyzable nitric oxide donors 104. The nitric oxide permeable housing 114 includes a cavity 2710 configured to accept one or more light sources 106. Nitric oxide permeable housing 114 includes a light permeable barrier 2500 that separates the cavity 2700 configured to accept one or more photolyzable nitric oxide donors 104 from the cavity 2710 configured to accept one or more light sources 106.

FIG. 27D illustrates an embodiment of nitric oxide permeable housing 114. Nitric oxide permeable housing 114 is illustrated as including a nitric oxide permeable membrane 2000. Nitric oxide permeable housing 114 includes a cavity 2700 configured to accept one or more photolyzable nitric oxide donors 104. The nitric oxide permeable housing 114 includes a cavity 2710 configured to accept one or more light sources 106.

FIG. 28A illustrates an embodiment of nitric oxide permeable housing 114. Nitric oxide permeable housing 114 is illustrated as including a nitric oxide impermeable portion 2720 of the nitric oxide permeable housing 114 and a controllable valve 2600. The nitric oxide permeable housing 114 includes a cavity 2710 configured to accept one or more light sources 106 and a cavity 2700 configured to accept one or more photolyzable nitric oxide donors 104.

FIG. 28B illustrates an embodiment of nitric oxide permeable housing 114. Nitric oxide permeable housing 114 is illustrated as including a nitric oxide impermeable portion 2720 of the nitric oxide permeable housing 114 and a controllable valve 2600. The nitric oxide permeable housing 114 includes a cavity 2710 configured to accept one or more light sources 106 and a cavity 2700 configured to accept one or more photolyzable nitric oxide donors 104.

FIG. 28C illustrates an embodiment of nitric oxide permeable housing 114. Nitric oxide permeable housing 114 is illustrated as including a nitric oxide impermeable portion 2720 of the nitric oxide permeable housing 114 and a controllable valve 2600. The nitric oxide permeable housing 114 includes a cavity 2710 configured to accept one or more light sources 106 and a cavity 2700 configured to accept one or more photolyzable nitric oxide donors 104.

Figure 29:
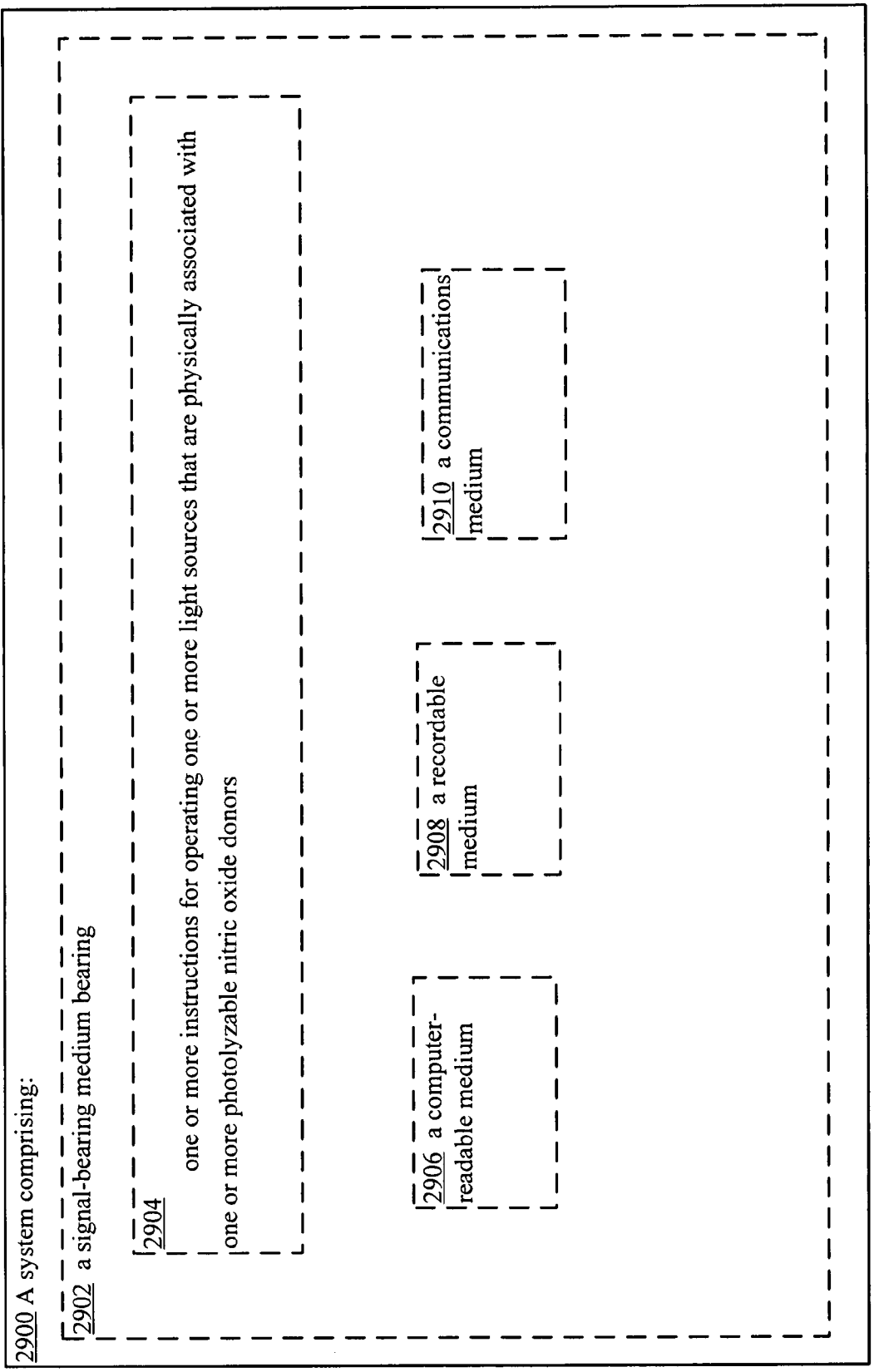
FIG. 29 illustrates a partial view of a system 2900 that includes a computer program for executing a computer process on a computing device.

FIG. 29 illustrates a partial view of a system 2900 that includes a computer program 2904 for executing a computer process on a computing device. An embodiment of the system 2900 is provided using a signal-bearing medium 2902 bearing at least one of one or more instructions for operating one or more light sources that are physically associated with one or more photolyzable nitric oxide donors. The one or more instructions may be, for example, computer executable and/or logic-implemented instructions. In some embodiments, the signal-bearing medium 2902 may include a computer-readable medium 2906. In some embodiments, the signal bearing medium 2902 may include a recordable medium 2908. In some embodiments, the signal bearing medium 2902 may include a communications medium 2910.

Figure 30:
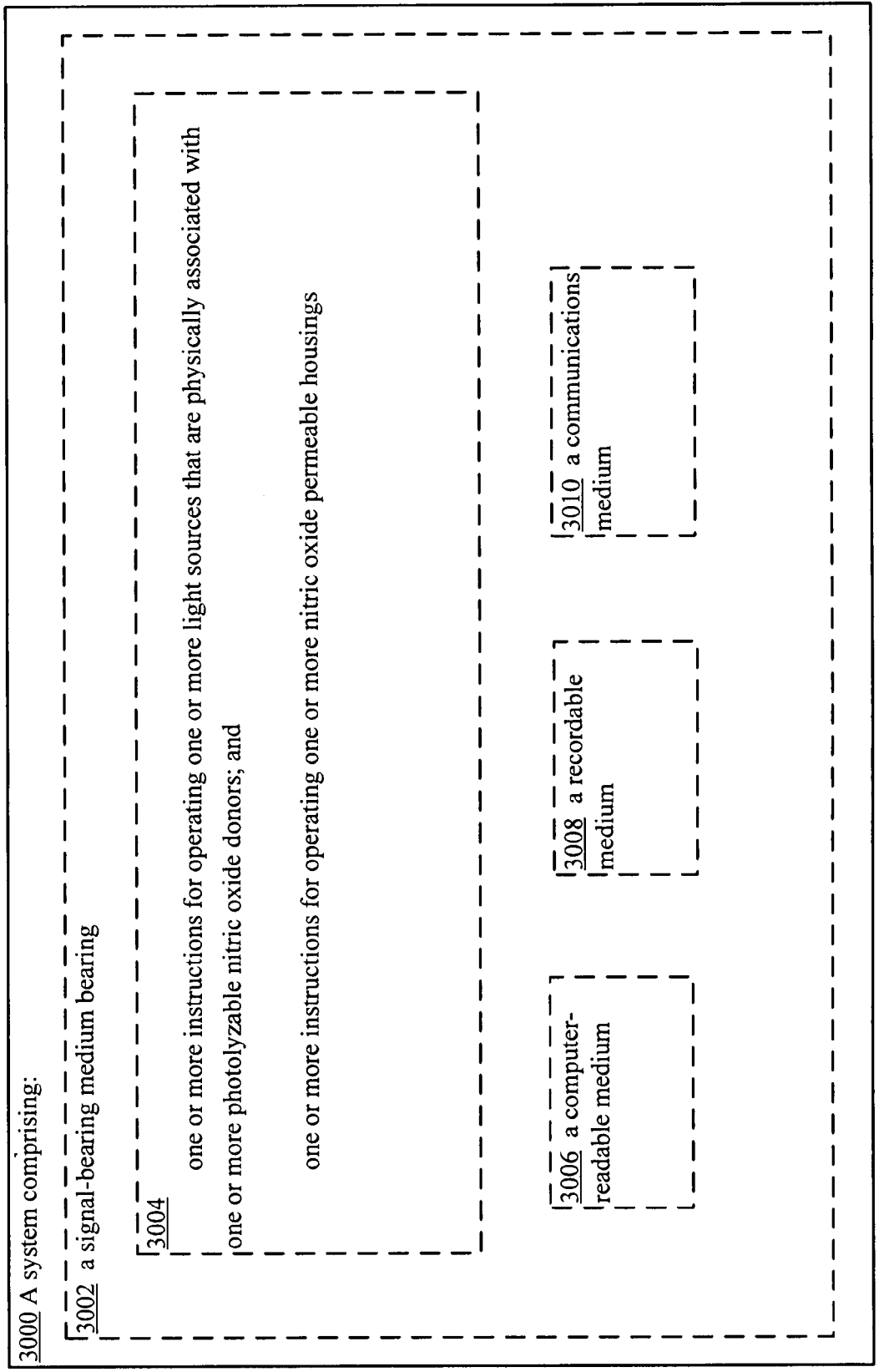
FIG. 30 illustrates a partial view of a system 3000 that includes a computer program for executing a computer process on a computing device.

FIG. 30 illustrates a partial view of a system 3000 that includes a computer program 3004 for executing a computer process on a computing device. An embodiment of the system 3000 is provided using a signal-bearing medium 3002 bearing at least one of one or more instructions for operating one or more light sources that are physically associated with one or more photolyzable nitric oxide donors and one or more instructions for operating one or more nitric oxide permeable housings. The one or more instructions may be, for example, computer executable and/or logic-implemented instructions. In some embodiments, the signal-bearing medium 3002 may include a computer-readable medium 3006. In some embodiments, the signal bearing medium 3002 may include a recordable medium 3008. In some embodiments, the signal bearing medium 3002 may include a communications medium 3010.

Figure 31:
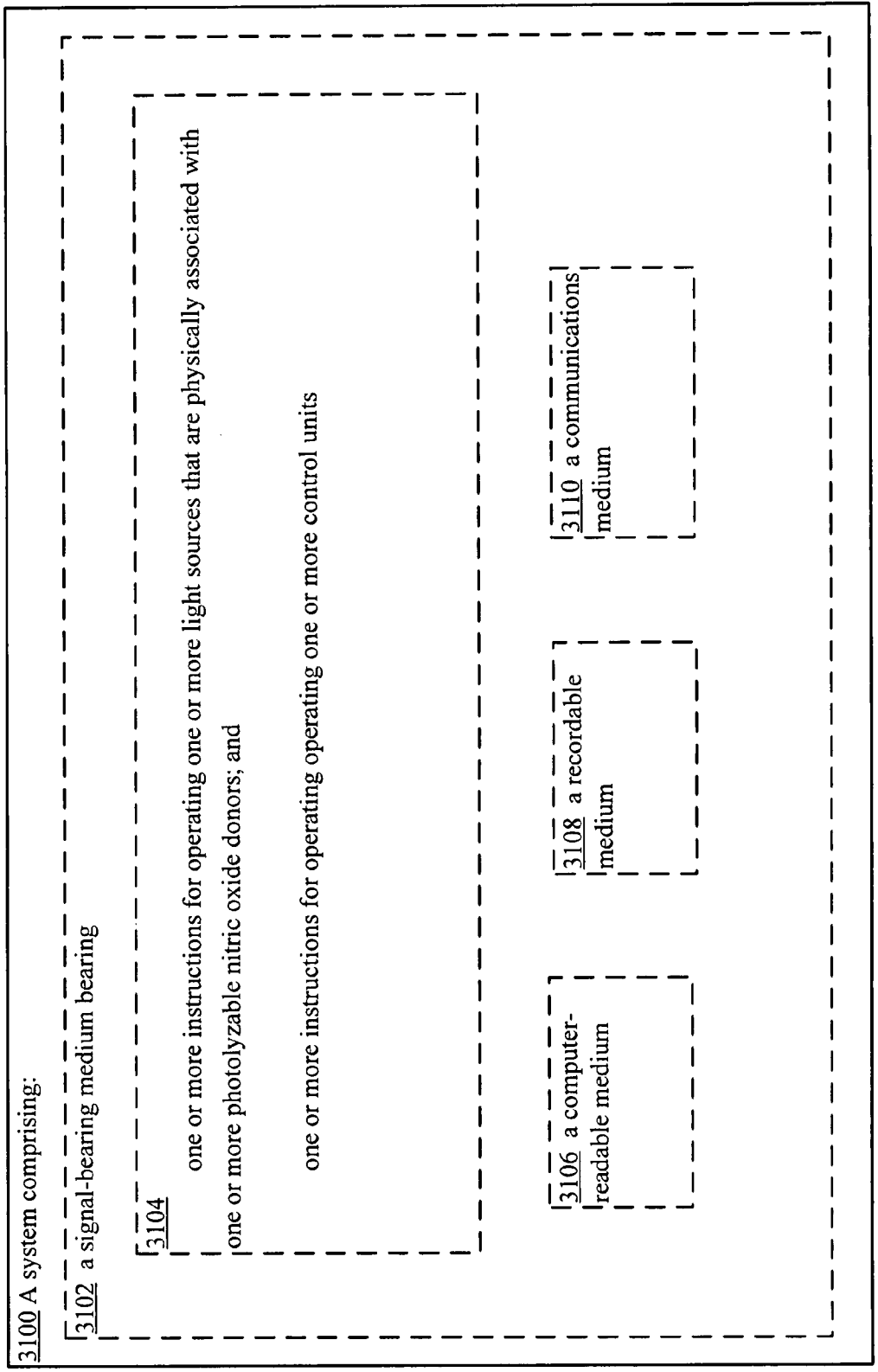
FIG. 31 illustrates a partial view of a system 3100 that includes a computer program for executing a computer process on a computing device.

FIG. 31 illustrates a partial view of a system 3100 that includes a computer program 3104 for executing a computer process on a computing device. An embodiment of the system 3100 is provided using a signal-bearing medium 3102 bearing at least one of one or more instructions for operating one or more light sources that are physically associated with one or more photolyzable nitric oxide donors and one or more instructions for operating one or more control units. The one or more instructions may be, for example, computer executable and/or logic-implemented instructions. In some embodiments, the signal-bearing medium 3102 may include a computer-readable medium 3106. In some embodiments, the signal bearing medium 3102 may include a recordable medium 3108. In some embodiments, the signal bearing medium 3102 may include a communications medium 3110.

Figure 32:
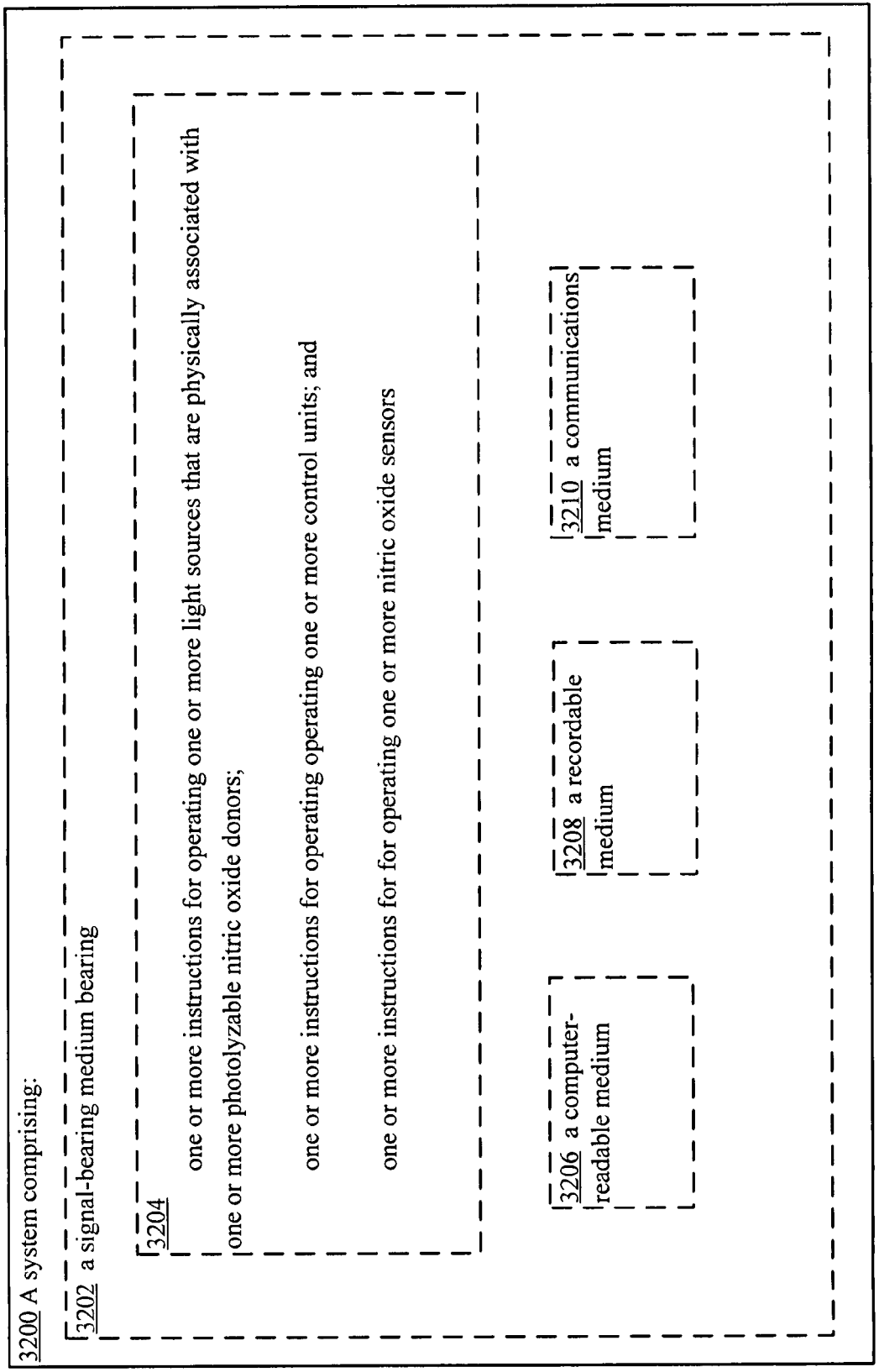
FIG. 32 illustrates a partial view of a system 3200 that includes a computer program for executing a computer process on a computing device.

FIG. 32 illustrates a partial view of a system 3200 that includes a computer program 3204 for executing a computer process on a computing device. An embodiment of the system 3200 is provided using a signal-bearing medium 3202 bearing at least one of one or more instructions for operating one or more light sources that are physically associated with one or more photolyzable nitric oxide donors, one or more instructions for operating one or more control units, and one or more instructions for operating one or more nitric oxide sensors. The one or more instructions may be, for example, computer executable and/or logic-implemented instructions. In some embodiments, the signal-bearing medium 3202 may include a computer-readable medium 3206. In some embodiments, the signal bearing medium 3202 may include a recordable medium 3208. In some embodiments, the signal bearing medium 3202 may include a communications medium 3210.

Figure 33:
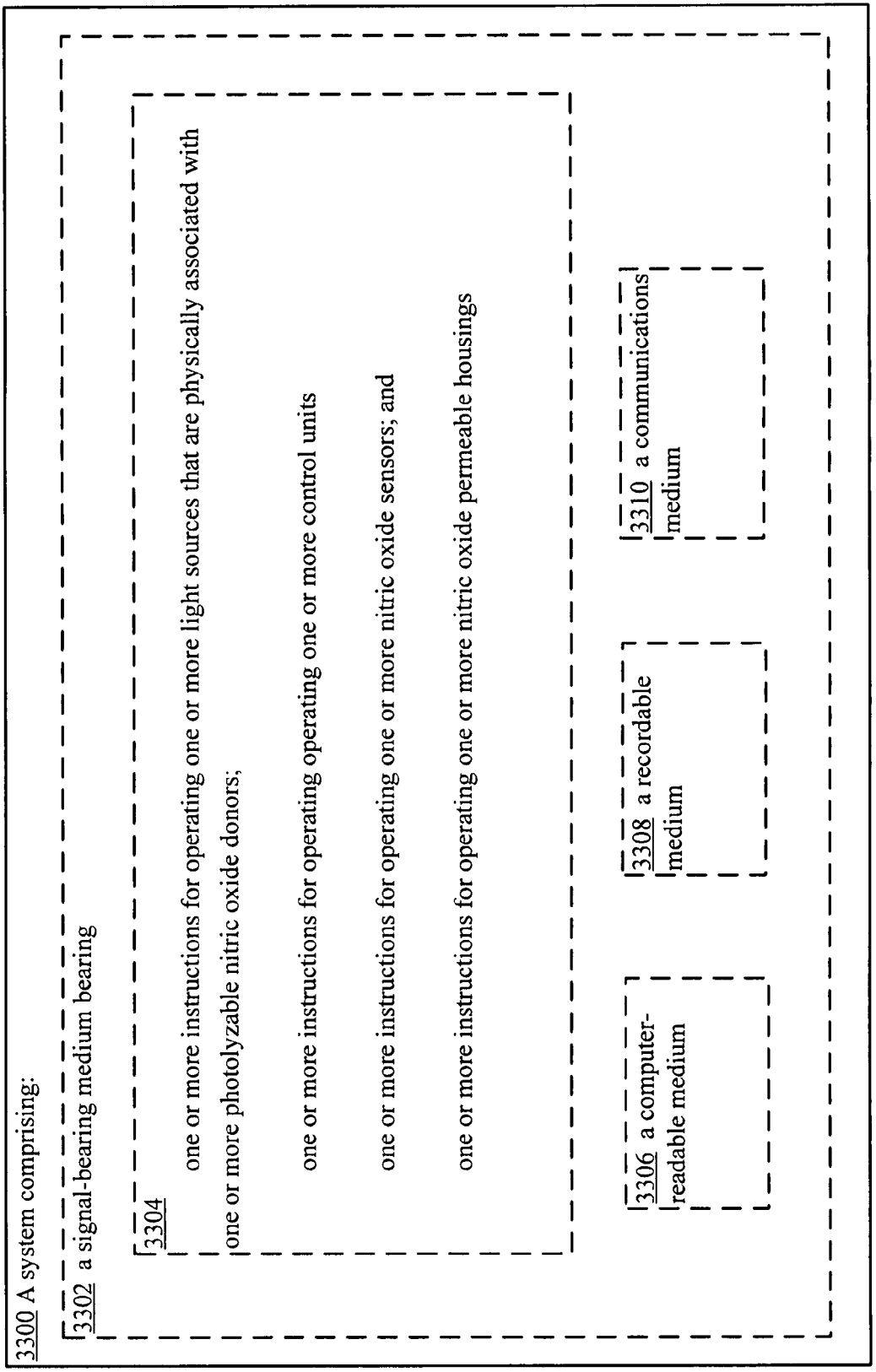
FIG. 33 illustrates a partial view of a system 3300 that includes a computer program for executing a computer process on a computing device.

FIG. 33 illustrates a partial view of a system 3300 that includes a computer program 3304 for executing a computer process on a computing device. An embodiment of the system 3300 is provided using a signal-bearing medium 3302 bearing at least one of one or more instructions for operating one or more light sources that are physically associated with one or more photolyzable nitric oxide donors, one or more instructions for operating one or more control units, and one or more instructions for operating one or more nitric oxide sensors. The one or more instructions may be, for example, computer executable and/or logic-implemented instructions. In some embodiments, the signal-bearing medium 3302 may include a computer-readable medium 3306. In some embodiments, the signal bearing medium 3302 may include a recordable medium 3308. In some embodiments, the signal bearing medium 3302 may include a communications medium 3310.

Figure 34:
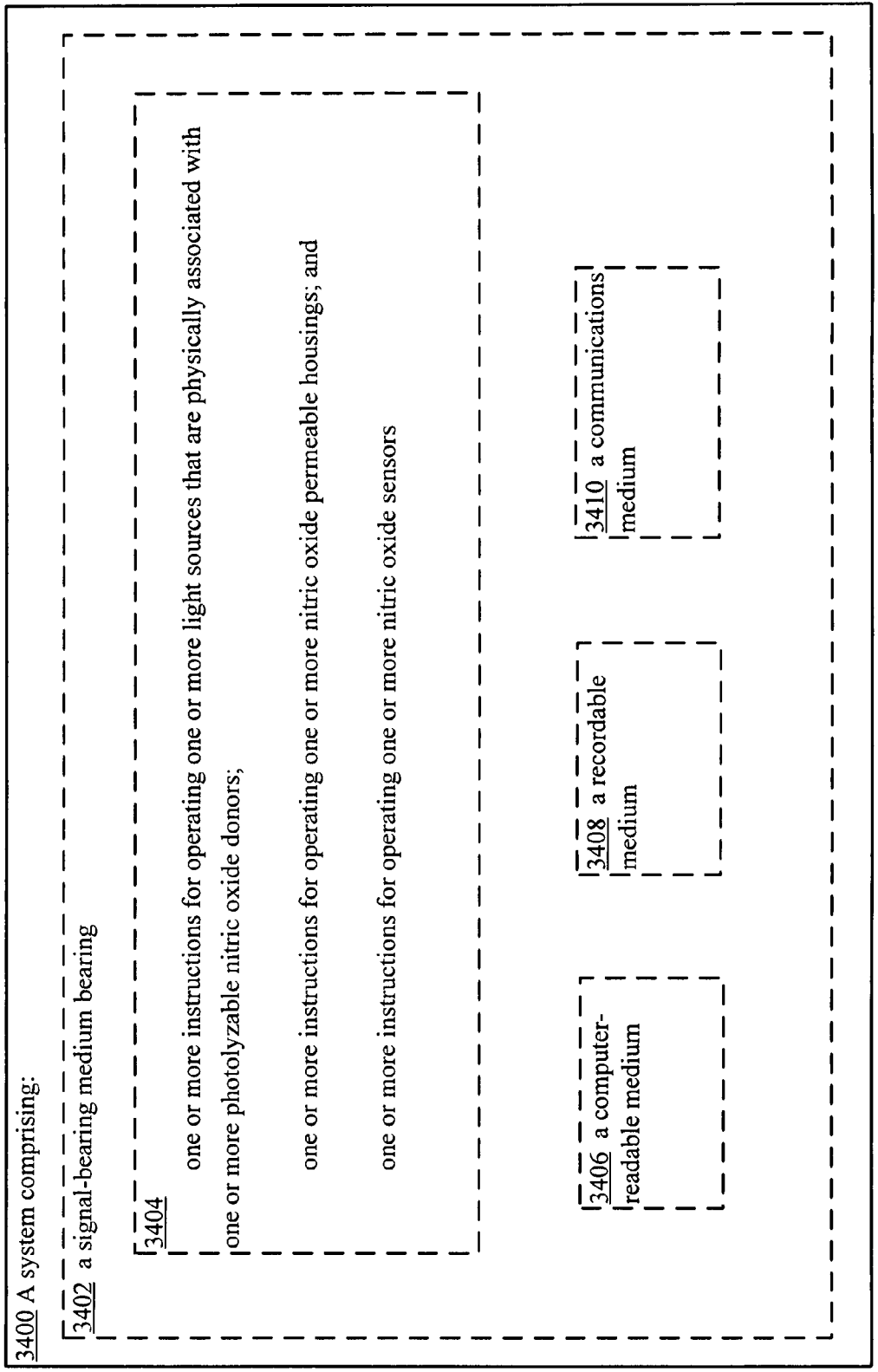
FIG. 34 illustrates a partial view of a system 3400 that includes a computer program for executing a computer process on a computing device.

FIG. 34 illustrates a partial view of a system 3400 that includes a computer program 3404 for executing a computer process on a computing device. An embodiment of the system 3400 is provided using a signal-bearing medium 3402 bearing at least one of one or more instructions for operating one or more light sources that are physically associated with one or more photolyzable nitric oxide donors, one or more instructions for operating one or more nitric oxide permeable housings, and one or more instructions for operating one or more nitric oxide sensors. The one or more instructions may be, for example, computer executable and/or logic-implemented instructions. In some embodiments, the signal-bearing medium 3402 may include a computer-readable medium 3406. In some embodiments, the signal bearing medium 3402 may include a recordable medium 3408. In some embodiments, the signal bearing medium 3402 may include a communications medium 3410.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electromechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although the user interface 124 is shown/described herein as a single illustrated figure that is associated with an individual 126, those skilled in the art will appreciate that a user interface 124 may be utilized by a user that is a representative of a human user, a robotic user (e.g., computational entity), and/or substantially any combination thereof (e.g., a user may be assisted by one or more robotic based systems). In addition, a user as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A device comprising:
    one or more nitric oxide permeable housings, one or more photolyzable nitric oxide donors enclosed within the one or more nitric oxide permeable housings,
    one or more light sources that are physically associated with the one or more photolyzable nitric oxide donors and enclosed within the one or more nitric oxide permeable housings; and
    one or more control units that are operably associated with the one or more light sources.

2. The device of claim 1, wherein the one or more photolyzable nitric oxide donors comprise:
    one or more photolyzable nitric oxide donors that include one or more diazeniumdiolates.

3. The device of claim 1, wherein the one or more photolyzable nitric oxide donors comprise:
    one or more photolyzable nitric oxide donors that are associated with one or more quantum dots.

4. The device of claim 1, wherein the one or more photolyzable nitric oxide donors comprise:
    one or more photolyzable nitric oxide donors that are associated with one or more rare-earth materials.

5. The device of claim 1, wherein the one or more light sources that are physically associated with the one or more photolyzable nitric oxide donors comprise:
    one or more electromagnetic receivers.

6. The device of claim 1, wherein the one or more light sources that are physically associated with the one or more photolyzable nitric oxide donors comprise:
    one or more light sources that are coated with at least one of the one or more photolyzable nitric oxide donors.

7. The device of claim 1, wherein the one or more light sources that are physically associated with the one or more photolyzable nitric oxide donors comprise:
    one or more light sources that are associated with one or more optical waveguides.

8. The device of claim 1, wherein the one or more light sources that are physically associated with the one or more photolyzable nitric oxide donors comprise:
    one or more light sources that are associated with one or more quantum dots.

9. The device of claim 1, wherein the one or more light sources that are physically associated with the one or more photolyzable nitric oxide donors comprise:
one or more light sources that are associated with one or more rare-earth materials.

10. The device of claim 1, wherein the one or more light sources that are physically associated with the one or more photolyzable nitric oxide donors comprise:
one or more light sources that emit infrared light.

11. The device of claim 1, wherein the one or more light sources that are physically associated with the one or more photolyzable nitric oxide donors comprise:
one or more light sources that are configured to emit light that specifically facilitates release of nitric oxide from the one or more nitric oxide donors.

12. The device of claim 1, wherein the one or more light sources that are physically associated with the one or more photolyzable nitric oxide donors comprise:
one or more light sources that are configured to emit light that is selected to avoid damaging one or more tissues.

13. The device of claim 1, wherein the one or more nitric oxide permeable housings comprise:
one or more nitric oxide permeable housings that include one or more nitric oxide permeable membranes.

14. The device of claim 1, wherein the one or more control units comprise:
one or more receivers that are configured to receive one or more signals.

15. The device of claim 1, wherein the one or more control units comprise:
one or more receivers that are configured to receive one or more signals from one or more sensors.

16. The device of claim 1, wherein the one or more control units comprise:
one or more control units that regulate the one or more light sources.

17. The device of claim 1, wherein the one or more control units comprise:
one or more control units that are responsive to one or more programs.

18. The device of claim 1, wherein the one or more control units comprise:
one or more control units that are responsive to one or more commands.

19. The device of claim 1, wherein the one or more control units comprise:
one or more control units that are responsive to one or more timers.

20. The device of claim 1, wherein the one or more control units comprise:
one or more control units that are associated with one or more transmitters.

21. The device of claim 1, wherein the one or more control units comprise:
one or more control units that include memory.

22. The device of claim 1, wherein the one or more control units comprise:
one or more control units that include memory having one or more associated programs.

23. The device of claim 1, further comprising:
one or more nitric oxide sensors.

24. The device of claim 23, wherein the one or more nitric oxide sensors comprise:
one or more nitric oxide sensors that are configured to detect nitric oxide.

25. The device of claim 23, wherein the one or more nitric oxide sensors comprise:
one or more nitric oxide sensors that are configured to detect one or more nitric oxide donors.

26. The device of claim 23, wherein the one or more nitric oxide sensors comprise:
one or more nitric oxide sensors that are operably associated with the one or more control units.

27. The device of claim 23, wherein the one or more nitric oxide sensors comprise:
one or more nitric oxide sensors that are configured to transmit one or more information packets.

28. The device of claim 23, wherein the one or more nitric oxide sensors comprise:
one or more nitric oxide sensors that are configured to transmit one or more signals.

29. The device of claim 1, wherein the one or more nitric oxide permeable housings comprise:
one or more nitric oxide permeable housings that are regulated by the one or more control units.

30. A device comprising:
one or more nitric oxide permeable housings,
one or more photolyzable diazeniumdiolates enclosed within the one or more nitric oxide permeable housings;
one or more light sources that are enclosed within the one or more nitric oxide permeable housings and configured to emit light that facilitates release of nitric oxide from the one or more photolyzable diazeniumdiolates; and
one or more sensors that are configured to detect nitric oxide.

31. A device comprising:
one or more nitric oxide permeable housings, one or more photolyzable diazeniumdiolates enclosed within the one or more nitric oxide permeable housings;
one or more rare earth materials that facilitate upconversion of light;
one or more light sources that are enclosed within the one or more nitric oxide permeable housings and configured to emit light that is upconverted by the one or more rare earth materials to facilitate release of nitric oxide from the one or more photolyzable diazeniumdiolates; and
one or more sensors that are configured to detect nitric oxide.

* * * * *